United States Patent [19]
Blade et al.

[11] Patent Number: 5,202,356
[45] Date of Patent: Apr. 13, 1993

[54] PESTICIDAL CYCLOPROPYL-2,4-DIENEAMIDES

[75] Inventors: Robert J. Blade; George S. Cockerill; John E. Robinston, all of Hertfordshire, England

[73] Assignee: The Wellcome Foundation Limited, London, England

[21] Appl. No.: 729,847

[22] Filed: Jul. 12, 1991

Related U.S. Application Data

[63] Continuation of Ser. No. 436,803, Nov. 15, 1989, abandoned.

[30] Foreign Application Priority Data

Nov. 16, 1988 [GB] United Kingdom ............... 8826760

[51] Int. Cl.$^5$ ........................................... A01N 37/18
[52] U.S. Cl. ..................... 514/617; 514/63;
514/357; 514/438; 514/467; 514/599; 514/622;
514/624; 546/337; 549/76; 549/452; 556/419;
564/74; 564/161; 564/171; 564/180; 564/181;
564/190
[58] Field of Search ............... 564/190, 191, 171, 74,
564/161, 180, 181; 514/599, 617, 624, 357, 367,
622, 63; 546/337; 549/452; 556/419

[56] References Cited

FOREIGN PATENT DOCUMENTS

| | | |
|---|---|---|
| 0111105 | 6/1984 | European Pat. Off. |
| 0143593 | 6/1985 | European Pat. Off. |
| 0225011 | 6/1987 | European Pat. Off. |
| 0228222 | 7/1987 | European Pat. Off. |
| 0228853 | 7/1987 | European Pat. Off. |
| 0269457 | 6/1988 | European Pat. Off. |
| 0194764 | 7/1989 | European Pat. Off. |
| 2488603 | 3/1982 | France . |
| 57-212150 | 12/1982 | Japan . |

OTHER PUBLICATIONS

Nilsen et al, J. Chem. Soc. Chem. Commun., pp. 128–129, 1987.
Itoh et al, Bull. Chem. Soc. Jpn. 48(12), 3698–3701, 1975.
Manisse et al, Tetrahedron, 33(18), pp. 2300–2406, 1977.
Chemical Abstracts, vol. 88, No. 21, May 22, 1978, Abstract No. 152313j Manisse et al, "Thermal Rearrangement of Trans Alpha-ethylenic . . . ".
Chemical Abstracts, vol. 97, No. 11, Sep. 13, 1982, Abstract No. 91921t Bonin et al, "Acaricidal (1R;, cis-)-2,2-dimethyl-3-(2,2-difluoroethenyl) . . . ".
Receuil, 1958, vol. 77, pp. 97–103, Smit et al, "Investigations on Organic Insecticides".
J. Indian Chem. Soc., vol. LI, Sep. 1974, pp. 817–818, Vig et al "Synthesis of Piperovatine".
Chemical Abstracts, vol. 78, No. 4, Jan. 29, 1973, Bordner et al "E-2-(p-nitrophenyl) cyclopropyl methyl ketone", $C_{11}H_{11}NO_3$, Abstract 21275u.
Chemical Abstracts, vol. 89, No. 5, Jul. 31, 1978, Nilsen et al, Abstract No. 42501g, "Cyclopropylidene Insertion", p. 548.
Chemical Abstracts, vol. 84, No. 13, Mar. 29, 1976, Itoh et al, Abstract No. 89130x, p. 444, "Kinetics and Stereochemistry of Alkaline Clevage of . . . ".
Aust. J. Chem., 1966, 19, pp. 1215–1220, Meisters et al, "The Isobutylamides of 7-Phenylhepta-2,4-Dienoic Acid . . . ".

Primary Examiner—Carolyn Elmore
Assistant Examiner—Scott C. Rand
Attorney, Agent, or Firm—Nixon & Vanderhye

[57] ABSTRACT

The present Application discloses pesticidally active compounds of the formula (I):

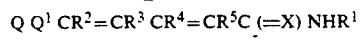

$$Q\ Q^1\ CR^2=CR^3\ CR^4=CR^5C\ (=X)\ NHR^1$$

or a salt thereof, wherein Q is an monocyclic aromatic ring, or fused bicyclic ring system of which at least one ring is aromatic containing 9 or 10 atoms of which one may be nitrogen and the rest carbon each optionally substituted, or Q is a dihalovinyl group or a group $R^6$—C≡C— where $R^6$ is $C_{1-4}$ alkyl, tri $C_{1-4}$ alkylsilyl, halogen or hydrogen; $Q^1$ is a 1,2-cyclopropyl ring optionally substituted by one or more groups selected from $C_{1-3}$ alkyl, halo, $C_{1-3}$ haloalkyl, alkynyl, or cyano; $R^2, R^3, R^4$ and $R^5$ are the same or different with at least one being hydrogen and the others being independently selected from hydrogen, halo, $C_{1-4}$ alkyl or $C_{1-4}$ haloalkyl; X is oxygen or sulphur; and $R^1$ is selected from hydrogen and $C_{1-8}$ hydrocarbyl optionally substituted by dioxalanyl, halo, cyano, trifluoromethyl, trifluoromethylthio or $C_{1-6}$ alkoxy, their preparation, pesticidal compositions containing them and their use against pests.

15 Claims, No Drawings

PESTICIDAL CYCLOPROPYL-2,4-DIENEAMIDES

This is a continuation of application Ser. No. 07/436,803, filed Nov. 15, 1989, now abandoned.

This invention relates to pesticidal compounds, processes for their preparation, compositions containing them and to their use in the treatment of pests.

Unsaturated amides having a methylene chain of 1 to at least 10 carbon atoms optionally including at least one oxygen or additional methylene group are known as pesticides or insecticides having various terminating groups which include within their scope optionally substituted phenyl (European Application Nos. 228222, 194764, 225011, Japanese Application No 57-212150, Meisters and Wailes: Aust. J. Chem. 1966, 19, 1215, Vig et al: J. Ind. Chem. Soc. 1974, 51(9), 817) or pyridyl (European Application 269457) or fused bicyclic ring system (European Application Nos. 143593, 228853), dihalovinyl or optionally substituted ethynyl (European Application 228222).

No disclosure is made of any cycloalkyl interstitial group linking the diene unit to the terminating group.

H. O. Huisman et al, Rev. trav. chim.. 77, 97–102, (1958) discloses a group of 5-(2,6,6-trimethyl cyclohexenyl)2,4-pentadienamides as insecticides.

It has now surprisingly been discovered that novel unsaturated amides having a 1,2-cyclopropyl ring adjacent to the diene unit linking the latter to a terminal group selected from optionally substituted monocyclic aromatic or fused bicyclic ring system, dihalovinyl or optionally substituted ethynyl have interesting pesticidal properties.

Accordingly, the present invention provides a compound of formula (I):

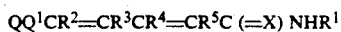

$$QQ^1CR^2=CR^3CR^4=CR^5C(=X)NHR^1 \quad (I)$$

or a salt thereof. wherein Q is an monocyclic aromatic ring. or fused bicyclic ring system of which at least one ring is aromatic containing 9 or 10 atoms of which one may be nitrogen and the rest carbon each ring system being optionally substituted, or Q is a dihalovinyl group or a group $R^6-C\equiv C-$ where $R^6$ is $C_{1-4}$ alkyl, tri $C_{1-4}$ alkylsilyl, halogen or hydrogen; $Q^1$ is a 1,2-cyclopropyl ring optionally substituted by one or more groups selected from $C_{1-3}$ alkyl, halo, $C_{1-3}$ haloalkyl, alkynyl, or cyano; $R^2, R^3, R^4$ and $R^5$ are the same or different with at least one being hydrogen and the others being independently selected from hydrogen, halo, $C_{1-4}$ alkyl or $C_{1-4}$ haloalkyl; X is oxygen or sulphur; and $R^1$ is selected from hydrogen and $C_{1-8}$ hydrocarbyl optionally substituted by dioxalanyl, halo, cyano, trifluoromethyl, trifluoromethylthio or $C_{1-6}$ alkoxy.

When Q is a monocyclic aromatic ring, this is suitably phenyl, pyridyl or thienyl and preferably phenyl. When Q is a bicyclic ring system, this is preferably naphthyl.

When Q contains an aromatic system. suitable substituents include one to four groups selected from $C_{1-6}$ hydrocarbyl, $C_{1-6}$ alkoxy or methylenedioxy, each optionally substituted by one to three halos, or from halo, cyano or nitro, or the substituent is a group $S(O)_nR^7$ wherein n is 0, 1 or 2 and $R^7$ is $C_{1-6}$ alkyl optionally substituted by one or more halos or $R^7$ is amino optionally substituted by one or two $C_{1-6}$ alkyl groups or the substituent is a group $NR^8R^9$ where $R^8$ and $R^9$ are independently selected from hydrogen, $C_{1-6}$ alkyl or a group $COR^{10}$ where $R^{10}$ is $C_{1-6}$ alkyl.

The Q ring system normally contains up to three substituents and is suitably unsubstituted or substituted by one, two or three substituents such as halo or $C_{1-4}$ haloalkyl such as trifluoromethyl. The substitution of the Q ring system depends upon the nature of this ring system but is preferably at the 3, 4 or 5 positions when Q is a 6-membered ring.

Suitably $R^2, R^3, R^4$ and $R^5$ are chosen from hydrogen, methyl or fluoro. Suitably the stereochemistry of the double bonds is (E). Suitably when $R^3$ or $R^5$ is fluoro then the stereochemistry of the double bond to which $R^3$ or $R^5$ is attached is (Z).

Preferably $R^2$ is hydrogen, $R^3$ is hydrogen or fluoro, $R^5$ is hydrogen or fluoro and $R^4$ is hydrogen or $C_{1-4}$ alkyl, most preferably methyl.

Preferably the stereometric configuration of $Q^1$ in the chain is such that the substituents are attached to the ring to give trans geometry. Preferably the 3- position of the cyclopropyl ring is unsubstituted. Suitable substituents at the 1- and 2- positions of the cyclopropyl ring include fluoro, chloro, methyl or trifluoromethyl. Preferably the 1- position is unsubstituted and the 2- position is unsubstituted or substituted by fluoro or chloro.

Suitably $R^1$ is alkyl optionally substituted by cycloalkyl, dioxalanyl, or $R^1$ is $C_{2-5}$ alkenyl. Most suitably $R^1$ is a branched chain $C_{4-6}$ alkyl group, such as isobutyl, 1,2-dimethylpropyl, 1,1,2-trimethyl propyl, 2,2-dimethylpropyl or $R^1$ is 2-methylprop-2-enyl or (2-methyl-1,3-dioxalan-2-yl) methyl. Preferably $R^1$ is isobutyl or 2-methyl-prop-2- enyl where $R^2$ and $R^3$ are hydrogen, $R^4$ is methyl and $R^5$ is hydrogen or methyl.

One suitable group of compounds of the formula (I) is that of the formula (II):

$$Q^aQ^{1a}CR^{2a}=CR^{3a}CR^{4a}=CR^{5a}C(=X^a)NHR^{1a} \quad (II)$$

or a salt thereof, wherein $Q^a$ is an optionally substituted phenyl or pyridyl group or fused bicyclic ring system of which at least one ring is aromatic containing 9 or 10 atoms of which one may be nitrogen and the rest carbon or $Q^a$ is a dihalovinyl group or a group $R^{6a}-C\equiv C-$ where $R^{6a}$ is $C_{1-4}$ alkyl, trialkylsilyl or hydrogen; $Q^{1a}$ is a 1,2-cyclopropyl ring optionally substituted by one or more groups selected from $C_{1-3}$ alkyl, halo, or $C_{1-3}$ haloalkyl; $R^{2a}, R^{3a}, R^{4a}$ and $R^{5a}$ are the same or different with at least one being hydrogen and the others being independently selected from hydrogen, halo, $C_{1-4}$ alkyl or $C_{1-4}$ haloalkyl; $X^a$ is oxygen or sulphur; and $R^{1a}$ is selected from hydrogen and $C_{1-6}$ hydrocarbyl optionally substituted by dioxalanyl, halo, cyano, trifluoromethyl, trifluoromethylthio or $C_{1-6}$ alkoxy.

When $Q^a$ contains an aromatic system, suitable substituents include one or more groups selected from halo, cyano, nitro, $C_{1-6}$ alkyl, $C_{1-6}$ alkoxy and methylenedioxy, each optionally substituted by one to five halos or the substituent is a group $S(O)_nR^{7a}$ wherein n is 0, 1 or 2 and $R^{7a}$ is $C_{1-6}$ alkyl optionally substituted by halo or $R^{7a}$ is amino.

Preferably $Q^a$ is substituted phenyl or naphthyl.

Suitably $R^{2a}, R^{3a}, R^{4a}$ and $R^{5a}$ are chosen from hydrogen, methyl, or fluoro.

Suitably $R^{1a}$ is $C_{1-6}$ alkyl optionally substituted by dioxalanyl, or $R^{1a}$ is $C_{2-5}$ alkenyl. Most suitably $R^{1a}$ is a branched chain $C_{4-6}$ alkyl group, such as isobutyl, 1,2-dimethylpropyl, 1,1,2-trimethyl propyl, 2,2-dimethylpropyl or $R^{1a}$ is 2-methyl-prop-2-enyl or (2-methyl-1,3-dioxalan-2-yl) methyl. Preferably $R^{1a}$ is isobutyl or 2- methylprop-2-enyl where $R^{2a}$ and $R^{3a}$ are hydrogen and $R^{4a}$ is methyl.

One preferred group of compounds of the formula (II) includes those of formula (III):

$$Q^aQ^{1a}CH=CHCR^{4a}=CHCONHR^{1a} \quad (III)$$

wherein $Q^a$, $Q^{1a}$, $R^{4a}$ and $R^{1a}$ are as hereinbefore described.

One preferred group of compounds of the present invention includes those of formula (IV).

$$QQ^1CH=CR^3CR^4=CR^5CXNHR^1 \quad (IV)$$

wherein $Q,Q^1$, and $R^1$ to $R^5$ are as hereinbefore described.

Preferred compounds of the formula (IV) include those wherein Q is substituted phenyl, $Q^1$ is a trans 1,2-cyclopropyl ring, where the 2-position of the cyclopropyl ring is unsubstituted or substitued by fluoro or chloro, $R^4$ is methyl or hydrogen, $R^2$ is hydrogen, $R^3$ and $R^5$ are hydrogen or fluoro and $R^1$ is isobutyl or 1,2-dimethylpropyl or 2-methylprop-2-enyl and X is oxygen or sulphur.

Thus, preferred compounds of the formula (I) include:

(±)-(2E,4E) N-(1,2-Dimethylpropyl)-5-[trans-2-(4-bromophenyl)cyclopropyl]penta-2,4-dienamide (±)-(2E/Z,4E) N-Isobutyl-3-methyl-5-(trans-2-(3,5-bis-trifluoro methylphenyl) cyclopropyl)-2,4-dienamide.

(±)-(2E,4E) N-(1,2-Dimethylpropyl)-5-(trans-2-(3,5-bistrifluoro methylphenyl)cyclopropyl)-2,4-dienamide.

(±)-(2E,4E) N-(1,2-Dimethylpropyl)-5-(trans-2-(3,4-dichloro phenyl) cyclopropyl) -2,4-dienamide.

(±)-(2E,4E) N-Isobutyl-3-methyl-5-(trans-2-(3,4-dichlorophenyl cyclopropyl)-2,4-dienamide.

(±)-(2E,4E) N-(1,2-Dimethylpropyl)-5-(trans-2-(4-chlorophenyl) cyclopropyl)-2,4-dienamide.

(±)-(2E,4E) N-(1,2-Dimethylpropyl)-5-[trans-2-(3,4-dibromophenyl)cyclopropyl]penta-2,4-die namide.

(±)-(2E,4E) N-Isobutyl-3-methyl-5-[trans-2-(3,4-dibromophenyl)cyclopropyl]penta-2,4-dienamide.

(±)-(2E,4E) N-Isobutyl-3-methyl-5-methyl-5-[trans-2-(4-chlorophenyl) cyclopropyl]penta-2,4-dienamide.

(±)-(2E,4E) N-(2-Methylprop-2-enyl)-3-methyl-5-[trans-2-(3,4-dibromophenyl)cyclopropyl ]penta-2,4-dienamide.

(±)-(2E,4E) N-Isobutyl-3-methyl-5-[trans-2-(3-trifluoromethyl-4-chlorophenyl)cyclopropyl]p enta-2,4-dienamide.

(±)-2E,4E) N-Isobutyl-3-methyl-5-[trans-2-(3,5-dichloro-4-bromophenyl) cyclopropyl]penta-2,4-dienamide.

(±)-2E,4E) N-Isobutyl-3-methyl-5-[trans-2-(3,4,5-trichlorophenyl)cyclopropyl]penta-2,4-die namide.

(±)-(2E,4Z) N-Isobutyl-3-methyl-4-fluoro-5-[trans-2-(3,4-dichlorophenyl)cyclopropyl]penta-2,4-dienamide.

(±)-(2E,4E) N-(1,2-Dimethylpropyl)-5-[trans-2-(3-chloro-4-bromophenyl) cyclopropyl]penta-2,4-dienamide.

(±)-(2E,4E) N-Isobutyl-3-methyl-5-[trans-2-(3-chloro-4-bromophenyl)cyclopropyl]penta-2, 4-dienamide.

(±)-(2E,4E) N-(1,2-Dimethylpropyl)-5-[trans-2-(3-bromo-4-chlorophenyl)cyclopropyl]penta-2,4-dienamide.

(±)-(2E,4E) N-(1,2-Dimethylpropyl-5-[r-1-fluoro-c-2-(3,4,5-trichlorophenyl)cyclopropyl]pen ta-2,4-dienamide.

(±)-(2E,4E0 N-Isobutyl-3-methyl-5-[r-1-fluoro-c-2-(3,4,5-trichlorophenyl)cyclopropyl]penta -2,4-dienamide.

(±)-(2Z,4E) N-Isobutyl-2-fluoro-3-methyl-5-[trans-2-(3,4-dichlorophenyl)cyclopropyl]penta-2,4-dienamide.

(±)-(2Z,4E) N-(2-Methylprop-2-enyl)-2-fluoro-3-methyl-5-[trans-2-(3,4-dichloroph enyl)cyclopropyl]penta-2,4-dienamide.

(±)-(2E,4E) N-(sec-Butyl)-5-[trans-2-(3,4-dichlorophenyl)cyclopropyl]penta-2,4-dienamide.

(±)-(2E,4E) N-(1,2-Dimethylpropyl)-5-[r-1-fluoro-c-2-(3,4-dichlorophenyl)cyclopropyl]penta -2,4-dienamide.

(±)-(2E/Z,4E) N-(2-Methylprop-2-enyl)-3-methyl-5-[r-1-fluoro-c-2-(3,4 -dibromoph enyl)cyclopropyl]penta-2,4-dienamide.

(±)-(2E/Z,4E) N-Isobutyl-3-methyl-5-[r-1-fluoro-c-2-(3,4-dibromophenyl)cyclopropyl]penta-2,4-dienamide.

(±)-(2E,4E) N-(1,2-Dimethylpropyl)-5-[r-1-fluoro-c-2-(3,4-dibromophenyl)cyclopropyl]penta-2,4-dienamide.

(±)-(2E/Z,4E) N-Isobutyl-3-methyl-5-[r-1-fluoro-c-2-(3,4-dichlorophenyl)cyclopropyl]penta-2,4-dienamide.

(±)-(2E,4E) N-(1,2-Dimethylpropyl)-5-[r-1-chloro-c-2-(3,4-dichlorophenyl)cyclopropyl]penta-2,4-dienamide.

(±)-(2E,4Z) N-(2-Methylprop-2-enyl)-3-methyl-4-fluoro-5-[trans-2-(3,4-dichlorophenyl) cyclopropyl]penta-2,4-dienamide.

(±)-(2E,4E) N-Isobutyl-3-methyl-5-[r-1-chloro-2-c-(3,4-dichlorophenyl)cyclopropyl]penta-2,4-dienamide.

(±)-(2E/Z,4E) N-(2-Methylprop-2-enyl)-3-methyl-5-[r-1-fluoro-2-c-(3,4-dichloroph enyl)cyclopropyl]penta-2,4-dienamide.

(±)-(2E/Z,4E) N-(2-Methylprop-2-enyl)-3-methyl-5-[r-1-fluoro-2-c-(3,4-5-trichlorophenyl) cyclopropyl]penta-2,4-dienamide.

(±)-(2E,4E) N-(2-Methylprop-2-enyl)-3-methyl-5-[trans-2-(3,4-dibromophenyl)cyclopropyl ]penta-2,4-dienamide.

(±)-(2E,4E) N-(1,2-Dimethylpropyl)-5-[c-2-(3,4-dichlorophenyl)-r-1-fluoro-cyclopropyl]penta-2,4-dienethioamide.

By the term halo is meant fluoro, chloro bromo and iodo. By the term hydrocarbyl group is meant, alkyl, alkenyl. alkynyl, aralkyl including a cyclic alkyl or alkenyl group optionally substituted by alkyl, alkenyl or alkynyl; and alkyl or alkenyl substituted by cyclic alkyl and alkenyl, and phenyl groups.

Salts of the compounds of the present invention will normally be acid addition salts. Such salts may be formed from mineral or organic or cycloalkyl acids. Preferred salts include those formed from hydrochloric, hydrobromic, sulphuric, citric, nitric, tartaric, phosphoric, lactic, benzoic, glutamic, aspartic, pyruvic, acetic, succinic, fumaric, maleic, oxaloacetic, hydroxynaphthoic, isethionic, stearic, methane, sulphonic, ethanesulphonic, benzenesulphonic, toluene-p-sulphonic, lactobionic, glucuronic, thiocyanic, propionic, embonic, naphthenoic and perchloric acids.

The compounds of formula (I) may exist in a number of stereoisomeric forms. The present invention encompasses both individual geometric and stereoisomers and mixtures thereof. The present invention also encompasses compounds of the formula (I) containing radioisotopes, particularly those in which one to three hydrogen atoms are replaced by tritium or one or more carbon atoms are replaced by $^{14}C$.

In a further aspect, the present invention provides a process for the preparation of a compound of the formula (I) as hereinbefore defined which comprises: (cf.Scheme 1)

a) when X is oxygen, the reaction of the corresponding acid or acid derivative $QQ^1CR^2\!\!=\!\!CR^3CR^4\!\!=\!\!CR^5C(\!=\!X)Z^1$ with an amine $H_2NR^1$ wherein $Q,Q^1,R^2, R^3,R^4,R^5$, and $R^1$ are as hereinbefore defined and X is oxygen and $Z^1$ is hydroxy, $C_{1-6}$ alkoxy, halo or a phosphoroimidate ester (—P(O)-(O-aryl)NH— aryl where aryl is $C_{6-10}$ aryl)

b) the formation of the $CR^2\!\!=\!\!CR^3CR^4\!\!=\!\!CR^5C(\!=\!X)NHR^1$ moiety through a Wittig type reaction. and optionally thereafter converting one compound of the formula (I) into another compound of the formula (I) by methods well known to those skilled in the art.

Process (a) is normally carried out at a non-extreme temperature, for example between −25° C. and 150° C. in an anhydrous aprotic solvent, such as ether, dichloromethane, toluene or benzene. The precise conditions will be dependent on the nature of the group $Z^1$, for example when $Z^1$ is alkoxy the reaction is conveniently carried out at an elevated temperature, i.e. 50° C. to 125° C., and conveniently at reflux, preferably in the presence of a trialkylaluminium compound, such as trimethylaluminium, which forms a complex with the amine $H_2NR^1$. When $Z^1$ is halo or phosphoroimidate the reaction is conveniently carried out at 0° C. to 30° C. and suitably at room temperature preferably in the presence of a tertiary amine, such as triethylamine.

If the acid derivative is an acid halide for example the acid chloride, then it may be formed from the corresponding acid by reaction with a suitable reagent such as oxalyl chloride or thionyl chloride. When $Z^1$ is a phosphoroimidate group then this is suitably formed from $(PhO)P(\rightarrow O)NHPhCl$ where Ph is phenyl. The acid, or the acid function in the compound $QQ^1CR^2\!\!=\!\!CR^3CR^4\!\!=\!\!CR^5COZ^1$, may be prepared by hydrolysis of the corresponding ester.

The esters may be prepared by a number of alternative routes. for example: (cf.Scheme 2)

(i) a conventional Wittig or Wadsworth-Emmons reaction using for example an aldehyde and ethoxycarbonylmethylene triphenylphosphorane or an anion from triethylphosphonocrotonate or 3-methyl triethylphosphonocrotonate. This latter reaction may result in an isomeric mixture for example a mixture of (Z) and (E) substituted dienoates; such a mixture may be reacted as above, and the resulting mixture of amides separated by chromatography or other convenient techniques. The Wittig type reagent may be produced for example by the following route or a modification thereof:

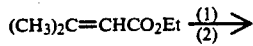

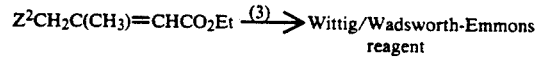

wherein $Z^2=(aryl)_3P$, $(aryl)_2P(O)$ or $(C_{1-4}\ alkoxy)_2P(O)$ where aryl is preferably phenyl and alkoxy is preferably ethoxy.
(1) N-bromo succinimide
(2) e.g. $(EtO)_3P$ or $(Ph)_3P$
(3) This reaction is normally carried out in the presence of a base such as lithium diisopropylamide, butyllithium sodium alkoxide or sodium hydride.

(ii) by rearrangement and elimination of $HS(\rightarrow O)Z^3$ from a compound of formula:

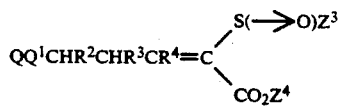

wherein $Q,Q^1,R^2,R^3$ and $R^4$ are as hereinbefore defined, $Z^3$ is any suitable group, eg phenyl, substituted phenyl such as 4-chlorophenyl or $C_{1-4}$ alkyl, for example methyl, $Z^4$ is $C_{1-4}$ alkyl, e.g. methyl or ethyl.

The above compound may be obtained by reaction of a compound $QQ^1CHR^2CHR^3CR^4O$ with a compound $Z^3\ S(O)CH_2CO_2Z^4$.

(iii) By elimination on a compound $QQ^1CHR^2CR^3(OZ^5)CR^4\!\!=\!\!CR^5CO_2Z^4$ wherein $Q,Q^1,R^2,\bar{R}^3,R^4,R^5$ and $Z^4$ are as defined above, and $Z^5$ is hydrogen or $C_{1-4}$ acyl such as acetyl. The reaction is preferably carried out in an aromatic solvent conveniently in the presence of a molybdenum catalyst and a base, such as bis-trimethylsilylacetamide.

The above compound may be obtained by the reaction of a suitable aldehyde with a suitable sulphenyl compound, followed by acylation.

(iv) reaction of a compound of formula $QQ^1CR^2\!\!=\!\!CR^3C(\!=\!O)R^4$ with one of formula $Me_3SiCHR^5CO_2Z^4$, wherein $Q,R^2$ to $R^5$, $Q^1$ and $Z^4$ are as hereinbefore defined.

This process may be carried out in an anhydrous solvent, e.g. tetrahydrofuran in the absence of oxygen, in the presence of a base, e.g. lithium cyclohexylisopropylamide.

(v) by reaction of a compound of formula $QQ^1CR^2\!\!=\!\!CR^3C(OZ^6)\!\!=\!\!CR^5CO_2Z^4$ with a compound of formula $R^4M^1$ wherein $Q,Q^1,R^2,R^3,R^4,R^5$ and $Z^4$ are as hereinbefore defined, $Z^6$ is a suitable group such as dialkylphosphate or trifluoromethanesulphonate and $M^1$ is a metal such as copper (I) or copper (I) associated with lithium or magnesium.

This process can be performed at low temperature in an anhydrous ethereal solvent such as diethyl ether, dimethyl sulphide or tetrahydrofuran in the absence of oxygen.

vi) by reaction of a compound of formula $QQ^1CR^2\!\!=\!\!CR^3M^2$ with one of formula $YCR^4\!\!=\!\!CR^5CO_2Z^4$, wherein $Q,Q^1$, $R^2,R^3,R^4,R^5$ and $Z^4$ are as hereinbefore defined, Y is halo or tin and $M^2$ is a silyl or metal containing group, such as trimethylsilyl or a group containing zirconium, tin, aluminum or zinc, for example a bis(cyclopentadienyl) zirconium chloride group. This process is normally carried out at a nonextreme temperature i.e. between 0° C. and 100° C. and conveniently at room temperature, in a non-aqueous ethereal solvent such as tetrahydrofuran, in the presence of a palladium (O) catalyst, (such as bis (triphenylphosphine)palladium) and under an inert atmosphere of nitrogen or argon.

(vii) by elimination of $Z^3S(\rightarrow O)H$ from a compound of formula

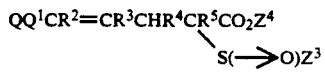

wherein Q, $Q^1$, $R^2$, $R^3$, $R^4$, $R^5$, $Z^3$ and $Z^4$ are as hereinbefore defined.

The above compound may be obtained by reaction of a compound $QQ^1CHR^2CR^3=CHR^4$ with $Z^3S(O)CH_2CO_2Z^4$ Process (b) may be carried out by having an aldehyde or ketone group attached either to the amide/thioamide terminus or to the $QQ^1$ fragment of formula (I) and then reacting this with the appropriate phosphorous ylid. i.e.
$QQ^1(CR^2=CR^3)COR^4 + Z^2CHR^5.C(=X)NHR^1$ or
$QQ^1COR^2 + Z^2CHR^3.CR^4=CR^5.C(=X)NHR^1$ or
$QQ^1(CR^2=CR^3)CHR^5Z^2 + R^5CO.C(=X)NH.R^1$
wherein Q, $Q^1$, $R^2$, $R^3$, $R^4$, $R^5$, $R^1$, X and $Z^2$ are as hereinbefore defined.

Process (b) is carried out in an anhydrous inert solvent, for example an ether such as tetrahydrofuran, optionally in the presence of a base for example an amine derived from the preparation of the phophorous ylid, i.e. isopropylamine, and preferably in the absence of oxygen, e.g. under a nitrogen atmosphere, at a low temperature ($-60°$ C. to $20°$ C.). The phosphorous ylid may be obtained from its precursor as described above by reaction with a base such as lithium diisopropylamide, butyllithium, sodium alkoxide or sodium hydride. Compounds of the formula (I) wherein X is sulphur are preferably prepared by process (b) when $Z^2$ is a group $(C_{1-4}$ alkoxy$)_2P=$). The aldehyde intermediates $QQ^1CR^2=O$ may be prepared by acid hydrolysis of a ketal, enol ether or acetal in a solvent such as acetone-water or by oxidation of the appropriate alcohols using for example pyridinium chlorochromate, pyridinium dichromate or oxalyl chloride-dimethyl sulphoxide in a solvent such as dichloromethane. The aldehydes may also be prepared by reduction of the appropriate nitriles with a reagent such as diisobutylaluminium hydride in hexane.

The alcohols (Scheme 3) may be prepared by a) Reaction of $QCH=CX^2OH$ with $(Z^7)_2M^2$ and $CH_2X^3_2$ where $X^2$ is a group such as hydrogen, fluoro, chloro or methyl $X^3$ is a halogen such as iodine, $Z^7$ is $C_{1-4}$ alkyl group such as ethyl and $M^2$ a metal such as zinc, in an inert solvent such as hexane or dichloromethane at moderate temperature ($-20°$ to $+20°$) and $CH_2$ and $CH=CX^2$ combine to form $Q^1$.

b) Reaction of $QCH=CX^2CH_2OH$ with $CX^4_2X^5CO_2M^3$ where $X^4$ and $X^5$ are halogens such as fluorine and chlorine and $M^3$ is an alkali metal such as sodium in an inert solvent such as diglyme at moderate/elevated temperatures ($150°$-$200°$) and $CX^4_2$ and $CH=CX^2$ combine to form $Q^1$.

The intermediate alcohols may be prepared by reduction of the ester $QCH=CX^2CO_2Z^4$ with for instance diisobutylaluminium hydride in an inert solvent such as dichloromethane or tetrahydrofuran at moderate temperature ($-20°$ to $25°$).

c) Reduction of an ester $QQ^1CO_2Z^4$, or of the appropriate carboxylic acid with for instance diisobutylaluminium hydride or diborane in an inert solvent such as dichloromethane or tetrahydrofuran at moderate temperature ($-20°$ to $25°$). The esters may be prepared by reaction of a diazoacetate $N_2CH.CO_2Z^4$ with a compound $QCH=CH_2$ in the presence of a copper containing catalyst such as copper sulphate where CH and $CH=CH_2$ combine to form $Q^1$. The esters may also be prepared by the reaction of $QCH=CHCO_2Z^4$ with an anion derived from $Me_2S(O)_mC(Z^7)_2$ where $Z^7$ is hydrogen or $C_{1-6}$ alkyl and m is 1 or 2.

The attached reaction schemes assist in illustrating the preparation of the intermediates and their conversion to compounds of formula (I). The intermediates of the present invention form a further aspect of the present invention and may be prepared where appropriate by standard methods other than those described.

The compounds of formula (I) may be used to control pests such as arthropods e.g. insect and acarine pests, and helminths, i.e. nematodes. Thus, the present invention provides a method for the control of arthropods and/or helminths which comprises administering to the arthropod and/or helminth or to their environment an arthropodically effective amount of a compound of the formula (I). The present invention also provides a method for the control and/or eradication of arthropod and/or helminth infestations of animals (including humans) and/or of plants,(including trees) and/or stored products which comprises administering to the animal or locus an effective amount of a compound of the formula (I). The present invention further provides for the compounds of the formula (I) for use in human and veterinary medicine in public health control and in agriculture for the control of arthropod and/or helminth pests.

The compounds of formula (I) are of particular value in the protection of field, forage, plantation, glasshouse, orchard and vineyard crops of ornamentals and of plantation and forest trees, for example cereals (such as maize, wheat, rice, sorghum), cotton, tobacco, vegetables and salads (such as beans, cole crops, curcurbits, lettuce, onions, tomatoes and peppers), field crops (such as potato, sugar beet, ground nuts, soyabean, oil seed rape) sugar cane, grassland and forage (such as maize, sorghum, lucerne), plantations (such as of tea, coffee, cocoa, banana, oil palm, coconut, rubber, spices), orchards and groves (such as of stone and pip fruit, citrus, kiwifruit. avocado, mango, olives and walnuts), vineyards, ornamental plants, flowers and shrubs under glass and in gardens and parks, forest trees (both deciduous and evergreen) in forests, plantations and nurseries.

They are also valuable in the protection of timber (standing, felled, converted, stored or structural) from attack by sawflies (e.g Urocerus) or beetles (e.g. scolytids, platypodids, lyctids, bostrychids, cerambycids, anobiids).

They have applications in the protection of stored products such as grains, fruits, nuts, spices and tobacco, whether whole, milled or compounded into products, from moth, beetle and mite attack. Also protected are stored animal products such as skins, hair, wool and feathers in natural or converted form (e.g. as carpets or textiles) from moth and beetle attack; also stored meat and fish from beetle, mite and fly attack.

The compounds of general formula (I) are of particular value in the control of arthropods or helminths which are injurious to, or spread or act as vectors of diseases in man and domestic animals, for example those hereinbefore mentioned, and more especially in the control of ticks, mites, lice, fleas, midges and biting, nuisance and myiasis flies.

The compounds of Formula (I) may be used for such purposes by application of the compounds themselves or in diluted form in known fashion as a dip, spray, fog, lacquer, foam, dust, powder, aqueous suspension, paste, gel cream, shampoo, grease, combustible solid, vapourising mat, combustible coil, bait, dietary supplement, wettable powder, granule, aerosol, emulsifiable concentrate, oil suspensions, oil solutions, pressure-pack, impregnated article, pour on formulation or other standard formulations well known to those skilled in the art. Dip concentrates are not applied per se, but diluted with water and the animals immersed in a dipping bath containing the dip wash. Sprays may be applied by hand or by means of a spray race or arch. The animal, soil, plant or surface being treated may be saturated with the spray by means of high volume application or superficially coated with the spray by means of light or ultra low volume application Aqueous suspensions may be applied in the same manner as sprays or dips. Dusts may be distributed by means of a powder applicator or in the case of animals, incorporated in perforated bags attached to trees or rubbing bars. Pastes, shampoos and greases may be applied manually or distributed over the surface of an inert material such as that against which animals rub and transfer the material to their skins. Pour-on formulations are dispensed as a unit of liquid of small volume on to the backs of animals such that all or most of the liquid is retained on the animals.

The compounds of Formula (I) may be prepared either as formulations ready for use on the animals, plants or surface or as formulations requiring dilution prior to application, but both types of formulation comprise a compound of Formula (I) in intimate admixture with one or more carriers or diluents. The carriers may be liquid, solid or gaseous or comprise mixtures of such substances, and the compound of Formula (I) may be present in a concentration of from 0.025 to 99% w/v depending upon whether the formulation requires further dilution.

Dusts, powders and granules and other solid formulations comprise the compound of Formula (I) in intimate admixture with a powdered solid inert carrier for example suitable clays, kaolin, bentonite, attapulgite, adsorbent carbon black, talc, mica, chalk, gypsum, tricalcium phosphate, powdered cork, magnesium siliate, vegetable carriers, starch and diatomaceous earths. Such solid formulations are generally prepared by impregnating the solid diluents with solutions of the compound of formula (I) in volatile solvents, evaporating the solvents and, if desired grinding the products so as to obtain powders and, if desired, granulating, compacting or encapsulating the products.

Sprays of a compound of Formula (I) may comprise a solution in an organic solvent (e.g. those listed below) or an emulsion in water (dip wash or spray wash) prepared in the field from an emulsifiable concentrate (otherwise known as a water miscible oil) which may also be used for dipping purposes. The concentrate preferably comprises a mixture of the active ingredient with or without an organic solvent and one or more emulsifiers. Solvents may be present within wide limits but preferably in an amount of from 0 to 90% w/v of the composition and may be selected from kerosene, ketones, alcohols xylene aromatic naphtha, and other solvents known in the formulating art. The concentration of emulsifiers may be varied within wide limits but is preferably in the range of 5 to 25% w/v and the emulsifiers are conveniently non-ionic surface active agents including polyoxyalkylene esters of alkyl phenols and polyoxyethylene derivatives of hexitol anhydrides and anionic surface active agents including Na lauryl sulphate, fatty alcohol ether sulphates, Na and Ca salts of alkyl aryl sulphonates and alkyl sulphosuccinates. Cationic emulsifiers include benzalkonium chloride and quaternary ammonium ethosuphates.

Amphoteric emulsifiers include carboxymethylated oleic imidazoline and alkyl dimethyl betain.

Vaporising mats normally comprise cotton and cellulose mix compressed into a board of approximately $35 \times 22 \times 3$ mm dimensions, treated with up to 0.3 ml of concentrate comprising the active ingredient in an organic solvent and optionally an antioxidant, dye and perfume. The insecticide is vaporised using a heat source such as an electrically operated mat heater.

Combustible solids normally comprise of wood powder and binder mixed with the active ingredient and formed into shaped (usually coiled) strips. Dye and fungicide may also be added. Wettable powders comprise an inert solid carrier, one or more surface active agents, and optionally stabilisers and/or anti-oxidants.

Emulsifiable concentrates comprise emulsifying agents, and often an organic solvent, such as kerosene, ketones, alcohols, xylenes, aromatic naphtha, and other solvents known in the art.

Wettable powders and emulsifiable concentrates will normally contain from 5 to 95% by weight of the active ingredient, and are diluted, for example with water, before use.

Lacquers comprise a solution of the active ingredient in an organic solvent, together with a resin. and optionally a plasticiser.

Dip washes may be prepared not only from emulsifiable concentrates but also from wettable powders, soap based dips and aqueous suspensions comprising a compound of Formula (I) in intimate admixture with a dispersing agent and one or more surface active agents.

Aqueous suspensions of a compound of Formula (I) may comprise a suspension in water together with suspending, stabilizing or other agents. The suspensions or solutions may be applied per se or in a diluted form in known fashion.

Greases (or ointments) may be prepared from vegetable oils, synthetic esters of fatty acids or wool fat together with an inert base such as soft paraffin. A compound of Formula (I) is preferably distributed uniformly through the mixture in solution or suspension. Greases may also be made from emulsifiable concentrates by diluting them with an ointment base.

Pastes and shampoos are also semi-solid preparations in which a compound of Formula (I) may be present as an uniform dispersion in a suitable base such as soft or liquid paraffin or made on a non-greasy basis with glycerin mucilage or a suitable soap. As greases, shampoos and pastes are usually applied without further dilution they should contain the appropriate percentage of the compound of Formula (I) required for treatment.

Aerosol sprays may be prepared as a simple solution of the active ingredient in the aerosol propellant and co-solvent such as halogenated alkanes and the solvents referred to above, respectively. Pour-on formulations may be made as a solution or suspension of a compound of Formula (I) in a liquid medium. An avian or mammal host may also be protected against infestation of acarine ectoparasites by means of carrying a suitably-moulded shaped plastics article impregnated with a compound of Formula (I). Such articles include impregnated collars, tags, bands, sheets and strips suitably attached to appropriate parts of the body. Suitably the plastics material is a polyvinyl chloride (PVC).

The concentration of the compound of Formula (I) to be applied to an animal, premisés or outdoor areas will vary according to the compound chosen, the interval between treatments, the nature of the formulation and the likely infestation, but in general 0.001 to 20.0% w/v and preferably 0.01 to 10% of the compound should be present in the applied formulation. The amount of the compound deposited on an animal will vary according to the method of application, size of the animal, concentration of the compound in the applied formulation, factor by which the formulation is diluted and the nature of the formulation but in general will lie in the range of from 0.0001% to 0.5% w/w except for undiluted formulations such as pour-on formulations which in general will be deposited at a concentration in the range from 0.1 to 20.0% and preferably 0.1 to 10%. The amount of compound to be applied to stored products in general will lie in the range of from 0.1 to 20 ppm. Space sprays may be applied to give an average initial concentration of 0.001 to 1 mg of compound of formula (I) per cubic meter of treated space.

The compounds of formula (I) are also of use in the protection and treatment of plant species, in which case an effective insecticidal, acaricidal or nematocidal amount of the active ingredient is applied. The application rate will vary according to the compound chosen, the nature of the formulation, the mode of application, the plant species, the planting density and likely infestation and other like factors but in general, a suitable use rate for agricultural crops is in the range 0.001 to 3 kg/Ha and preferably between 0.01 and 1 kg/Ha. Typical formulations for agricultural use contain between 0.0001% and 50% of a compound of formula (I) and conveniently between 0.1 and 15% by weight of a compound of the formula (I).

Dusts, greases. pastes and aerosol formulations are usually applied in a random fashion as described above and concentrations of 0.001 to 20% w/v of a compound of Formula (I) in the applied formulation may be used.

The compounds of formula (I) have been found to have activity against the common housefly (*Musca domestica*). In addition. certain compounds of formula (I) have activity against other arthropod pests including *Myzus persicae, Tetranychus urticae, Plutella xylostella,* Culex spp. *Tribolium castaneum, Sitophilus granarius, Periplaneta ameircana* and *Blattella germanica.* The compounds of formula (I) are thus useful in the control of arthropods e.g. insects and acarines in any environment where these constitute pests, e.g. in agriculture, in animal husbandry, in public health control and in domestic situations.

Insect pests include members of the orders Coleoptera (e.g. Anobium,Ceutorhynchus,Rhynchophorus, Cosmopolites, Lissorhoptrus, Meligethes, Hypothenemus, Hylesinus, Acalymma, Lema, Psylliodes, Leptinotarsa, Gonocephalum, Agriotes, Dermolepida, Heteronychus, Phaedon, Tribolium, Sitophilus, Diabrotica, Anthonomus or Anthrenus spp.), Lepidoptera (e.g. Ephestia, Mamestra, Earias, Pectinophora, Ostrinia, Trichoplusia, Pieris, Laphyzma, Agrotis, Amathes, Wiseana, Tryporysa, Diatraea, Sporganothis, Cydia, Archips, Plutella, Chilo, Heliothis, Spodoptera or Tineola spp.), Diptera (e.g. Musca, Aedes, Anopheles, Culex, Glossina, Simulium, Stomoxys, Haematobia, Tabanus, Hydrotaea, Lucilia, Chrysomia, Callitroga, Dermatobia, Gasterophilus, Hypoderma, Hylemyia, Atherigona, Chlorops, Phytomyza, Ceratitis, Liriomyza and Melophagus spp.), Phthiraptera (Malophaza e.g. Damalina spp. and Anoplura e.g. Linohnathus and Haematopinus spp.), Hemiptera (e.g. Aphis, Bemisia,- Phorodon, Aeneolamia, Empoasca, Parkinsiella, Pyrilla, Aonidiella, Coccus, Pseudococus, Helopeltis, Lygus, Dysdercus, Oxycarenus, Nezara, Aleurodes, Triatoma, Psylla, Mysus, Megoura, Phylloxera, Adelyes, Niloparvata, Nephrotetix or Cimex spp.), Orthoptera (e.g. Locusta, Gryllus, Schistocerca or Acheta spp.), Dictyoptera (e.g. Blattella, Periplaneta or Blatta spp.), Hymenoptera (e.g. Athalia, Cephus, Atta, Solenopsis or Monomorium spp.), Isoptera (e.g. Odontotermes and Reticulitermes spp.), Siphonaptera (e.g. Ctenocephalides or Pulex spp.), Thysanura (e.g. Lepisma spp.), Dermaptera (e.g. Forficula spp.), Pscoptera (e.g. Peripsocus spp.) and Thysanoptera (e.g. *Thrips tabaci*),.

Acarine pests include ticks, e.g. members of the genera Boophilus,Ornithodorus, Rhipicephalus, Amblyomma, Hyalomma, Ixodes, Haemaphysalis, Dermacentor and Anocentor, and mites and manges such as Acarus, Tetranychus, Psoroptes, Notoednes, Sarcoptes, Psorergates, Chorioptes, Eutrombicula, Demodex, Panonychus, Bryobia, Eriophyes, Blaniulus, Polynhagotarsonemus, Scutigerella, and Oniscus spp.

Nematodes which attack plants and trees of importance to agriculture,. forestry, horticulture either directly or by spreading bacterial, viral, mycoplasma or, fungal diseases of the plants, include root-knot nematodes such as Meloidogyne spp. (e.g. *M. incognita*); cyst nematodes such as Globodera spp. (e.g. *G. rostochiensis*); Heterodera spp. (e. g. *hydrogen. .avenae*): Radopholus spp. (e.g. *R. similis*); lesion nematodes such as Pratylenchus spp. (e.g. *P. pratensis*); Belonolaimus spp. (e.g. *B. gracilis*); Tylenchulus spp. (e.g. *T. semipenetrans*); Rotylenchulus spp. (e.g.*R. reniformis*); Rotylenchus spp. (e.g. *R. robustus*); Helicotylenchus spp. (e.g. *hydrogen. multicinctus*);Hemicycliophora spp. (e.g. *hydrogen. gracilis*); Criconemoides spp. (e.g. *C. similis*); Trichodorus spp. (e g. *T. primitivus*): dagger nematodes such as Xiphinema spp. (e.g. *X. diversicaudatum*), Longidorus spp (e.g. *L. elongatus*); Hoplolaimus spp. (e.g. *hydrogen. coronatus*); Aphelenchoides spp. (e g *A. ritzema-bosi, A. besseyi*): stem and bulb eelworms such as Ditylenchus spp. (e.g. *D. dipsaci*).

Compounds of the invention may be combined with one or more other pesticidally active ingredients (for example pyrethroids, carbamates and organophosphates) and/or with attractants, repellents, bacteriocides, fungicides nematocides, anthelmintics and the like. Furthermore, it has been found that the activity of the compounds of the invention may be enhanced by the addition of a synergist or potentiator, for example: one of the oxidase inhibitor class of synergists, such as piperonyl butoxide or propyl 2-propynylphenylphosphonate; a second compound of the invention, or a pyrethroid pesticidal compound. When an oxidase inhibitor synergist is present in a formula of the invention. the ratio of synergist to compound of Formula (I) will be in the range 25:1–1:25 e.g. about 10:1.

Stabilisers for preventing any chemical degradation which may occur with the compounds of the invention include, for example, antioxidants (such as tocopherols, butylhydroxyanisole and butylhydroxytoluene) and scavengers (such as epichlorhydrin) and organic or inorganic bases e.g. trialkylamines such as triethylamine which can act as basic stabilises and as scavengers.

INDUSTRIAL APPLICABILITY

Compounds of the present invention show activity as pesticides.

The following examples illustrate, in a non-limiting maner, preferred aspects of the invention.

|     | Formulations |       |
| --- | --- | --- |
| 1.  | Emulsifiable Concentrate | |
|     | Compound of formula (I) | 10.00 |
|     | Alkyl phenol ethoxylate* | 7.50 |
|     | Alkyl aryl sulphonate* | 2.50 |
|     | $C_{8-13}$ aromatic solvent | 80.00 |
|     |  | 100.00 |
| 2.  | Emulsifiable Concentrate | |
|     | Compound of formula (I) | 10.00 |
|     | Alkyl phenol ethoxylate* | 2.50 |
|     | Alkyl aryl sulphonate* | 2.50 |
|     | Ketonic solvent | 64.00 |
|     | $C_{8-13}$ aromatic solvent | 18.00 |
|     | Antioxidant | 3.00 |
|     |  | 100.00 |
| 3.  | Wettable Powder | |
|     | Compound of formula (I) | 5.00 |
|     | $C_{8-13}$ aromatic solvent | 7.00 |
|     | $C_{18}$ aromatic solvent | 28.00 |
|     | China clay | 10.00 |
|     | Alkyl aryl sulphonate* | 1.00 |
|     | Napthalene sulphonic acid* | 3.00 |
|     | Diatomaceous earth | 46.00 |
|     |  | 100.00 |
| 4.  | Dust | |
|     | Compound of formula (I) | 0.50 |
|     | Talc | 99.50 |
|     |  | 100.00 |
| 5.  | Bait | |
|     | Compound of formula (I) | 0.5 |
|     | Sugar | 79.5 |
|     | Paraffin wax | 20.0 |
|     |  | 100.00 |
| 6.  | Emulsion Concentrate | |
|     | Compound of formula (I) | 5.00 |
|     | $C_{8-13}$ aromatic solvent | 32.00 |
|     | Cetyl alcohol | 3.00 |
|     | Polyoxyethylene glycerol monooleate* | 0.75 |
|     | Polyoxyethylene sorbitan esters* | 0.25 |
|     | Silicone solution | 0.1 |
|     | Water | 58.9 |
|     |  | 100.00 |
| 7.  | Suspension Concentrate | |
|     | Compound of formula (I) | 10.00 |
|     | Alkyl aryl ethoxylate* | 3.00 |
|     | Silicone solution | 0.1 |
|     | Alkane diol | 5.0 |
|     | Fumed silica | 0.50 |
|     | Xanthan gum | 0.20 |
|     | Water | 80.0 |
|     | Buffering agent | 1.2 |
|     |  | 100.00 |
| 8.  | Microemulsion | |
|     | Compound of formula (I) | 10.00 |
|     | Polyoxyethylene glycerol monooleate* | 10.00 |
|     | Alkane diol | 4.00 |
|     | Water | 76.00 |
|     |  | 100.00 |
| 9.  | Water Dispersible Granules | |
|     | Compound of formula (I) | 70.00 |
|     | Polyvinyl pyrrolidine | 2.50 |
|     | Alkyl aryl ethoxylate | 1.25 |
|     | Alkyl aryl sulphonate | 1.25 |
|     | China clay | 25.00 |
|     |  | 100.00 |
| 10. | Granules | |

|     | Formulations |       |
| --- | --- | --- |
|     | Compound of formula (I) | 2.00 |
|     | Alkyl phenol ethoxylate* | 5.00 |
|     | Alkyl aryl sulphonate* | 3.00 |
|     | $C_{8-13}$ aromatic solvent | 20.00 |
|     | Kieselguhr granules | 70.00 |
|     |  | 100.00 |
| 11. | Aerosol (pressure pack) | |
|     | Compound of formula (I) | 0.3 |
|     | Piperonyl butoxide | 1.5 |
|     | $C_{8-13}$ saturated hydrocarbon solvent | 58.2 |
|     | Butane | 40.0 |
|     |  | 100.00 |
| 12. | Aerosol (pressure pack) | |
|     | Compound of formula (I) | 0.3 |
|     | $C_{8-13}$ saturated hydrocarbon solvent | 10.0 |
|     | Sorbitan monooleate* | 1.0 |
|     | Water | 40.0 |
|     | Butane | 48.7 |
|     |  | 100.00 |
| 13. | Aerosol (pressure pack) | |
|     | Compound of formula (I) | 1.00 |
|     | $CO_2$ | 3.00 |
|     | Polyoxyethylene glycerol monooleate* | 1.40 |
|     | Propanone | 38.00 |
|     | Water | 56.60 |
|     |  | 100.00 |
| 14. | Lacquer | |
|     | Compound of formula (I) | 2.50 |
|     | Resin | 5.00 |
|     | Antioxidant | 0.50 |
|     | High aromatic white spirit | 92.0 |
|     |  | 100.00 |
| 15. | Spray (ready to use) | |
|     | Compound of formula (I) | 0.10 |
|     | Antioxidant | 0.10 |
|     | Odourless kerosene | 99.8 |
|     |  | 100.00 |
| 16. | Potentiated Spray (ready to use) | |
|     | Compound of formula (I) | 0.10 |
|     | Piperonyl butoxide | 0.50 |
|     | Antioxidant | 0.10 |
|     | Odourless kerosene | 99.30 |
|     |  | 100.00 |
| 17. | Microencapsulated | |
|     | Compound of formula (I) | 10.0 |
|     | $C_{8-13}$ aromatic solvent | 10.0 |
|     | Aromatic di-isocyanate# | 4.5 |
|     | Alkyl phenol ethoxylate* | 6.0 |
|     | Alkyl diamine# | 1.0 |
|     | Diethylene triamine | 1.0 |
|     | Concentrated hydrochloric acid | 2.2 |
|     | Xanthan gum | 0.2 |
|     | Fumed silica | 0.5 |
|     | Water | 64.6 |
|     |  | 100.00 |

*Surfactant
react to form the polyurea walls of the microcapsule
Antioxidant could be any of the following individually or combined
Butylated hydroxytoluene
Butylated hydroxyanisole
Vitamin C (ascorbic acid)

The following Examples illustrate, in a non-limiting manner, preferred aspects of the invention.

EXPERIMENTAL

General Synthetic Methods and Procedures

Various compounds were synthesised and characterised in accordance with the following experimental procedures.

$^1$H N.m.r. spectra were obtained on a Bruker AM-250 spectrometer in deuterochloroform solutions with tetramethylsilane as internal standard and are expressed as ppm from TMS, number of protons, number of peaks, coupling constant J Hz.

Progress of reactions could also be conveniently monitored on Aluminium sheets (40×80 mm) precoated with 0.25 mm layers of silica gel with fluorescent indicator and developed in appropriate solvent or solvent mixture. Temperatures are in degrees Celsius throughout.

Conventional work up was performed as follows:

The reaction mixture was partitioned between an organic solvent and water. The phases were separated and the organic phase washed with at least an equivalent volume of dilute aqueous base as appropriate, and then with a saturated brine wash. The organic phase was then dried over a drying agent, suitably magnesium sulphate and filtered. The volatile solvents were removed and the resulting product subjected to the appropriate purification and used in the next stage of synthesis or analysed as the final product.

The aldehyde, cinnamic acid and amine starting materials were obtained from Aldrich, BDH, Fluorochem Fluka or Lancaster Synthesis with the exception of the following whose preparation is described below.

a) 4-Trifluoromethoxybenzoic acid (5 g) (ex Fluorochem) in Ethanol (100 ml) was treated with concentrated sulphuric acid (1 ml). After hours at reflux, the mixture was concentrated in vacuo and the residue worked up in the usual manner to give ethyl-4-trifluoromethoxy benzoate (5 g). NMR $^1$H: 8.90(2H,d), 7.22(2H,d), 4.37(2H,q), 1.40(3H,t).

The above ester (5 g) in dichloromethane (40 ml) under nitrogen at $-20°$, was treated with diisobutylaluminium hydride (43 ml). After 18 hours at 25°, dilute hydrochloric acid was added and the mixture worked up in the usual manner to give 4-trifluoromethoxy benzyl alcohol (4.1 g). NMR $^1$H: 7.24(2H,d), 7.15(2H,d), 4.52(2H,s), 3.37(3H,s).

The above alcohol was oxidised using the conditions of Swern (oxalyl chloride, 2.05 ml; dimethyl sulphoxide, 3.33 ml and triethylamine, 14.8 ml) in dichloromethane to give 4-trifluoromethoxy benzaldehyde (4 g). NMR $^1$H: 10.04(2H,s), 7.98(2H,d), 7.35(2H,d).

b) 4-Bromo-2-fluorotoluene (ex Fluorochem) in glacial acetic acid (88 ml) and acetic anhydride (89.7 g) was cooled to $-10°$. Sulphuric acid (11.7 g) was added dropwise keeping the reaction temperature lower than $-5°$. Chromium trioxide (14.7 g) was added portionwise at 0°, the mixture was poured onto ice (300 g) and worked up as usual to give diacetoxymethyl-2-fluoro-4-bromobenzene.

The above diacetate in Ethanol (30 ml) and water (30 ml) was treated with concentrated sulphuric acid (3 ml). After hours at reflux the solution was concentrated and the residue worked up in the usual manner to give 2-fluoro-4-bromobenzaldehyde (4.89 g) NMR$^1$ $^1$H: 10.3(1H,s), 7.5(3H,m).

c) 4-Bromo-3-fluorobenzaldehyde was prepared in an analogous manner.

d) To a suspension of 4-chloro-3-trifluoromethylaniline (ex Fluorochem) (15.9 g) in water (16 ml) was added concentrated hydrochloric acid (18 ml) Ice (30 g) was added and the mixture cooled to 0° and treated with sodium nitrite (5.6 g) in water (8 ml). After 15 minutes the mixture was made neutral to congo red with sodium acetate (8 g) in water (10 ml). A solution of formaldoxime, prepared from formaldoxime hydrochloride (ex Lancaster) (9.9 g) and sodium acetate (12 g) (ex BDH) in water (57 ml), at 10° was treated with cupric sulphate (2 g) (ex BDH) and sodium sulphite (0.34 g) followed by sodium acetate (55 g) in water (60 ml). The previously prepared mixture (from the aniline) was added dropwise at 10°–15°. After one hour at 15° hydrochloric acid (77 ml) was added and the mixture worked up in the usual manner. Purification by distillation (80°, 0.5 mmHg) gave 4-chloro-3-trifluoromethylbenzaldehyde (1.5 g).

e) To naphthoic acid (50 g) (ex Aldrich) in glacial acetic acid at reflux was added a few drops of bromine (ex BDH) followed by iodine (0.5 g) (ex (BDH). Bromine (15 ml) was added dropwise over one hour. The mixture was cooled to 25° and stirred there for 18 hours. The resulting white precipitate was filtered, dissolved in hot water and treated with concentrated hydrochloric acid. The precipitate was filtered and dried (over phosphorus pentoxide (ex BDH) to give 5-bromo-2-napthoic acid (recrystallised from ethanol) (28 g). Melting point 261°–2°. NMR $^1$H:(DMSO,CDCl$_3$), 8.60(1H,s), 8.00(5H,m), 7.40(1H,m).

The above acid (34 g) was treated with concentrated sulphuric acid (0.5 ml) in ethanol (240 ml) at reflux for 6 hours. Work up in the conventional manner gave Ethyl-5-bromo-2-naphthoate (23 g). Melting point: 52°–54° NMR $^1$H: 8.68(1H,s), 7.80–8.35(4H,m), 7.43(1H,dd), 4.50(2H,q), 1.48(3H,t).

EXAMPLE 1

(±)-(2E,4E) N-(1,2-Dimethylpropyl)-5-trans-2-(4-bromophenyl) cyclopropyl]penta-2,4-dienamide (compound 1)

(i) 4-Bromobenzaldehyde (9.25 g) was dissolved in dry dichloromethane (250 ml) at 25° C. under nitrogen. Carbomethoxymethylene triphenylphosphorane (17.4 g) (ex Lancaster) was added and the solution stirred at 25° C. for 18 hours. The solvent was removed under vacuum. The residue was washed with hexane and filtered. Removal of the hexane under vacuum gave ethyl 4-bromocinnamate (12.12 g). NMR $^1$H; 7.35 (5H,m), 6.38 (1H,d), 4.1(2H,q), 1.35(3H,t).

(ii) Ethyl 4-bromocinnamate (12.12 g) was dissolved in dry dichloromethane (50 ml) under nitrogen and cooled to $-20°$. Diisobutylaluminium hydride (100 ml, 1M solution in dichloromethane) (ex Aldrich) was added dropwise. The solution was allowed to warm to 25° then stirred for 18 hours then partitioned between ether and dilute hydrochloric acid. The organic phase was washed with saturated sodium bicarbonate, brine, dried over magnesium sulphate and concentrated under vacuum to give 3-(4-bromophenyl)prop-2-en-1-ol (8.9 g). NMR $^1$H: 7.28(2H,d), 7.05 (2H,d), 6.45 (1H,d), 6.25 (1H,t), 4.25 (2H,d), 2.0 (1H,s).

(iii) The above alcohol (1.07 g) was suspended in hexane (50 ml) at room temperature and cooled to $-20°$ C. under nitrogen Diethyl zinc (ex Aldrich) (22.7 ml of a 1.1M solution in hexane) was added dropwise, followed by diiodomethane (ex Aldrich) (4.1 ml). The mixture was allowed to warm to 25° slowly, then stirred for 18 hours. Saturated ammonium chloride was added and the mixture extracted with ether. The combined ethereal extracts were washed with saturated sodium thiosulphate solution dried over magnesium sulphate and the solvents removed under vacuum. Purification by chromatography (silica, ether/hexane) gave (±)-trans-2-(4-bromophenyl)-1-hydroxymethyl cyclopropane (0.53 g). NMR $^1$H: 7.38(2H,d), 6.95(2H,d),3.65 (2H,d),1.8 (1H,m), 1.55 (1H,s), 1.44(1H,m), 0.95 (2H,m).

p (iv) Oxalyl chloride (ex Aldrich)(0.22 ml) was dissolved in dichloromethane (3 ml) and cooled to −70° under nitrogen. Dimethylsulphoxide (ex BDH) (0.36 ml) in dichloromethane (1 ml) was added dropwise. After five minutes, the above alcohol (0.53 g) in dichloromethane (4 ml) was added and the suspension stirred at −70° for 30 minutes. Triethylamine (ex Aldrich) (1.6 ml) was added and the mixture allowed to warm to 0° over one hour. Work-up in the conventional manner gave (±)-trans-[2-(4-bromophenyl)cyclopropyl]-methanal which was used directly. NMR $^1$H: 9.4 (1H,d), 7.33 (2H,d), 6.9 (2H,d), 2.54(1H,m), 2.20 (1H,m), 1.0–1.9(2H,m).

(v) A solution of lithium diisopropylamide in dry tetrahydrofuran prepared from n-butyl lithium (ex Aldrich) (1.6 ml) and diisopropyl amine (ex Aldrich) (0.4 ml) was treated at −60° with triethyl 4-phosphonocrotonate (0.58 g) in tetrahydrofuran under nitrogen. After 2 hours at −60° the above aldehyde (0.52 g) was added. After 18 hours at 25° the mixture was partitioned between ether and water and the ethereal fraction worked up as above. Purification by chromatography (silica; ether/hexane) gave (±)-ethyl-5-[trans-2-(4-bromophenyl)cyclopropyl]penta-2,4-dienoate (0.36 g). NMR $^1$H: 7.4 (2H,d), 7.26 (1H,dd), 6.93 (2H,d), 6.28(1H,dd), 5.80 (1H,d), 5.76 (1H,dd), 4.20 (2H,q), 2.05 (1H,m), 1.75 (1H,m), 1.35 (2H,m), 1.30 (3H,t).

(vi) The above ester (0.18 g) in dry toluene. was added at −10° to a complex prepared from trimethylaluminium (ex Aldrich) (0.62 ml of a 2M solution in toluene) and 1,2-dimethylpropylamine (ex Aldrich)(0.055 g in dry toluene). The whole was heated under reflux for three hours, treated with 2N-hydrochloric acid and the organic layer separated and worked up as above. Purification by chromatography (silica ether/hexane) gave the title compound (0.096 g). Tlc (silica,ethyl acetate:hexane, 3:7) Rf 0.25, m:pt 141.9° C.-143.2° C.

Compounds 2–17, 63, 64, 99 and 100 were prepared in an analogous manner, using the aldehyde Wittig reagent and amine as specified:

| Compound No. | Compound Name |
|---|---|
| 2 | (±)-(2E,4E) N-Isobutyl-5-[trans-2-(4-bromophenyl) cyclopropyl]penta-2,4-dienamide. |
| 3 | (±)-(2E,4E) N-(1,2-Dimethylpropyl)-5-[trans-2-(3,5-bistrifluoromethylphenyl) cyclopropyl]penta-2,4-dienamide. |
| 4 | (±)-(2E,4E) N-(1,2-Dimethylpropyl)-5-[trans-2-(2-naphthyl)cyclopropyl]penta-2,4-dienamide. |
| 5 | (±)-(2E,4E) N-Neopentyl-5-[trans-2-(2-naphthyl) cyclopropyl]penta-2,4-dienamide. |
| 6 | (±)-(2E/Z,4E) N-Isobutyl-3-methyl-5-[trans-2-(2-naphthyl)cyclopropyl]penta-2,4-dienamide. |
| 7 | (±)-(2E,4E) N-Neopentyl-5-[trans-2-(4-bromophenyl)cyclopropyl]penta-2,4-dienamide. |
| 8 | (±)-(2E/Z,4E) N-Isobutyl-3-methyl-5-[trans-2-(4-bromophenyl)cyclopropyl]penta-2,4-dienamide. |
| 9 | (±)-(2E/Z,4E) N-Isobutyl-3-methyl-5-[trans-2-(3,5-bistriflurormethylphenyl)cyclopropyl]penta-2,4-dienamide. |
| 10 | (±)-(2E,4E) N-(1,2-Dimethylpropyl)-5-[trans-2-(4-triflurormethylphenyl)-cyclopropyl]-penta-2,4-dienamide. |
| 11 | (±)-(2E,4E) N-Isobutyl-5-[trans-2-(4-trifluoromethylphenyl)cyclopropyl]-3-methyl-penta-2,4-dienamide. |
| 12 | (±)-(2E,4E) N-(1,2-Dimethylpropyl)-5-[trans-2-(4-methoxyphenyl)cyclopropyl]penta-2,4-dienamide. |
| 13 | (±)-(2E,4E) N-1,2-Dimethylpropyl)-5-[trans-2-(4-trifluoromethoxyphenyl)-cyclopropyl]-penta-2,4-dienamide. |
| 14 | (±)-(2E,4E) N-(1,2-Dimethylpropyl)-5-[trans-2-(4-bromo-2-fluorophenyl)cyclopropyl]penta-2,4-dienamide. |
| 15 | (±)-(2E,4E) N-Isobutyl-3-Methyl-5-[trans-2-(2-fluoro-4-bromophenyl)cyclopropyl]penta-2,4-dienamide. |
| 16 | (±)-(2E,4E) N-(1,2-Dimethylpropyl)-5-[trans-2-(4-bromo-3-fluorophenyl)cyclopropyl]penta-2,4-dienamide. |
| 17 | (±)-(2E,4E) N-Isobutyl-3-methyl-5-[trans-2-(4-bromo-3-fluorophenyl)cyclopropyl]penta-2,4-dienamide. |
| 63 | (±)-(2E,4E) N-(1,2-Dimethylpropyl)-5-[trans-2-(4-chloro-3-trifluoromethylphenyl)cyclopropyl]penta-2,4-dienamide. |
| 64 | (±)-(2E,4E) N-Isobutyl-3-methyl-5-[trans-2-(4-chloro-3-trifluoromethylphenyl)cyclopropyl]penta-2,4-dienamide. |
| 99 | (±)-(2E,4E) N-Isobutyl-3-methyl-5-[trans-2-(5-bromo-2-naphthyl)cyclopropyl]penta-2,4-dienamide. |
| 100 | (±)-(2E,4E) N-(2-Methylprop-2-enyl)-3-methyl-5-[trans-2-(5-bromo-2-naphthyl)cyclopropyl]penta-2,4-dienamide. |

| Compound No. | Aldehyde/RCHO where R is | Wittig Reagent | Amine |
|---|---|---|---|
| 2 | 4-BrPh | 1 | Isobutylamine |
| 3 | 3,5-CF$_3$Ph | 1 | 1,2-Dimethylpropylamine |
| 4 | 2-Naphthyl | 1 | 1,2-Dimethylpropylamine |
| 5 | 2-Naphthyl | 1 | Neopentylamine |
| 6 | 2-Naphthyl | 2 | Isobutylamine |
| 7 | 4-BrPh | 1 | Neopentylamine |
| 8 | 4-BrPh | 2 | Isobutylamine |
| 9 | 3,5-CF$_3$Ph | 2 | Isobutylamine |
| 10 | 4-CF$_3$Ph | 1 | 1,2-Dimethylpropylamine |
| 11 | 4-CF$_3$Ph | 2 | Isobutylamine |
| 12 | 4-MeOPh | 1 | 1,2-Dimethylpropylamine |
| 13 | 4-CF$_3$OPh | 1 | 1,2-Dimethylpropylamine |
| 14 | 2-F,4-BrPh | 1 | 1,2-Dimethylpropylamine |
| 15 | 2-F,4-BrPh | 2 | Isobutylamine |
| 16 | 2-Br,3-FPh | 2 | 1,2-Dimethylpropylamine |
| 17 | 4-Br,3-FPh | 2 | Isobutylamine |
| 63 | 4-Cl,3-CF$_3$Ph | 1 | 1,2-Dimethylpropylamine |
| 64 | 4-Cl,3-CF$_3$Ph | 2 | Isobutylamine |
| 99 | 5-Br-2-naphthyl | 2 | Isobutylamine |
| 100 | 5-Br-2-naphthyl | 2 | 2-Methylprop-2-enyl |

Ph = phenyl
Wittig Reagent
1 = triethyl 4-phosphonocrotonate
2 = triethyl 3-methyl-4-phosphonocrotonate

EXAMPLE 2

(±)-(2E,4E,) N-Isobutyl-5-[trans-2-(3-trifluoromethylphenyl)cyclopropyl]penta-2,4-dienamide (compound 18)

(i) m-Trifluoromethyl cinnamic acid (10.4 g) in ethanol (120 ml) was heated at reflux in the presence of sulphuric acid (6 ml) for eight hours. Removal of solvent under vacuum and work up in the conventional manner gave ethyl-m-trifluoromethyl cinnamate (12.1 g).

NMR $^1$H: 7.58(4H,m), 6.4(1H,d), 4.25(2H,1), 1.3(3H,t). ·

(ii to vi) This compound was then converted to the final product by analogy to example 1 steps (ii) to (vi) but using isobutylamine instead of 1,2-dimethylpropylamine.

Compounds 19–43 and 95–98 were prepared in an analogous manner, using the cinnamic acid, Wittig reagent and amine as specified.

| Compound No. | Compound Name |
|---|---|
| 19 | (±)-(2E,4E) N-(1,2-Dimethylpropyl)-5-[trans-2-(3-trifluoromethylphenyl)cyclopropyl]penta-2,4-dienamide. |
| 20 | (±)-(2E/Z,4E) N-Isobutyl-3-methyl-5-[trans-2-(3-trifluoromethylphenyl)cyclopropyl]penta-2,4-dienamide. |
| 21 | (±)-(2E/Z,4E) N-(2-Methylprop-2-enyl)3-methyl-5-[trans-2-(3-trifluoromethylphenyl)cyclopropyl]penta-2,4-dienamide. |
| 22 | (±)-(2E,4E) N-Isobutyl-5-[trans-2(2-chlorophenyl)cyclopropyl]penta-2,4-dienamide. |
| 23 | (±)-(2E,4E) N-(1,2-Dimethylpropyl) 5-[trans-2-(2-chlorophenyl)cyclo-propyl]penta-2,4-dienamide. |
| 24 | (±)-(2E/Z,4E) N-Isobutyl 3-methyl-5-[trans-2-(2-chlorophenyl)cyclopropyl]penta-2,4-dieneamide. |
| 25 | (±)(2E/Z,4E) N-(2-Methylprop-2-enyl)-3-methyl-5-[trans-2-(2-chlorophenyl)cyclopropyl]penta-2,4-dienamide. |
| 26 | (±)-(2E,4E) N-Isobutyl-3-methyl-5-[trans-2-phenyl-cyclopropyl]penta-2,4-dienamide. |
| 27 | (±)-(2E,4E) N-(1,2-Dimethylpropyl)-5-(trans-2-phenylcyclopropyl)penta-2,4-dienamide. |
| 28 | (±)-(2E,4E) N-(1,2-Dimethylpropyl)-5-[trans-2-(3-chlorophenyl)cyclopropyl]penta-2,4-dienamide. |
| 29 | (±)-(2E,4E) N-Isobutyl-3-methyl-5-[trans-2-(3-chlorophenyl)cyclopropyl]penta-2,4-dienamide. |
| 30 | (±)-(2E,4E)-N-Isobutyl 5-[trans-2-(3,4-dichlorophenyl)cyclopropyl]penta-2,4-dienamide. |
| 31 | (±)-(2E/Z,4E) N-Isobutyl-3-methyl-5-[trans-2-(3,4-dichlorophenyl)cyclopropyl]penta-2,4-dienamide. |
| 32 | (±)-(2E,4E) N-(1,2-Dimethylpropyl)-5-[trans-2-(3,4-dichlorophenyl)cyclopropyl]penta-2,4-dienamide. |
| 33 | (±)-(2E,4E) N-(1,2-Dimethylpropyl)-5-[trans-2-(4-chlorophenyl)cyclopropyl]penta-2,4-dienamide. |
| 34 | (±)-(2E/Z,4E) N-Isobutyl-3-methyl-5-[trans-2-(4-chlorophenyl)cyclopropy]penta-2,4-dienamide. |
| 35 | (±)-(2E/Z,4E) N-(2-Methylprop-2-enyl)-3-methyl-5-[trans-2-(3,4-dichlorophenyl)cyclopropyl]penta-2,4-dienamide. |
| 36 | (±)-(2E,4E) N-Cyclopropylmethyl-5-[trans-2-(3,4-dichlorophenyl)cyclopropyl]-3-methyl-penta-2,4-dienamide. |
| 37 | (±)-(2E,4E) N-(2,2-Dimethylpropyl)-3-methyl-5-[trans-2-(3,4-dichlorophenyl)cyclopropyl]-3-methyl-penta-2,4-dienamide. |
| 38 | (±)-(2E,4E) N-(1,1,2-Trimethylpropyl)-5-[trans-2-(3,4-dichlorophenyl)cyclopropyl]penta-2,4-dienamide. |
| 39 | (±)-(2E,4E) N-(2-Butyl)-5-[trans-2-(3,4-dichlorophenyl)-cyclopropyl]penta-2,4-dienamide. |
| 40 | (±)-(2E,4E) N-(2-Methoxy-2-methylpropyl)-5-[trans-2-(3,4-dichlorophenyl)cyclopropyl]penta-2,4-dienamide. |
| 41 | (±)-(2E,4E) N-(2-Methyl-1,3-dioxolan-2-ylmethyl)-5-[trans-2-(3,4-dichlorophenyl)cyclopropyl]penta-2,4-dienamide. |
| 42 | (±)-(2E,4E) N-(Trimethylsilylmethyl)-5-[trans-2-(3,4-dichlorophenyl)cyclopropyl]penta-2,4-dienamide. |
| 43 | (±)-(2E,4E) N-(Cyclopropylmethyl)-5-[trans-2-(3,4-dichlorophenyl)cyclopropyl]penta-2,4-dienamide. |
| 95 | (±)-(2E,4E) N-(2,2-Dimethylpropyl)-5-[trans-2-(3,4-dichlorophenyl)cyclopropyl]penta-2,4-dienamide. |
| 96 | (±)-(2E,4E) N-Cyclohexyl-5-[trans-2-(3,4-dichlorophenyl)cyclopropyl]penta-2,4-dienamide. |
| 97 | (±)-(2E,4E) N-(2-Butyl)-3-methyl-5-[trans-2-(3,4-dichlorophenyl)]penta-2,4-dienamide. |
| 98 | (±)-(2E,4E N-(2-Methyl-1,3-dioxolan-2-ylmethyl)-3-methyl-5-[trans-2-(3,4-dichlorophenyl)cyclopropyl]penta-2,4-dienamide. |

| Compound No. | Cinnamic Acid | Witting Reagent | Amine |
|---|---|---|---|
| 19 | m-trifluoromethyl | 1 | 1,2-dimethylpropylamine |
| 20 | m-trifluoromethyl | 2 | isobutylamine |
| 21 | m-trifluoromethyl | 2 | 2-methylallylamine |
| 22 | 2-chloro | 1 | isobutylamine |
| 23 | 2-chloro | 1 | 1,2-dimethylpropylamine |
| 24 | 2-chloro | 2 | isobutylamine |
| 25 | 2-chloro | 2 | 2-methylallylamine |
| 26 | unsubstituted | 2 | isobutylamine |
| 27 | unsubstituted | 1 | 1,2-dimethylpropylamine |
| 28 | 3-chloro | 1 | 1,2-dimethylpropylamine |
| 29 | 3-chloro | 2 | isobutylamine |
| 30 | 3,4-dichloro | 1 | isobutylamine |
| 31 | 3,4-dichloro | 2 | isobutylamine |
| 32 | 3,4-dichloro | 1 | 1,2-dimethylpropylamine |
| 33 | 4-chloro | 1 | 1,2-dimethylpropylamine |
| 34 | 4-chloro | 2 | isobutylamine |
| 35 | 3,4-dichloro | 2 | 2-methylallypamine |
| 36 | 3,4-dichloro | 2 | cyclopropylmethylamine |
| 37 | 3,4-dichloro | 2 | neopentylamine |
| 38 | 2,4-dichloro | 1 | 1,1,2-trimethylpropylamine |
| 39 | 3,4-dichloro | 1 | sec-butylamine |
| 40 | 3,4-dichloro | 1* | 2-methoxy-2-methylpropylamine |
| 41 | 3,4-dichloro | 1 | 2-methyl-1,3-dioxolan-2-ylmethylamine |
| 42 | 3,4-dichloro | 1 | trimethylsilylmethylamine |
| 43 | 3,4-dichloro | 1 | cyclopropylmethylamine |
| 95 | 3,4-dichloro | 1 | 1,2-dimethylpropylamine |
| 96 | 3,4-dichloro | 1 | cyclohexylamine |
| 97 | 3,4-dichloro | 2 | sec.butylamine |
| 98 | 3,4-dichloro | 2 | 2-aminomethyl-2-methyl-1,3-dioxolane |

*2-Methoxy-2-methylpropylamine (ref: V. Harder, E. Pfeil and K. F. Zenner, Ber., 97(2), 510 1964) was prepared by lithium aluminium hydride reduction of 2-Methoxy-2-methylpropanenitrile (ref: R. A. Navdokina, E. N. Zilberman, Zh. Org. Khim., (1980, 16(8), 1629).

EXAMPLE 3

(±)-(2E,4E) N-(1,2-Dimethylpropyl)-5-[cis/trans-2-(2,2-dibromoethenyl) cyclopropyl]penta-2,4-dienamide (compound 44)

(i) To a solution of cis/trans (3:1) ethyl-2-formylcyclopropylcarboxylate (1.42 g) (ex Aldrich) in dichloromethane under nitrogen at room temperature was added triphenylphosphine (ex Aldrich) (12 g) and carbon tetrabromide (6.6 g)(ex Aldrich).

The solution was stirred at room temperature for three hours before it was partitioned between ether and water. Work-up in the conventional manner was followed by removal by filtration of the triphenyl phosphine oxide prior to chromatography which provided ethyl-2-(2,2,2-dibromoethenyl)cyclopropylcarboxylate (2.9 g). NMR $^1$H: 5.92 (1H,d), 4.16(2H,q), 2.44–0.95 (4H,m),1.26 (3H,t).

(ii) The above ester (1.8 g) in dichloromethane (12 ml) was cooled to −20° C. and diisobutyl aluminium hydride (12 ml of a 1M solution in hexane) was added dropwise. The solution was warmed to 0° and kept there before addition of 2N hydrochloric acid and work-up in the conventional manner to provide 2-(2,2-dibromoethenyl)-1-hydroxysethylcyclopropane (1.58 g) NMR: $^1$H 6.0, 5.7(1H,d), 3.44 (2H,d), 2.52 (1H,s).1.8–1.0(2H,m), 0.8 (2H,m).

(iii) The above alcohol (1.58 g) was oxidised using the conditions of Swern (oxalyl chloride. 0.6 ml; dimethyl sulphoxide, 1.0 ml; triethylamine, 4 ml) in dichloromethane to provide 2-(2,2-dibromoethenyl)cyclopropyl-methanal which was used directly in the next step.

NMR: ¹H 9.6, 9.43 (1H,d), 5.80 (1H,d), 2.46-1.82 (2H,m), 1.82-1.0(2H,m).

(iv) A solution of lithium diisopropylamide in dry tetrahydrofuran, prepared from n-butyllithium (2.3 ml of a 1.6M solution in hexane) and diisopropylamine (0.55 ml) was treated at −60° with triethylphosphono. crotonate (0.85 g) in THF under nitrogen. After two hours at −60°, the above aldehyde was added. After 18 hours at 25°, the mixture was partitioned between ether and water and worked up in the conventional manner. Purification by chromatography (silica, ether/hexane) gave (±)-(2E,4E)-ethyl-5--[cis/trans-2-(2,2-dibromoethenyl)cyclopropyl]penta-2,4-dienoate (1.223 g). NMR: ¹H7.24(1H,dd),6.28(1H,dd), 5.87(1H,d), 5.80 (1H,d), 5.67 (1H,dd), 4.20 (2H,q), 1.75 (2H,m), 1.30(3H,t),1.15(m).

(v) Potassium hydroxide (0.25 g) was added to a solution of the above ester (1.233 g) in ethanol (5 ml) and water (2 ml). The solution was stirred for 18 hours before removal of the ethanol under vacuum. Addition of dilute 2N hydrochloric acid was followed by extraction with ether. drying over magnesium sulphate and concentration under vacuum to provide (±)-2E,4E)-5-[cis/trans-(2,2-dibromoethenyl)cyclopropyl]penta-2,4-dienoic acid (0.74 g). NMR(CD₃OD): 7.30(1H,dd), 6.45(1H,dd), 6.15(1H,d), 5.88(1H,d), 5.00(1H,s), 1.92(2H,m), 1.28(2H,m).

(vi) The above acid (0.32 g) was dissolved in dichloromethane (5 ml) and triethylamine (0.14 ml) was added. Phenyl N-phenyl phosphoramidochloridate (ex Lancaster) was added. After 30 minutes at room temperature, 1,2-dimethyl propylamine (0.087 g) and triethylamine (0.14 ml) were added. The solution was stirred for 18 hours at room temperature before work-up in the conventional manner. Purification by chromatography (silica; ether/hexane) gave the title compound.

EXAMPLE 4

(±)-(2E,4E) N-(1,2-Dimethylpropyl)-5-(trans-2,2-difluoro-3-phenyl-cyclopropyl)penta-2,4-dienamide (compound 45)

Esterification of cinnamic acid (7.4 g) in the normal manner (ethanol, 120 ml; concentrated sulphuric acid, 6 ml) gave ethyl cinnamate (8.5 g). NMR ¹H: 7.55(1H,d), 7.15(5H,m), 6.2(1H,d), 4.05(2H,q), 1.15(3H,t).

The above ester (3.52 g) was treated with diisobutylaluminium hydride (40 ml of a 1M solution in hexane) in dichloromethane (40 ml) in the normal fashion to provide 3-phenylprop-2-en-1-ol (2.8 g). NMR ¹H: 7.2(5H,m), 6.55(1H,d), 6.35 (1H,t), 4.25(2H,d), 1.97(1H,s).

The above alcohol (2.05 g) in pyridine (1.6 ml) with acetic anhydride (1.8 g) was stirred at 25° for 3 hours before being partitioned between ether and dilute hydrochloric acid. Work-up in the conventional manner gave 3-phenylprop-2-enyl acetate (2.2 g). NMR ¹H: 7.15 (5H,m), 6.52 (1H,d), 6.22(1H,t), 4.57 (2H,d), 2.00(3H,s).

The above acetate (1.65 g) was dissolved in diglyme (ex Aldrich) and sodium chlorodifluoroacetate (ex Fluorochem) (8.4 g) was added at 25° under nitrogen. The solution was heated to 180° and kept there for half an hour. Cooling to 40° was followed by addition of further sodium chlorodifluoroacetate (6.2 g) and the mixture was reheated to 180° for a further half hour. The mixture was cooled and diluted with hexane. The organic phase was washed with water, dried over magnesium sulphate and the solvent removed under vacuum. Purification by chromatography (silica;ether/hexane) gave trans-2,2-difluoro-3-phenyl cyclopropylmethyl acetate (1.56 g). NMR ¹H: 7.30 (5H,m), 4.37 (1H,dd), 4.26 (1H,dd), 2.67 (1H,dd), 2.29 (1H,ddd), 2.13 (3H,s).

The above acetate (1.56 g) was stirred for 18 hours in aqueous methanol (10 ml) with potassium carbonate (2.94 g). Work-up in the conventional manner gave 2,2-difluoro-3-phenylcyclopropyl methanol (1.08 g) NMR ¹H: 7.30(5H,m), 3.94 (2H,m), 2.63 (1H,m), 2.24(1H,m), 1.67 (1H,s).

The above alcohol (0.55 g) was stirred in dichloromethane (6 ml) at 25° and pyridinium dichromate (2 g) (ex Alrich) and 3°A molecular seives (ex BDH) (1.5 g) were added. After three hours at room temperature, the mixture was diluted with ether and filtered through silica. washing with ether. Removal of solvent under vacuum gave 2,2-difluoro-3-phenylcyclopropyl methanal (0.255 g). NMR ¹H: 9.49 (1H,dd), 7.2-7.65(5H,m), 3.61 (1H,ddd), 2.955 (1H,ddd).

A solution of lithium diisopropylamide in dry tetrahydrofuran, prepared from n-butyl lithium (1 ml of a 1.6M solution in hexane) and diisopropylamine (0.24 ml) was treated at −60° with triethyl phosphonocrotonate (0.375 g) in THF under nitrogen. After 2 hours at −60°, the above aldehyde (0.255 g) was added. After 18 hours at 25° the mixture was partitioned between ether and water and worked up in the conventional manner.

Purification by chromatography (silica.ether/hexane) gave (±)-(2E,4E) -ethyl-5-[trans-2,2-difluoro-3-phenylcyclopropyl] penta-2,4-dienoate, which was converted to the title compound by analogy with example 3 step (vi).

EXAMPLE 5

(±)-(2E,4E) N-(1,2-Dimethylpropyl) 5-(trans-2,2-difluoro-3-(4-bromophenyl)cyclopropyl]-penta-2,4-dienamide (compound 46)

3-(4-Bromophenyl)prop-2-en1-ol (2.13 g) (see example 1) was reacted with acetic anhydride (1.2 g) in the usual manner to give 3-(4-bromophenyl)prop-2-enyl acetate (2.25 g) NMR ¹H: 7.35(2H,d), 7.08(2H,d), 6.52(1H,d), 6.10(1H,dt), 4.65(2H,d), 2.1(3H,s).

The above acetate (2.25 g) was reacted with sodium chlorodifluoro acetate (12.6 g) in the usual manner to afford trans-2,2-difluoro-3-(4-bromopheny)cyclopropylmethyl acetate (2.39 g). NMR ¹H: 7.48(2H,d), 7.1(2H,d), 4.30(2H,m), 2.62(1H,dd), 2.23(2H,m), 2.12(3H,s).

The above acetate (2.39 g) was reacted with potassium carbonate (2.36 g) in the usual manner to give 2,2-difluoro-3-(4-bromopheny)cyclopropylmethanol (1.93 g). NMR ¹H: 7.3(2H,d), 7.0(2H,d), 3.8(2H,m), 3.18(1H,s), 2.55(1H,m), 2.1(1H,m).

The above alcohol (1.93 g) was converted to the title compound by a method analogous to example 3 steps (iii) to (vi).

(±)-(2E,4E) N-Isobutyl-3-methyl-5-[trans-2,2-difluoro-3-(4-bromophenyl)cyclopropyl]penta-2,4-dienamide (compound 47) was prepared in an analogous manner using triethyl 3-methylphosphonocrotonate and isobutylamine.

EXAMPLE 6

(±)-(2E,4E) N-(1,2-Dimethylpropyl)-6-[cis,trans-2,(3-trifluoromethylphenyl)cyclopropyl]hexa-2, 4-dienamide (compound 48)

(i) Butyn-4-ol (0.31 g) was heated at 60° for one hour with tributyl tin hydride (ex. Aldrich) (1.6 g) and azobisisobutyronitrile (0.01 g) (ex. Aldrich). Cooling and distillation (Kugelrohr 150°, 1 mmHg) gave 4-tributyltinbut-3-en-1-ol (1.17 g) as a 1:1 mixture of trans:cis olefin isomers. (Reference J. K. Stille, Ang.Chem., Int. Ed. Engl. 1986,25,508). NMR $^1$H: 5.95(2H,m), 3.60(2H,m), 2.3(2H,m), 0.9–2.0(21H,m).

(ii) Palladium bis acetonitrile dichloride (0.01 g) was dissolved in dry dimethyl formamide (10 ml) at 25° under argon. 3-Trifluoromethyl iodobenzene (1.03 g) (ex. Fluorochem) was added in DMf followed by the above alcohol (1.17 g). After 72 hours, the solution was partitioned between ether and 10% ammonium hydroxide solution and worked up in the usual manner.

Purification by chromatography (silica; ether/hexane) gave 4-(3-trifluoromethylphenyl) but-3-en-1-ol (0.67 g) as a 1:1 mixture of cis:trans olefin isomers (Reference J. K. Stille and B. L. Groh, J. Am. Chem. Soc., 109, 1987, 815). NMR $^1$H: 7.5(4H,m), 6.55($^1$H,d), 6.32($^1$H,dt), 3.78(2H,m), 2.55(2H,m), 1.50(1H,s).

(iii to vi) The above alcohol was converted into the title compound by analogy with example 1 steps (iii) to (vi).

EXAMPLE 7

(±)-(E)
N-(1,2-Dimethylpropyl)-3-[cis-2,(3-trifluoromethylphenyl) cyclopropyl]prop-2-enamide (compound 49)

(i) Ethyl propiolate (0.98 g) (ex Lancaster) and tributyltinhydride (3.01 g) with azobiisidobutyronitrile (0.01 g) were heated at 60° for 18 hours. Cooling and purification by chromatography (silica; ether/hexane) gave (Z)-ethyl-3-tributyltinpropenoate (1.9 g) (Reference J. K. Stille et al, J.Amer.Chem.Soc., 109, 1987,815). NMR $^1$H: 7.14(1H,d), 6.73(1H,d), 4.22(2H,q), 1.38(18H,m), 0.9(12H,m).

(ii) The above ester (0.78 g) was dissolved in dichloromethane (4 ml) and cooled to −20° under nitrogen. Diisobutyl aluminium hydride (4ml of a 1M solution in hexane) was added dropwise. After 18 hours at 25°, careful addition of dilute hydrochloric acid was followed by work up in the usual manner, to afford 3-tributyltin-prop-2-en 1-ol (0.75 g). NMR 1H: 6.72(1H,dt), 6.10(1H,d), 4.15(2H,dd), 1.40(18H,m), 0.90(9H,m).

(iii to v) The above alcohol (0.75 g) was converted to (±)-cis-2-3-trifluoromethylphenyl)-1-formyl cyclopropane (0.2 g) by a method analogous to Example 6 (ii) and Example 1 steps (iii) and (iv). NMR $^1$H: 8.95(1H,d), 7.50(4H,m), 1.0–2.5(4H,m).

(vi) The above aldehyde (0.2 g) was stirred in dichloromethane (5 ml) with carboethoxymethylene triphenyl phosphorane under nitrogen for 18 hours at 25°: concentration in vacuo followed by hexane washing of the residue and removal of hexane in vacuo gave (±)-(E)-Ethyl-3-[cis-2-(3-trifluoromethylphenyl)cyclopropane]-prop-2-enaote (0.18 g). NMR $^1$H: 7.43(4H,m), 6.18(1H,dd), 5.94(1H,d), 4.06(2H,q), 2.62(1H,m), 2.09(1H,m), 1.55(1H,m), 1.34(1H,m), 1.22(3H,t).

(vii) The above ester was converted into the title compound by analogy with example 1(vi).

EXAMPLE 8

(±)-(2E,4E)
N-(1,2-Dimethylpropyl)-5-[cis-trans-2,(3-trifluoromethylphenyl)cyclopropyl]penta-2,4-dienamide (compound 50)

(±)-(E)-Ethyl-3-[cis-2-(3-trifluromethylphenyl)cyclopropyl]prop-2-enoate (0.18 g) (example 7) was dissolved in dicyhloromethane (3 ml) and cooled to −20° under nitrogen. Diisobutylaluminiumhydride (1.3 ml of a 1M solution in hexane) was added and the solution stirred at 25° for 18 hours. Careful addition of dilute hydrochloric acid was followed by work up in the usual manner to give cis-2-(3-trifluoromethylphenyl)-1-(3-hydroxyprop-2-en-1-yl)cyclopropane (0.15 g). NMR $^1$H: 7.43(4H,m), 5.79(1H,dt), 4.98(1H,dd), 3.95(2H,d), 2.40(1H,m), 1.94(1H,m), 1.33(1H,m), 1.10(2H,m).

The above alcohol (1.35 g) was oxidised using the procedure of Swern (oxalyl chloride, 0.54 ml; dimethylsulphoxide, 0.86 ml; triethylamine 3.8 ml) in dichloromethane to give cis-2-(3-trifluoromethylphenyl)-1-(1-propen-3-alyl)cyclopropane (1.3 g). NMR $^1$H: 9.21(4H,d), 7.50(4H,m), 6.28(1H,dd), 5.98(1H,dd), 2.79(1H,m), 2.12(1H,m), 1.68(1H,m), 1.42(1H,m).

The above aldehyde (1.3 g) was reacted with carboethoxymethylene triphenylphosphorone (1.74 g) by analogy with Example 7(vi) to give (±)-(2E,4E)-Ethyl-5-[cis-2,(3-trifluoromethylphenyl)cyclopropyl]penta-2,4-dienoate (1.1 g). NMR $^1$H: 7.42(4H,m), 7.05(1H,dd), 6.31(1H,dd), 5.73(1H,d), 5.31(1H,dd), 4.17(2H,q), 2.56(1H,m), 2.03(1H,m), 1.48(1H,m), 1.25(4H,m.)

The above ester was converted into the title compound by analogy with example 1(vi) to give a 6:1 mixture of cis:trans cyclopropyl isomers.

(±)-(2E,4E) N-Isobutyl-5-[cis,trans-2,(3-trifluoromethylphenyl)cyclopropyl]penta-2,4-dienamide (compound 51) was prepared in an analogous manner as a 4:1 mixture of cis:trans cyclopropyl isomers using isopropylamine instead of 1,2-dimethylpropylamine.

EXAMPLE 9

(±)-(2E,4E)
N-(1,2-Dimethylpropyl)-5-[cis-trans-2,(4-chlorophenyl)-2-methylcyclopropyl]pen ta-2,4-dienamide (compound 52)

To a solution of lithium isopropylcyclohexylamide (prepared from 12.5 ml of n-butyllithium 1.6M solution and isopropyl cyclohexylamine (3.3 ml) (ex Aldrich) in TMF was added at −60°, ethyltrimethylsilylacetate (3.6 ml) (ex Fluka). After 30 minutes at −60°, 4-chloro acetophenone (ex Aldrich) (1.55 g) was added. After 18 hours at 25° the mixture was partitioned between ether and water and worked up in the usual manner. Purification by chromatography (silica; ether/hexane) gave Ethyl-3-(4-chlorophenyl)-but-2-enoate (1.22 g), as a 1:1 mixture of E:Z olefin isomers. NMR $^1$H: 7.2(4H,m), 6.0 and 5.0(1H,m), 4.12(2H,m), 2.51 and 1.90(3H,s), 1.25(3H,m).

The above ester (1.44 g) was dissolved in dichloromethane (13 ml) and cooled to −20°. Diisobutylaluminium hydride (12.8 ml of a 1M solution in hexane) was added dropwise. After 18 hours at 25° dilute hydrochloric acid was added carefully and the mixture worked up in the usual manner to give 3-(4-chlorophenyl)but-2-en-1-ol (0.44 g). NMR $^1$H: 7.18(4H,s), 5.85(1H,t), 4.25(2H,d), 3.05(1H,s), 2.05(3H,s).

The above alcohol was converted into the title compound by a method analogous to Example 1 steps (iii) to (vi).

EXAMPLE 10

(±)-(2E,4E)
N-(1,2-Dimethylpropyl)-5-[trans-2,2-dimethyl-3-(3-trifluoromethylphenyl)cyclopropyl]penta-2,4-dienamide (compound 53)

Ethyl-3-trifluoromethylcinnamate (0.98 g) (Example 2) in tetrahydrofuran under nitrogen was treated with the ylid prepared from isopropyl triphenylphosphonium iodide (2.12 g) and n-butyllithium (2.8 ml). After 20 hours at 80° the mixture was worked up in the usual manner. Purification by chromatography (silica; ether/hexane) gave (±)-n-butyl-[trans-3-(3-trifluoromethylphenyl)-2,2-dimethylcyclopropyl]-formate (0.78 g). NMR $^1$H: 7.22(4H,m), 4.20(2H,m), 2.72(1H,m), 2.00(1H,m), 1.40(7H,m), 0.89(6H,m).

The above ester (0.78 g) was dissolved in dichloromethane (12 ml) under nitrogen and cooled to −20°. Diisobutylaluminium hydride (7.4 ml) was added dropwise and the solution stirred at 25° for 18 hours. Careful addition of dilute hydrochloric acid was followed by work up in the usual manner to give (±)-[trans-3-(3-trifluoromethylphenyl)-2,2-dimethylcyclopropyl]methanol (0.31 g). NMR $^1$H: 7.5(4H,m), 3.65(2H,d), 2.55(1H,bs), 1.62(1H,d), 1.14(1H,m), 1.15(3H,s). 0.90(3H,s).

The above alcohol was converted to the title compound by a method analogous to Example 1 steps (iv) to (vi).

(±)-(2E,4E) N-(1,2-Dimethylpropyl)-5-[trans-2,2-dimethyl-3-(3,4-dichlorophenyl)cyclopropyl]penta-2,4-dienamide. (Compound 54) was prepared in an analogous manner starting from ethyl-3,4-dichlorocinnamate.

EXAMPLE 11

(±)-(2E,4E)
N-(1,2-Dimethylpropyl)-5-[trans-2-(4-chlorophenyl)-1-methylcyclopropyl]penta-2,4-dienamide (compound 55)

4-Chlorobenzaldehyde (6.8 g) (ex Aldrich) in dichloromethane (250 ml) was reacted with carboethoxymethylenetriphenylphosphorane (17.5 g) (ex. Lancaster) at 25° for 18 hours. Concentration in vacuo was followed by copious hexane washing of the residue. Combined hexane washes were concentrated to give (E)-ethyl-3-(4-chlorophenyl-2-methylprop-2-enoate (11.6 g). NMR $^1$H: 7.35(4H,m), 4.25(2H,1), 2.05(3H,s), 1.31(3H,t).

The above ester (11.6 g) was dissolved in dichloromethane (100 ml) and cooled to −20°. Diisobutylaluminium hydride (100 ml) was added dropwise. After 18 hours at 25° dilute hydrochloric acid was added carefully. The mixture was worked up in the usual manner to give (E)-3-(4-chlorophenyl)-2-methylprop-2-en-1-ol (8.6 g). NMR $^1$H: 7.34(2H,d), 7.22(2H,d), 6.49(1H,s), 4.18(2H,s), 1.90(3H,s), 1.66(1H,s).

The above alcohol was treated with diethyl zinc (45.5 ml) and diiodomethane (8.1 ml) in hexane in the usual manner to give (±)-[trans-[2-(4-chlorophenyl)-1-methylcyclopropyl]methanol (1.94 g). NMR $^1$H: 8.94(1H,s), 7.30(2H,d), 7.06(2H,d), 2.68(1H,dd), 2.24(1H,dd), 1.46(1H,dd), 0.98(3H,?). This was converted to the title compound by a method analogous to Example 3 steps (iv) to (vi).

EXAMPLE 12

(−)
N-Isobutyl-5-[(1S,2R)-trans-2-(3,4-dichlorophenyl)cyclopropyl]-penta-2,4-dienamide (compound 56)

3-(3,4-Dichlorophenyl)prop-2-en-1-ol(1.0 g)(prepared by analogy to Example 2(i) and Example 1(ii)) was oxidised using the procedure of Swern (oxalyl chloride, 0.5 ml; dimethyl sulphoxide, 0.7 ml; triethylamine 3.4 ml) to give 3-(3,4-dichlorophenyl)-prop-2-enal (0.9 g). NMR $^1$H: 9.76(1H,d), 7.53(3H,m), 7.41(1H,d), 6.68(2H,dd).

The above aldehyde (0.66 g) was stirred in ethanol (5 ml) with triethyl orthoformate (0.6 ml) (ex Aldrich) and ammonium nitrate (ex Aldrich) (0.01 g) for 3.5 hours at 25°. Concentration in vacuo and work up in the usual manner gave E-1-(3,4-dichlorophenyl)-3,3-diethoxy but-1-ene (0.97g). NMR $^1$H: 7.32(3H,m), 6.79(1H,d), 6.19(1H,dd), 5.08(1H,d), 3.69(4H,m), 1.29(6H,m).

The above acetal (0.67 g) was disolved in benzene (25 ml) and treated with (+)-L-diisopropyl tartrate (0.7 g) (ex Aldrich) and p-toluene sulphoric acid (0.01 g) (ex Aldrich). The mixture was heated at 80° for 6 hours using a Dean-Stark apparatus. The solution was cooled and worked up in the usual manner to give (−)-4,5-dicarboisopropoxy-2-[(E)-2-(3,4-dichlorophenyl)ethenyl]-1,3-dioxolane (0.92 g). NMR $^1$H: 7.50(1H,d), 7.40(1H,d), 7.25(1H,dd), 6.74(1H,d), 6.25(1H,dd), 5.81(1H,d), 5.14(2H,m), 4.77(1H,d), 4.69(1H,d), 1.33(12H,m).

The above acetal (0.9 g) was reacted with diethyl zinc (11 ml) and diiodomethane (1.8 ml) in hexane in the usual manner to give (−)-4,5-dicarboisopropoxy-2[trans-(2R,3R)-2-(3,4-dichlorophenyl)cycloprop-1-yl]-1,3-dioxolane (0.8 g). $[\alpha]_D-96.1°$ (c0.96, Ethanol). NMR $^1$H: 7.21(1H,d), 7.13(1H,d), 6.85(1H,dd), 5.05(1H,d), 5.02(2H,m), 4.65(1H,d), 4.52(1H,d), 2.08(1H,m), 1.47(1H,m), 1.21(12H,m), 1.14(1H,m), 0.92(1H,m).

The above acetal (0.8 g) was heated at 70° for 12 hours in tetrahydrofuran (5 ml) in the presence of dilute hydrochloric acid (3 ml). Work up in the usual manner gave (−)-[trans-(2R,3S)-2-(3,4-dichlorophenyl)cyclopropyl]-methanol (0.23 g). NMR $^1$H: 9.39(1H,d), 7.39(2H,m), 6.94(1H,dd), 2.56(1H,m), 2.09(1H,m), 1.65(2H,m).

Lithium diisopropylamide prepared from n-butyllithium (0.6 ml) and diisopropylamine (0.14 ml). was treated at −60° under nitrogen in tetrahydrofuran with triethyl-4-phosphonocrotonate (0.21 g) in tetrahydrofuran. After 2 hours at −60°, the above aldehyde was added. After 18 hours at 25°, water was added and the mixture worked up in the usual manner. Purification by chromatography (silica; hexane/ether) gave (−)-(2E,4E)-Ethyl-5-[trans-(2R,3S)-2-(3,4-dichlorophenyl)cyclopropyl]penta-2,4-dienoate (0.16 g) $[\alpha]_D-304.7°$ (c0.9, Ethanol). NMR $^1$H: 7.28(3H,m), 6.88(1H,dd), 6.18(1H,dd), 5.84(1H,dd), 5.78(1H,d), 4.10(2H,q), 1.90(2H,m), 1.20(5H,m).

The above ester was converted into the title compound in an analogous fashion to example 1(vi).

(+) N-Isobutyl-5-[(1R,2S)-trans-2-(3,4-dichlorophenyl)cyclopropyl]penta-2,4-dienamide (compound 57) was prepared in an analogous manner using (−)-D-diisopropyl tartrate (ex Aldrich).

EXAMPLE 13

(±)-(2E,4E)
N-Isobutyl-5-[trans-2-(2,6-dichloro-4-pyridyl)cyclopropyl]-3-methylpenta-2,4-dienamide (compound 58)

2,6-Dichloroisonicotinic acid (4.0 g) (prepared according to M. M Robinson, J.Amer.Chem.Soc. 80,5481,1958) was dissolved in ethanol (20 ml) and concentrated sulphuric acid (1 ml). After 6 hours at 80°, the solution was cooled, concentrated in vacuo and the residue worked up in the usual manner to give ethyl-2,6-dichloroisonicotinate (3.7 g). NMR $^1$H: 7.84(2H,s), 4.48(2H,q), 1.48(3H,t).

The above ester was dissolved in dichloromethane (60 ml) and cooled to −20° under nitrogen. Diisobutylaluminium hydride (38 ml) was added dropwise. After 2 hours at 0°, dilute hydrochloric acid was carefully added and the mixture worked up in the usual manner to give 2,6-dichloro-4-hydroxymethylpyridine. NMR $^1$H: 7.64(2H,s), 4.98(2H,s).

Oxidation of the above alcohol (1.2 g) according to the conditions of Swern (oxalyl chloride, 0.33 ml; dimethyl sulphoxide, 0.54 ml; triethylamine, 2.35 ml) gave (2,6-dichloro-4-pyridyl)methanal (1.2 g). NMR $^1$H: 10.02(1H,s), 7.68(2H,s).

The above aldehyde (1.2 g) was dissolved in dichloromethane (40 ml) and carboethoxymethylenetriphenylphosphorane (2.4 g) was added. After 18 hours at 25° the solution was concentrated in vacuo and the residue washed with hexane. Combined hexane washings were concentrated in vacuo to give ethyl-3-(2,6-dichloro-4-pyridyl)propenoate (1.2 g). NMR $^1$H : 7.50(2H,d), 2.28(2H,s), 6.52(2H,d), 4 29(2H,q), 1.32(3H,t).

The above ester (0.25 g) was added to the ylid prepared from trimethylsulphoxonium iodide (0.24 g) and sodium hydride (0.044 g of a 60% dispersion in mineral oil) at 25° under nitrogen in dimethyl sulphoxide (4 ml). After 18 hours at 25°, water was added carefully and the mixture worked up in the usual manner. Purification by chromatography (silica; ether/hexane) gave (±)-Ethyl-(trans-2-(2,6-dichloro-4-pyridyl)cyclopropyl]formate (0.12 g). NMR $^1$H: 6.93(2H,s), 4.16(2H,q), 2.42(1H,ddd), 1.99(1H,ddd), 1.69(1H,ddd), 1.30(2H,m), 1.25(3H,t).

The above ester (0.34 g) was dissolved in dichbromethane (7 ml) under nitrogen and cooled to −20°. Diisobutylaluminium hydride (2.8 ml) was added dropwise. After 0.5 hours, methanol (0.5 ml) was added carefully followed by 2M sodium hydroxide solution (5 ml). The mixture was worked up in the usual manner. NMR $^1$H 6.98(2H,s), 3.64(2H,m), 3.30(1H,bs), 0.9–2.0(4H,m).

The above alcohol (0.21 g) was oxidised using the conditions of Swern (oxalyl chloride, 0.1 ml; dimethyl sulphoxide. 0.15 ml; triethylamine. 0.66 ml) to give (±)-[trans-2-(2,6-dichloro-4-pyridyl)cyclopropyl]methanal (0.2 g). NMR $^1$H: 9.44(1H,d), 6.96(2H,s), A solution of lithium diisopropylamide in tetrahydrofuran (2 ml) at −60° prepared from n-butyllithium (0.7 ml) and diisopropylamine (0.16 ml) was treated with triethyl 4-phosphono-3-methylcrotonate (0.26 g). After 2 hours at −60°, the above aldehyde (0.2 g) was added. After 2.5 hours at 25°, water was added and the mixture worked up in the normal manner. Purification by chromatography (silica; ether/hexane) gave (±)-(2E,4E)-ethyl-3-methyl-5-[trans-2-(2,6-dichloro-4-pyridyl)cyclopropyl]penta-2,4-dienoate (0.18 g). NMR $^1$H: 6.92(2H,s), 6.22(1H,d), 5.75(2H,m), 4.13(2H,q), 2.24(3H,s), 1.94(2H,m), 1.41(1H,m), 1.28(1H,m), 1.22(3H,t).

The above ester was converted into the title compound by analogy with example 1(vi).

EXAMPLE 14

(±)-(2E,4E)
N-(1,2-Dimethylpropyl)-5-[trans-2-(3,4-dibromophenyl) cyclopropyl]penta-2,4-dienamide (compound 59)

3-Nitro-4-bromotoluene (54 g) (ex Lancaster) in a water, ethanol solution (100 ml. 1:1) was rapidly stirred and iron powder (84 g) (ex BDH) was added at 25°. This mixture was heated to reflux and concentrated hydrochloric acid (2.19 g) in water, ethanol (50 ml, 1:1) was added dropwise over 30 minutes. After 4 hours at reflux, the mixture was cooled, made alkaline with 15% potassium hydroxide solution and filtered through celite washing with ethanol (2×50 ml). The resulting mixture was diluted with water (1000 ml) and worked up in the usual manner, to give 3-amino-4-bromotoluene (43.6 g). NMR $^1$H : 7.25(1H,d), 6.40(2H,m), 3.96(2H,bs), 2.2(3H,s).

The above aminotoluene (24 g), was stirred in concentrated hydrobromic acid (230 ml) at 0° C. Sodium nitrite (9.8 g) (ex BDH) in water (35 ml) was added keeping the reaction temperature between 0° and 5°. The mixture was poured onto cuprous bromide (37 g) (ex BDH) in water (230 ml) and hydrobromic acid at 50°. After 2 hours at 50° and 18 hours at 25°, water was added and the mixture worked up in the usual manner. Purification by distillation (100°, 0.5 mmHg) gave 3,4-dibromotoluene (12.7 g). NMR $^1$H 7.53(2H,m), 6.95(1H,dd), 2.30(3H,s).

The above toluene (5 g) in glacial acetic acid (20 ml) (ex BDH) and acetic anhydride (32.6 g) was cooled to −10°. Sulphuric acid (7.8 g) was added dropwise keeping the reaction temperature lower than −5°. Chromium trioxide (ex BDH) (6 g) was added portionwise. maintaining reaction temperature between −5° and 0°. After 15 minutes at 0°, the mixture was poured onto ice (150 g) and worked up as usual to give diacetoxymethyl-3,4-dibromobenzene. NMR $^1$H 7.53(2H,m), 6.95(1H,dd), 2.30(6H,s).

The above diacetate was taken up in ethanol (15 ml), water (15 ml) and concentrated sulphuric acid was added (1.5 ml). After one hour at reflux the solution was worked up in the usual manner to give 3,4-dibromobenzaldehyde (2.25 g). NMR $^1$H 10.04(1H,s), 7.53(2H,m), 6.95(1H,dd).

The above aldehyde (2.25 g) was dissolved in dichloromethane (25 ml) and carboethoxymethylenetriphenylphosphorane (2.96 g) was added. After 18 hours at 25° the solution was concentrated in vacuo and the residue washed with hexane. Combined hexane washings were concentrated in vacuo to give ethyl-3-(3,4-dibromophenyl)propenoate (2.4 g). NMR $^1$H 7.7(2H,m), 7.50(1H,d), 7.15(1H,dd), 6.32(1H,d), 4.26(2H,q), 1.33(3H,t).

The above ester (2.4 g) in dichloromethane (25 ml) under nitrogen was cooled to −20° and diisobutylaluminium hydride (14.5 ml) was added dropwise. After 18 hours at 25° dilute hydrochloric acid was added carefully and the mixture worked up in the usual manner to give 3-(3,4-dibromophenyl)prop-2-en-1-ol (2.04 g). NMR $^1$H : 7.53(2H,m), 7.13(1H,dd), 6.56(1H,d), 6 20(1H,dt), 4.30(2H,d), 1.98(1H,s).

The above alcohol (2 g) was treated with diethyl zinc (35 ml) and dioodomethyl 15.52 ml) in hexane in the usual manner to give (±)-[Trans-2-(3,4-dibromophenyl)cyclopropyl]methanol (1.3 g). NMR $^1$H: 7.40(1H,d), 7.30(1H,d), 6.76(1H,dd), 3.53(2H,d), 2.30(1H,s), 1.68(1H,m), 1.33(1H,m), 0.87(2H,m).

The above alcohol was converted into the title compound by analogy with example 1 steps (iv) to (vi).

(i) (±)-(2E,4E) N-Isobutyl-3-methyl-5-[trans-2-(3,4-dibromophenyl)cyclopropyl]penta-2,4-dienamide (compound 60) and (ii) (±)-(2E,4E) N-(2-methylbut-2-enyl)-3-methyl-5-[trans-2-(3,4-dibromophenyl)cyclopropyl]penta-2,4-dienamide (compound 93) were prepared in an analogous manner using triethyl-3-methylphosphonscrotonate and (i) isobutylamine and (ii) 2-methylprop-2-enylamine respectively.

EXAMPLE 15

(±)-(2E,4E) N-(1,2-Dimethylpropyl)-5-[trans-2-(3,5-dichloro-4-bromophenyl)cyclopropyl]penta-2,4-dienamide (compound 61)

P-Aminobenzonitrile (11.8 g) (ex Aldrich) in dry chloroform (250 ml) under nitrogen was treated with sulphuryl chloride (4.05 g) (ex BDH) maintaining reaction temperature below 35°. After 2 hours at reflux the mixture was poured onto ice and made alkaline with 2M sodium hydroxide solution. Work up in the usual manner gave 3,5-dichloro-4-aminobenzonitrile (18.2 g) NMR $^1$H 7.35(2H,s), 4.70(2H,bs).

The above aminonitrile (18.7 g) in concentrated hydrobromic acid (190 ml) at 0° was treated with sodium nitrite (7.6 g) in water (30ml). The resulting mixture was poured onto cuprous bromide (28.7 g) in water (180 ml) and hydrobromic acid (30 ml) at 50°. After 2 hours at 50° and 18 hours at 25° the mixture was diluted with water and worked up in the usual manner to give 3,5-dichloro-4-bromobenzonitrile (9.2 g). NMR $^1$H: 7.63(2H,s).

The above nitrile (5 g) in ether (100 ml) under nitrogen was treated with diisobutylaluminium hydride (22 ml of a 1M solution in toluene). After 18 hours at 25°, 1,4-dioxane (150 ml) and water (10 ml) were added followed by dilute hydrochliric acid (250 ml). After 30 minutes at 25° the mixture was worked up in the usual manner to give 3,5-dichloro -4-bromo benzaldehyde (4.52 g). NMR 1H 9.89(1H,s), 7.85(2H,s).

The above aldehyde was converted into the title compound by analogy with example 1.

(±)-(2E,4E) N-Isobutyl-3-methyl-5-[trans-2-(4-bromo-3,5-dichlorophenyl)cyclopropyl]penta-2,4-dienamide (compound 62) was prepared in an analogous manner using triethyl-4-phosphono-3-methyl-crotonate and isobutylamine.

EXAMPLE 16

(±)-(2E,4E) N-(1,2-Dimethylpropyl)-5-[trans-2-(4-(2,2-dibromoethenyl) phenyl)cyclopropyl]penta-2,4-dienamide (compound 65)

Ethyl-4-formylbenzoate (2.46 g) (ex Lancaster) in dichloromethane (30 ml) under nitrogen was treated with triphenylphosphine (15.7 g) and carbon tetrabromide (9.9 g) at 0°. After 1.5 hours at 25°, water was added and the mixture worked up in the normal manner. Purification by chromatography (silica, ether/hexane) gave ethyl-4-(2,2-dibromoethenyl)benzoate (3.32 g). NMR $^1$H 8.0(2H,d), 7.50(2H,d), 7.45(1H,s), 3.85(3H,s).

The above ester (3.32 g) in dichloromethane (10 ml) at 0.20° under nitrogen was treated with diisobutyl aluminiumhydride (21 ml). After 1 hour at 0° C. dilute hydrochloric acid was added and the mixture worked up in the normal manner to give 4-(2,2-dibromoethenyl)benzyl alcohol (3.18 g). NMR $^1$H 7.50(2H,d), 7.41(1H,s), 7.20(2H,d), 4.33(2H,s), 3.65(1H,s).

The above alcohol (3.18 g) was oxidised using the conditions of Swern oxalyl chloride, 0.96 ml, dimethyl sulphoxide, 1.56 ml; triethylamine, 6.9 ml) in dichloromethane to give 4-(2,2-dibromoethenyl)benzaldehyde (2.04 g). NMR $^1$H 10.94 (1H,s), 7.86(2H,d), 7.61(2H,d), 7.45(1H,s).

The above aldehyde was converted into (±)-(2E,4E)-ethyl-5-[trans-(4-(2,2-dibromoethenyl)phenyl)cyclopropyl] penta-2,4-dienoate by analogy with example 1 steps (i) to (v). The above ester was converted into the title compound by analogy with example 3 steps (v) and (vi).

EXAMPLE 17

(±)-(2E,4E) N-(1,2-dimethylpropyl)-5-trans-2-(4-ethynylphenyl)cyclopropyl]penta-2,4-dienamide (compoung 66)

(±)-Trans-2-[4-(2,2-dibromoethenyl)phenyl]cyclopropylmethanol (1.43 g) (prepared as in example 16) in dry tetrahydrofuran under nitrogen at −40° was treated with n-butyllithium (8.1 ml) After 4 hours at 25° water was added and the mixture worked up in the usual manner. Purification by chromatography (silica ether/hexane) gave (±)-trans-2-(4-ethynylphenyl)cyclopropane methanol (0.62 g). NMR $^1$H: 7.41(2H,d), 6.90(2H,d), 3.30(2H,d), 2.95(1H,s), 2.59(1H,s), 1.85(1H,m), 1.34(1H,m), 0.90(2H,m).

The above alcohol was converted into the title compound by analogy with example 1.

EXAMPLE 18

(±)-(2E,4E) N-(1,2-Dimethylpropyl)-5-[trans-2-(3,4,5-trichlorophenyl)cyclopropyl]penta-2,4-dienamide (compound 67)

4-Amino-3,5-dichlorobenzonitrile was converted into the title compound by analogy with example 15 using hydrochloric acid and cuprous chloride (ex BDH) in place of hydrobromic acid and cuprous bromide.

(±)-(2E,4E) N-Isobutyl-3-methyl-5-[trans-2-(3,4,5-trichlorphenyl)cyclopropyl]penta-2,4-dienamide (compoung 68) was prepared in an analogous manner using triethyl-3-methylphosphonocrotonate and isobutylamine.

EXAMPLE 19

(±)-(2E,4E) N-(1,2-Dimethylpropyl)-4-fluoro-5-[trans-2-(3,4-dichlorophenyl)cyclopropyl]penta-2,4-dienamide (compount 69)

Sodium hydride (0.74 g of a 60% dispersion in mineral oil) (ex BDH)in THF (30 ml) was treated with Ethylfluoroacetate (2.7 ml) (ex Lancaster) and diethyl oxalate (ex BDH) (3.8 ml). After 4 hours at 80° C., (±)-trans-2-(3,4-dichlorophenyl)cyclopropylmethanal (6 g) (example 2(i) and example 1(ii) to (iv)) was added. After 18 hours at 25°, water was added and the mixture worked up in the usual manner. Purification by chromotography (silica, hexane/ether) gave (±)-Ethyl-(2Z)-3-[trans-2-(3,4-dichlorophenyl)cyclopropyl]-2-fluoropent-2-enoate (4 g). NMR $^1$H 7.30(1H,d), 7.15(1H,d), 6.90(1H,dd), 5.70(1H,dd), 4.30(2H,q), 2.08(2H,m), 1.35(2H,m), 1.30(3H,t).

The above ester (4 g) was dissolved in dichloromethane (30 ml) and cooled to −20° under nitrogen. Diisobutylaluminium hydride (26 ml) was added dropwise. After 18 hours at 25° dilate hydrochloric acid was carefully added and the mixture worked up in the usual manner to give (±)-(2Z)-3-[trans-2-(3,4-dichlorophenyl)cyclopropyl]-2-fluoroprop-2-en-1-ol (3.3 g). NMR $^1$H: 7.32(1H,d), 7.17(1H,d), 6.90(1H,dd), 4.10(2H,dd), 3.60(1H,t), 1.90(2H,m), 1.20(2H,m).

The above alcohol (3.3 g) was oxidised using the conditions of Swern oxalyl chloride, 1.2 ml; dimethyl sulphoxide, 2.0 ml; triethylamine, 8.8 ml] in dichloromethane to give (±)-(2Z)-3-[trans-2-(3,4-dichlorophenyl)cyclopropyl]-2-fluoroprop-2-enal (3.25 g). NMR $^1$H: 9.20(1H,d), 7.39(1H,d), 7.22(1H,d), 6.95(1H,dd), 5.60(1H,dd), 2.20(2H,m), 1.50(2H,m).

The above aldehyde (0.5 g) was dissolved in dichloromethane (5 ml) under nitrogen and treated with carboethoxymethylenetriphenylphosphorane (0.67 g) at 25°. After 18 hours at 25° the solution was concentrated in vacuo and the residue washed with hexane. Combined hexane washings were concentrated in vacuo to give (±)-(2E,4E)-Ethyl-4-fluoro-5-[trans-2-(3,4-dichlorophenyl) cyclopropyl]penta-2,4-dienoate (0.58 g). NMR $^1$H: 7.30(1H,d), 7.00(3H,m), 6.05(1H,d), 5.90(1H,m), 4.20(2H,q), 2.00(2H,m), 1.30(3H,t), 1.30(2H,m).

The above ester was converted into the title compound by analogy with example 1(vi).

EXAMPLE 20

(±)-(2E,4Z)
N-Isobutyl-3-methyl-4-fluoro-5-[trans-2-(3,4-dichlorophenyl)cyclopropyl]penta-2,4-dienamide (compound 70)

(±)-(2Z)-2-Fluoro-3-[trans-2-(3,4-dichlorophenyl)cyclopropyl]prop-2-enal (2.59 g) (example 19) in ehter (10 ml) was treated at 0° under nitrogen with methyl magnesium iodide, prepared from magnesium turning (0.26 g) and methyl iodide (0.7 ml) in ether (20 ml). After 18 hours at 25° the mixture was worked up as usual. Purification by chromatography (silica, ether/hexane) gave (±)-(3Z)-4-[trans-2-(3,4-dichlorophenyl)cyclopropyl]but-3-en-2-ol (2.0 g). NMR $^1$H: 7.23(1H,d), 7.05(1H,d), 6.90(1H,dd), 4.52(1H,m), 4.23(1H,m), 3.0(1H,s), 1.80(2H,m), 1.35(3H,d), 1.18(2H,m).

The above alcohol (2.0 g) was oxidised using the conditions of Swern (oxalyl chloride, 0.7 ml; dimethyl sulphoxide 61 ml; triethylamine, 5.1 ml) in dichloromethane to give (±)-(3Z)-3-fluoro-4-[trans-2-(3,4-dichlorophenyl)cyclopropyl]but-3-en-2-one (1.5 g). NMR $^1$H: 7.30(1H,d), 7.10(2H,d), 6.95(1H,dd), 5.70(1H,dd), 2.32(3H,d), 2.10(2H,m), 1.43(2H,m).

Chloroacetyl chloride (ex. Aldrich) (50 g) was added dropwise, with stirring to isobutylamine (ex. Aldrich) (70 ml) in dry ether (250 ml) at 0° C. When the mixture had reached room temperature it was worked up in conventional fashion to give N-isobutyl 2-chloroacetamide. The latter (20 g) was heated for 3 hours at 120° C. with triethylphosphite (23 g). The mixture was subjected to distillation in vacuo to give N-isobutyl diethylphosphono acetamide (22.5 g, bp. 140–142.5° C. at 0.1 mm).

A solution of lithium diisopropylamide in tetrahydrofuran under nitrogen, prepared from n.butyl lithium (2.3 ml) and diisopropylamine (0.51 ml), at −70° was treated with diethyl-N-isobutylphosphonoacetamide (0.46 g) in dry tetrahydrofuran. After 2 hours at 25° the above ketone (0.5 g) was added. After 18 hours at 25° water was added and the mixture worked up in the normal manner. Purification by chromatography (silica. ether/hexane) gave the title compound (0.24 g).

(±)-(2Z,4E) N-(2-Methylprop-2-enyl)-3-methyl-4-fluoro-5-[trans-2-(3,4-dichlorophenyl)cyclopropyl]penta-2,4-dienamide (compound 94) was prepared in an analogous manner using 2-methylprop-2-enylamine in place of isobutylamine.

EXAMPLE 21

(±)-(2E,4E)
N-(1,2-Dimethylpropyl)-5-[trans-2-(3-chloro-4-bromophenyl)cyclopropyl]penta-2,4-dienamide (compound 71)

Preparation by analogy with Example 14 using hydrochloric acid and cuprous chloride in place of hydrobromic acid and cuprous bromide.

(±)-(2E,4E) N-Isobutyl-3-methyl-5-[trans-2-(3-chloro-4-bromophenyl)cyclopropyl]penta-2,4-diamide (compound 72) was prepared in an analogous manner using triethyl 3-methyl-4-phosphonocrotonate and isobutylamine in place of triethyl 4-phosphonocrotonate and 1,2-dimethylpropylamine.

(±)-(2E,4E)-(1,2-Dimethylpropyl)-5-[trans-2-(3-bromo-4-chlorophenyl)cyclopropyl]penta-2,4-dienamide (compound 73) and (±)-(2E,4E) N-Isobutyl-3-methyl-5-[trans-2-(3-bromo-4-chlorophenyl) cyclopropyl] penta-2,4-dienamide (compound 74) were prepared in an analogous manner starting from 4-chloro-3-nitrotoluene.

EXAMPLE 22

(±)-(2E,4E)
N-Isobutyl-3-methyl-5-[trans-2-(4-benzylphenyl)cyclopropyl]penta-2,4-dienamide (compound 75)

Powdered zinc (12.5 g) (ex BDH) in water (15 ml) at 25° was treated with mercuric chloride (1.25 g) (ex Aldrich). Concentrated hydrochloric acid was added and excess water decanted. 4-Benzoylbenzoic acid (5 g) (ex Lancaster) was added, followed by water (15 ml) glacial acetic acid (2 ml) and toluene (15 ml). A further 20 ml of concentrated hydrochloric were added. After 7 hours at reflux the mixture was filtered and washed with dilute hydrochloric acid. Work up in the usual manner gave 4-benzylbenzoic acid (4 g).

The above acid (4 g) was dissolved in ethanol (50 ml) and treated with concentrated sulphuric acid (0.5 ml). After 3 hours at reflux the mixture was concentrated in vacuo and the residue worked up in the normal manner to give ethyl-4-benzylbenzoate (4 g). NMR $^1$H 8.00(2H,dd), 7.28(7H,m), 4.39(2H,q), 4.04(2H,s), 1.40(3H,t).

The above ester (4 g) in dry ether under nitrogen at 0° was treated with lithium aluminium hydride (0.9 g). After 1 hour at 0° and 18 hours at 25° water was added carefully and the mixture worked up in the usual manner to give 4-benzylbenzyl alcohol (2.52 g). NMR $^1$H: 7.21(9H,m), 4.53(2H,s), 3.95(2H,s), 2.10(1H,bs).

The above alcohol (2.52 g) was oxidised using the conditions of Swern (oxalyl chloride, 1.2 ml; dimethyl sulphoxide, 1.8 ml; triethylamine, 8.8 ml) in dichloromethane to give 4-benzylbenzaldehyde (1.33 g). NMR $^1$H: 9.93(1H,s), 7.78(2H,d), 7.33(2H,d), 7.20(5H,s), 4.04(2H,s).

The above aldehyde was converted into the title compound by analogy with example 15.

(±)-(2E,4E) N-(1,2-Dimethylpropyl)-5-[trans-2-(4-benzylphenyl)cycloprppyl]penta-2,4-dienamide (compound 76) was prepared in an anlaogous manner using triethyl-4-phosphonocrotonate and 1,2-dimethylpropylamine.

EXAMPLE 23

(±)-(2Z,4E) N-Isobutyl-2-fluoro-3-methyl-5-[trans-2-(3,4-dichlorophenyl)cyclopropyl]penta-2,4-dienamide (compound 77)

Ethyl bromofluoroacetate (ex Fluorochem) (25 g) and triethyl phosphite (ex Aldrich) (29 g) were heated together at 140-5° for 6 hours in a vessel equipped with a fractionating column. When all the ethyl bromide had distilled off the residue was distilled to give triethyl 2-fluoro-2-phosphoacetate (22 g) (bp 98°-108° at 0.8 mm). The latter (20 g) was added dropwise to hexane washed sodium hydride (3.3 g of 60% dispersion) in dry ether (85 ml). After 3 hours at room temperature and 30 mins under reflux, acetone (6.1 ml) was added and the mixture stirred for 4 days at room temperature under nitrogen. After conventional work up the crude product was distilled to give ethyl 2-fluoro-3-methyl-but-2-enoate (4 g) (bp. 60-2° at 15 mm). (Ref. Machleidt and Wessendorf, Ann. 674, 1, (1964)).

Ethyl 2-fluoro-3-methyl-but-2-enoate (4 g.27.4 mmol), N-bromosuccinimide (5.36 g, 30 mmol) (ex Aldrich) and benzoyl peroxide (30 mg) were heated together under reflux in tetrachloromethane (60 ml) under illumination from a bright light. After 2 hours the solvent was removed and the residue taken up in hexane, filtered through "celite" and concentrated. Short path distillation gave a mixture of (E) and (Z) ethyl 4-bromo-2-fluoro-3-methylbut-2-enoates (4 g) which was heated under reflux in a Vigreaux flask with triethylphosphite (3.82 g, 23.07 mmol) at 140°-150°. After 2 hours the crude product was purified by bulb to bulb distillation to give triethyl 2-fluoro-3-methyl-4-phosphonocrotonate (3.5 g, bp 160-70° at 0.5 mm).

A solution of lithium diisopropylamide, prepared from n-butyllithium (6.25 ml) and diisopropylamine (1.4 ml), in THF (10 ml) at −70° under nitrogen was treated with the above phosphonocrotonate (2.82 g). After 2 hours at −70° (±)-trans-2-(3,4-dichlorophenyl)cyclopropylmethanal (2.15 g) was added. After 18 hours at 25°, water was added and the mixture worked up in the usual manner. Purification by chromatography (silica, ether/hexane) gave (±)-(2E,4E)-ethyl-2-fluoro-3-methyl-5-[trans-2-(3,4-dichlorophenyl) cyclopropyl]penta-2,4-dienoate (2.4 g). NMR $^1$H: 7.23(1H,d), 7.10(1H,d), 6.83(1H,dd), 6.75(1H,dd), 5.77 (1H,dd), 4.28(2H,q), 2.27(3H,d), 1.87(2H,m), 1.33(3H,t), 1.33(2H,m).

The above ester was converted into the title compound by analogy with example 1.

(±)-(2Z,4E) N-(2-Methylprop-2-enyl)-2-fluoro-3-methyl-5-[trans-2-(3,4-dichlorophenyl) cyclopropyl]penta-2,4-dienamide (compound 78) was prepared in an analogous manner using 2-methylprop-2-enylamine in place of isobutylamine.

EXAMPLE 24

(±)-(2E,4E) N-(1,2-Dimethylpropyl)-5-[r-1-fluoro-c-2-(3,4,5-trichlorophenyl cyclopropyl]penta-2,4-dienamide (compound 79) was prepared from the ester (Z)-ethyl-3-(3,4,5-trichlorophenyl)-2-fluoroprop-2-enoate by a method analogous to example 23. The ester was prepared by treating a suspension of sodium hydride (0.33 g) in tetrahydrofuran (10 ml) under nitrogen with diethyloxalate (1.83 g) and ethylfluoroacetate (1.33 g). After 4 hours at reflux, 3,4,5-trichlorobenzaldehyde (2.62 g) (prepared as in example 18) was added to the cooled mixture. After 18 hours at 25° water was added and the mxiture worked up in the usual manner. Purification by chromatography (silica, hexane/ether) gave (2.5 g), NMR $^1$H: 7.63 (2H,s), 6.77(1H,d), 4.35(2H,1), 1.38(3H,t).

The following compounds were made in an analogous manner starting from the aldehyde, Wittig reagent and amine indicated below

| Compound No. | Compound Name |
|---|---|
| 80 | (±)-(2E,4E) N-Isobutyl-3-methyl-5-[r-1-fluoro-c-2-(3,4,5-trichlorophenyl)cyclopropyl]penta-2,4-dienamide. |
| 81 | (±)-(2E,4E) N-(1,2-Dimethylpropyl)-5-[r-1-fluoro-c-2-(3,4-dichlorophenyl)cyclopropyl]penta-2,4-dienamide. |
| 82 | (±)-(2E/Z,4E) N-(2-Methylprop-2-enyl)-3-methyl-5-[r-1-fluror-c-2-(3,4-dibromophenyl)cyclopropyl]penta-2,4-dienamide, 5:4 mixture of 2E:2Z isomers. |
| 83 | (±)-(2E/Z,4E) N-Isobutyl-3-methyl-5-[r-1-fluror-c-2-(3,4-dibromophenyl)cyclopropyl]penta-2,4-dienamide, 1:1 mixutre of 2E:2Z isomers. |
| 84 | (±)-(2E,4E) N-(1,2-Dimethylpropyl)-5-[r-1-fluoro-c-2-(3,4-dibromophenyl)cyclopropyl]penta-2,4-dienamide. |
| 85 | (±)-(2E/Z,4E) N-Isobutyl-5-[r-1-fluoro-c-2-(3,4-dichlorophenyl)cyclopropyl]-3-methylpenta-2,4-dienamide, 4:1 mixture of 2E,4E:2Z,4E isomers. |
| 86 | (±)-(2E/Z,4E) N (2,2-Dimethylpropyl)-3-methyl-5-[r-1-fluoro-c-2-(3,4-dichlorophenyl)cyclopropyl]penta-2,4-dienamide, 2:1 mixture of the 2E,4E:2Z,4E isomers. |
| 87 | (±)-(2E/Z,4E) N-(2-Methylprop-2-enyl)-3-methyl-5-[r-1-fluoro-c-2-(3,4,5-trichlorophenyl)cyclopropyl]penta-2,4-dienamide. |
| 88 | (±)-(2Z,4E N-Isobutyl-3-methyl-5-[r-1-fluoro-c-2-(3,4,5-trichlorophenyl)cyclopropyl]penta-2,4,-dienamide. |
| 101 | (±)-(2E/Z,4E) N-Isobutyl-3-methyl-5-[r-1-fluoro-c-2-(3-chloro-4-bromophenyl)cyclopropyl]penta-2,4-dienamide, 1:1 mixture of 2E,4E:2Z,4E isomers. |

-continued

| | |
|---|---|
| 102 | (±)-(2E/Z,4E) N-(2-Methylprop-2-enyl)-3-methyl-5-[r-1-fluoro-c-2-(3-chloro-4-bromophenyl)cyclopropyl]penta-2,4-dienamide, 2:1 mixture of 2E,4E:2Z,4E isomers. |
| 103 | (±)-(2Z,4E) N-(2-Methylprop-2-enyl)-3-methyl-5-[r-1-fluoro-c-2-(3-chloro-4-bromophenyl)cyclopropyl]penta-2,4-dienamide. |
| 104 | (±)-(2E,4E) N-Isobutyl-2-fluoro-3-methyl-5-[r-1-fluoro-c-2-(3-chloro-4-bromophenyl)cyclopropyl]penta-2,4-dienamide. |
| 105 | (±)-(2E/Z,4E) N-(2-Methylprop-2-enyl)-2-fluoro-3-methyl-5-[r-1-fluoro-c-2-(3-chlro-4-bromophenyl)cyclopropyl]penta-2,4-dienamide. |
| 92 | (±)-(2E/Z,4E) N-(2-Methylprop-2-enyl)-3-methyl-5-[r-fluoro-c-2-(3,4-dichlorophenyl)cyclopropyl]penta-2,4-dienamide. |
| 109 | (±)-(2E/Z,4E) N-(2-Butyl)-2-fluoro-3-methyl-5-[r-1-fluoro-c-2-(3,4-dichlorophenyl)cyclopropyl]penta-2,4-dienamide, 7:1 mixture of 2Z:2E isomers. |
| | 110 (±)-(2E/Z,4E) N-(2-Methylprop-2-enyl)-2-fluoro-3-methyl-5-[r-1-fluoro-c-2-(3,4-dichlorophenyl)cyclopropyl]penta-2,4-dienamide, 6:1 mixture of 2Z:2E isomers. |
| 111 | (±)-(2E/Z,4E) N-Isobutyl-2-fluoro-3-methyl-5-[r-1-fluoro-c-2-(3,4-dichlroophenyl)cyclopropyl]penta-2,4-dienamide, 3:1 mixture of 2Z:2E isomers. |
| 112 | (±)-(2E/Z,4E) N-(2-Butyl)-3-methyl-5-[r-1-fluoro-c-2-(3,4-dichlorophenyl)cyclopropyl]penta-2,4-dienamide, 3:2 mixture of 2E:2Z isomers. |
| 113 | (±)-(2Z,4E) N-(2-Butyl)-3-methyl-5-[r-1-fluoro-c-2-(3,4-dichlorophenyl)cyclopropyl]penta-2,4-dienamide. |
| 114 | (±)-(2E/Z,4E) N-(2-Butyl-3-methyl-5-[r-1-fluoro-c-2-(3,4-dibromophenyl)cyclopropyl]penta-2,4-dienamide, 5:1 mixture of 2E:2Z isomers. |
| 115 | (±)-(2E/Z,4E) N-Isobutyl-1-fluoro-3-methyl-5-[r-1-fluoro-c-2-(3,4-dibromophenyl)cyclopropyl]penta-2,4-dienamide, 6:1 mixture of 2Z:2E isomers. |
| 116 | (±)-(2E/Z,4E N-(2-Methylprop-2-enyl)-2-fluoro-3-methyl-5-[r-1-fluoro-c-2-(3,4-dibromophenyl)cyclopropyl]penta-2,4-dienamide, 5:1 mixture of 2Z:2E isomers. |
| 117 | (±)-(2E/Z,4E) N-(2-Butyl)-2-fluoro-3-methyl-5-[r-1-fluoro-c-2-(3,4-dibromophenyl)cyclopropyl]penta-2,4-dienamide, 5:1 mixture of 2Z:2E isomers. |
| 118 | (±)-(2E,4E) N-Isobutyl-5-[r-1-fluoro-c-2-(3,4-dibromophenyl)cyclopropyl]penta-2,4-dienamide. |

| Compound No. | Aldehyde RCHO where R = | Wittig reagent | Amine |
|---|---|---|---|
| 80 | 3,4,5-Cl$_3$Ph | (2) | isobutylamine |
| 81 | 3,4-Cl$_2$Ph | (1) | 1,2-dimethylpropylamine |
| 82 | 3,4-Br$_2$Ph | (2) | 2-methylprop-2-enylamine |
| 83 | 3,4-Br$_2$Ph | (2) | isobutylamine |
| 84 | 3,4-Br$_2$Ph | (1) | 1,2-dimethylpropylamine |
| 85 | 3,4-Cl$_2$Ph | (2) | isobutylamine |
| 86 | 3,4-Cl$_2$Ph | (2) | 2,2-dimethylpropylamine |
| 87 | 3,4,5-Cl$_3$Ph | (2) | 2-methylprop-2-enylamine |
| 88 | 3,4,5-Cl$_3$Ph | (2) | isobutylamine |
| 101 | 3-Cl,4-BrPh | (2) | isobutylamine |
| 102 | 3-Cl,4-BrPh | (2) | 2-methylprop-2-enylamine |
| 103 | 3-Cl,4-BrPh | (2) | 2-methylprop-2-enylamine |
| 104 | 3-Cl,4-BrPh | (3) | isobutylamine |
| 105 | 3-Cl,4-BrPh | (3) | 2-methylprop-2-enylamine |
| 92 | 3,4-Cl$_2$Ph | (2) | 2-methylprop-2-enylamine |
| 109 | 3,4-Cl$_2$Ph | (3) | sec-butylamine |
| 110 | 3,4-Cl$_2$Ph | (3) | 2-methylprop-2-enylamine |
| 111 | 3,4-Cl$_2$Ph | (3) | isobutylamine |
| 112 | 3,4-Cl$_2$Ph | (2) | sec-butylamine |
| 113 | 3,4-Cl$_2$Ph | (2) | sec-butylamine |
| 114 | 3,4-Br$_2$Ph | (2) | sec-butylamine |
| 115 | 3,4-Br$_2$Ph | (3) | isobutylamine |
| 116 | 3,4-Br$_2$Ph | (3) | 2-methylprop-2-enylamine |
| 117 | 2,4-Br$_2$Ph | (3) | sec-butylamine |
| 118 | 3,4-Cl$_2$Ph | (1) | isobutylamine |

Wittig reagent 3 = triethyl 2-fluoro-3-methylphosphonocrotonate

EXAMPLE 25

(±)-(2E,4E)
N-(1,2-Dimethylpropyl)-5-[r-1-chloro-c-2-(3,4-dichlorophenyl)cyclopropyl]penta2,4-dienamide (compound 89).

Carboethoxymethylenetriphenylphosphorane (34.8 g) in dichloromethane (100 ml) under nitrogen at −70° was treated with triethylamine (10.1 g) and then with a solution of chlorine (7 g) dissolved in carbon tetrachloride (100 ml) over sixty minutes. The solution was warmed to 25° and water was added and the mixture worked up in the usual manner to give carboethoxychloromethylenetriphenylphosphorane (18.9 g) after recrystallistion from acetone/hexane. (Reference: Denney and Ross, J. Org. Chem., 1962, 27, 998).

Carboethoxychloromethylenetriphenylphosphorane (8.74 g) in dichloromethane (100 ml) under nitrogen at 25° was treated with 3,4-dichlorobenzaldehyde. After 18 hours at 25° removal of solvent in vacuo was followed by trituration from hexane and the hexane washings were concentrated in vacuo. Purification by chromatography (silica; ether/hexane) gave ethyl-3-(3,4-dichlorophenyl)-2-chloroprop-2-enoate (6.3 g).

The above ester was converted into the title compound by analogy with example 24.

(±)-(2E,4E) N-Isobutyl-3-methyl-5-[r-1-chloro-c-2-(3,4-dichlorophenyl)cyclopropyl]penta-2,4-dienamide (compound 90) and (±)-(2Z,4E)-N-isobutyl-3-methyl-5-[r-1-chloro-c-2-(3,4-dichlorophenyl)cychlopropyl]-penta-2,4-dienamide (compound 91) were prepared in a analogous manner using triethyl-4-phosphono-3-methylcrotonate and isobutylamine in place of triethyl-4-phosphonocrotonate and 1,2-dimethylpropylamine.

EXAMPLE 26

(±)-(2E,4E)
N-Isobutyl-5-[trans-2-(3,4-dichlorophenyl)cyclopropyl]penta-2,4-dienethioamide (compound 106)

Trans-2-(3,4-dichlorophenyl)cyclopropanemethane methanol (3 g) (prepared in Example 18) was treated with carboethoxymethylenetriphenylphosphorane (4.85 g) in dichloromethane (30 ml). Concentration in vacuo and filtration followed by concentration gave (±)-ethyl-3-[trans-2-(3,4-dichlorophenyl)cyclopropyl]prop-2-enoate (1.8 g).

Treatment of the above ester (1.8 g) with diisobutylaluminium hydride (12.6 ml of a 1M solution in hexane) in dichloromethane (100 ml) gave, after workup in the usual manner, (±)-3-[trans-2-(3,4-dichlorophenyl)cyclopropyl]prop-2-en-1-ol (1.33 g).

The above alcohol (1.33 g) was oxidised according to the conditions of Swern (oxalyl chloride, 0.7 ml; dimethyl sulphoxide, 1.15 ml; triethylamine, 3.8 ml) in dichloromethane to give (±)-3-[trans-2-(3,4-dichlorophenyl)cyclopropyl]prop-2-en-1-al which was used directly in the next step.

N-Butyllithium (62.5 ml, 0.1 mol) was added at −70° C. to diethylmethanephosphonate (15.2 g. 0.1 mol) in tetrahydrofuran (200 ml). After 30 minutes, isobutylisothiocyanate (5.8 g. 0.05 mol) in tetrahydrofuran (50 ml) was added. The mixture was left overnight at room temperature then poured onto ice-water and extracted with ether. The ether solution was washed with brine and dried and the solvents were removed to give N-Isobutyl-2-(diethoxyphosphonyl)acetothioamide.

N-isobutyl-2-(diethoxyphosphoryl) acetothioamide (0.7 g) in tetrahydrofuran (5 ml) was added at −70° to lithium diisopropylamide (5.4 mmoles) in tetrahydrofuran (15 ml). The temperature of the mixture was allowed to reach −20° C. and recooled to −40° C.

(±)-3-[trans-2-(3,4-dichlorophenyl)cyclopropyl]-prop-2-enal prepared previously in tetrahydrofuran (5 ml) was added. The mixture was left overnight at room temperature and worked up in the standard manner. The crude material was purified by column chromatrography (silica; 7:3 hexane: ether) to give the title compound.

(±)-(2E,4E) N-(1,2-Dimethylpropyl)-5-[trans-2-(3,4-dichlorophenyl)cyclopropyl]penta-2,4dien ethioamide (compound 107) was prepared in an analogous manner using N-(1,2-dimethylpropyl)-2-(diethoxyphosphoryl)acetothioamide in place of N-isobutyl-2-(diethoxyphosphoryl)acetothioamide.

(±)-(2E,4E) N-(1,2-Dimethylpropyl)-5-[c-2-(3,4-dichlorophenyl)-r-1-fluorocyclopropyl]penta-2,4-dienethioamide (compound 108) was prepared in an analogous manner using (c-2-(3,4-dichlorophenyl)-r-1-fluorocyclopropyl)methane methanol in place of trans-2-(3,4-dichlorophenyl)cyclopropylmethane methanol by an analogy with Example 24.

TABLE 2
$H^1$ NMR Data:

| Compound No. | |
|---|---|
| 1 | 7.40(2H, d), 7.20(1H, dd), 6.95(2H, d), 6.27(1H, dd), 5.75(1H, d), 5.70(1H, dd), 5.25(1H, d), 3.98(1H, m), 2.00(1H, m), 1.74(2H, m), 1.35(1H, m), 1.25(1H, m), 1.11(3H, d), 0.91(6H, dd). |
| 2 | 7.48(2H, d), 7.19(1H, dd), 6.94(2H, d), 6.25(1H, dd), 5.75(1H, d), 5.71(1H, dd), 5.50(1H, d), 3.18(2H, dd), 2.02(1H, m), 1.81(1H, m), 1.70(1H, m), 1.32(1H, m), 1.23(1H, m), 0.94(6H, d). |
| 3 | 7.68(1H, s), 7.50(2H, s), 7.20(1H, dd), 6.29(1H, dd), 5.77(1H, d), 5.73(1H, dd), 5.25(1H, d), 3.98(1H, m), 2.19(1H, m), 1.86(1H, m), 1.74(1H, m), 1.44(1H, m), 1.37(1H, m), 1.13(3H, d), 0.93(6H, dd). |
| 4 | 7.79(3H, m), 7.55(1H, m), 7.45(2H, m), 7.23(2H, m), 6.27(1H, dd), 5.78(1H, dd), 5.74(1H, d), 5.24(1H, d), 3.98(1H, m), 2.21(1H, m), 1.87(1H, m), 1.72(1H, m), 1.51(1H, m), 1.28(1H, m), 1.10(3H, d), 0.91(6H, dd). |
| 5 | 7.82(3H, m), 7.58(1H, m), 7.46(2H, m), 7.26(2H, m), 6.30(1H, dd), 5.79(1H, dd), 5.75(1H, d), 5.48(1H, m), 3.19(2H, d), 2.23(1H, m), 2.88(1H, m), 1.56(1H, m), 1.28(1H, m), 0.98(9H, s). |
| 6 | 7.80(3H, m), 7.54(1H, m), 7.45(2H, m), 7.22(1H, m), 6.20(1H, d), 5.77(1H, dd), 5.60, 5.51(1H, s), 5.50(1H, m), 3.15(2H, dd), 2.31, 1.97(3H, s), 2.22(1H, m), 1.86(2H, m), 1.47(1H, m), 1.25(1H, m), 0.93(6H, dd). |
| 7 | 7.40(2H, d), 7.21(1H, dd), 6.96(1H, d), 6.27(1H, dd), 5.81(1H, d), 5.71(1H, dd), 5.47(1H, m), 3.17(1H, d), 2.02(1H, m), 1.73(1H, m), 1.36(1H, m), 1.24(1H, m), 0.93(9H, s). |
| 8 | 7.41(2H, d), 6.98(2H, d), 6.18(1H, d), 5.68(1H, dd). 5.62, 5.50(1H, s), 5.50(1H, m), 3.16(2H, dd), 2.28, 1.98(3H, s), 2.00(1H, m), 1.79(2H, m), 1.27(2H, m), 0.94(6H, d). |
| 9 | 7.69(1H, s), 7.51(2H, s), 6.20(1H, d), 5.68(1H, dd), 5.63, 5.50(1H, s), 5.50(1H, m), 3.15(2H, dd), 2.28, 1.98(3H, s), 2.17(1H, m), 1.82(2H, m), 1.40(2H, m), 0.94(6H, d). |
| 10 | 7.56(2H, d), 7.28(1H, dd), 7.17(2H, d), 6.27(1H, dd), 5.75(1H, d), 5.72(1H, dd), 5.28(1H, d), 3.97(1H, m), 2.08(1H, m), 1.74(2H, m), 1.41(1H, m), 1.30(3H, m), 1.11(3H, d), 0.92(6H, d). |
| 11 | 7.53(2H, d), 7.18(2H, d), 6.19(1H, d), 5.68(1H, dd), 5.61(1H, s), 5.51(1H, bt), 3.14(2H, t), 2.28(3H, s), 2.08(1H, m), 2.83(2H, m), 1.40(1H, m), 1.31(H, m), 0.93(6H, d). |
| 12 | 7.19(1H, dd), 7.02(2H, d), 6.83((2H, d), 6.21(1H, dd), 5.73(1H, dd), 5.71(1H, d), 5.20(1H, d), 3.98(1H, m), 3.79(3H, s), 2.01(1H, m), 1.69(2H, m), 1.29(1H, m), 1.15(1H, m), 1.08(3H, d), 0.91(6H, d). |
| 13 | 7.21(1H, dd), 7.12(4H, m), 6.29(1H, dd), 5.77(1H, d), 5.73(1H, dd), 5.30(1H, d), 4.00(1H, m), 2.11(1H, m), 1.75(2H, m), 1.37(1H, m), 1.26(1H, m), 1.10(2H, d), 0.91(6H, d). |
| 14 | 7.14(3H, m), 6.79(1H, dd), 6.25(1H, dd), 5.75(1H, d), 5.75(1H, dd), 5.21(1H, d), 3.98(1H, m), 2.15(1H, m), 1.72(2H, m), 1.32(1H, m), 1.21(1H, m), 1.09(3H, d), 0.91(6H, d). |
| 15 | 7.25(1H, s), 7.19(1H, d), 6.80(1H, dd), 6.17(1H, d), 5.69(1H, dd), 5.61(1H, s), 5.46(1H, t), 3.12(2H, t), 2.23(3H, s), 2.11(1H, m), 1.73(2H, m), 1.28(1H, m), 1.20(1H, m), 0.91(6H, d). |
| 16 | 7.43(1H, t), 7.18(1H, dd), 6.78(2H, m), 6.23(1H, dd), 5.72(1H, d), 5.70(1H, dd), 5.23(1H, d), 4.00(1H, m), 2.02(1H, m), 1.75(2H, m), 1.28(2H, m), 1.12(3H, d), 0.91(6H, d). |
| 17 | 7.41(1H, t), 6.79(2H, m), 6.18(1H, d), 5.63(1H, dd), 5.68(1H, s), 5.46(1H, m), 3.10(1H, t), 2.22(3H, s), 2.00(1H, m), 1.75(2H, m), 1.28(2H, m), 0.91(6H, d). |
| 18 | 7.14–7.48(5H, m), 6.27(1H, dd), 5.75(1H, d), 5.71(1H, dd), 5.49(1H, m), 3.14(2H, d), 2.10(1H, m), 1.80(1H, m), 1.40(1H, m), 1.30(1H, m), 0.91(6H, dd). |
| 19 | 7.15–7.5(5H, m), 6.28(1H, d), 5.77(1H, d), 5.73(1H, dd), 5.28(1H, d), 3.99(1H, m), 2.12(1H, m), 1.78(2H, m), 1.41(1H, m), 1.28(1H, m), 1.11(3H, d), 0.92(6H, dd). |

TABLE 2-continued

H¹ NMR Data:

| Compound No. | |
|---|---|
| 20 | 7.32-7.48(1H, m), 6.20(1H, d), 5.68(1H, dd), 5.62-5.50(1H, m), 5.50(1H, m), 3.16(2H, dd), 2.28-1.96(3H, s), 2.10(1H, m), 1.81(2H, m), 1.41(1H, m), 1.28(1H, m), 0.95(6H, d). |
| 21 | 7.24-7.60(4H, m), 6.22(1H, d), 5.21(1H, dd), 5.73-5.51(1H, s), 5.51(1H, m), 4.86(2H, s), 3.88(2H, d), 2.29-1.98(3H, s), 2.10(1H, m), 1.80(1H, m), 1.75(3H, s), 1.40(1H, m), 1.29(1H, m). |
| 22 | 7.34(1H, dd), 7.15(3H, m), 6.97(1H, dd), 6.28(1H, dd), 5.81(1H, dd), 5.76(1H, d), 5.50(1H, m), 3.18(2H, dd), 2.33(1H, m), 1.78(1H, m), 1.62(1H, m), 1.36(1H, m), 1.22(1H, m), 0.93(6H, d). |
| 23 | 7.33(1H, dd), 7.14(3H, m), 6.95(1H, dd), 6.27(1H, dd), 5.78(1H, dd), 5.73(1H, d), 5.24(1H, d), 3.99(1H, m), 2.43(1H, m), 1.68(2H, m), 1.37(1H, m), 1.23(1H, m), 1.10(3H, d), 0.92(6H, dd). |
| 24 | 7.37(1H, dd), 7.26(2H, m), 6.97(1H, dd), 6.21(1H, d), 5.78(1H, dd), 5.10-5.00(1H, s), 5.00(1H, m), 3.15 (2H, dd), 2.32(1H, m), 2.30-1.96(3H, s), 1.81(1H, m), 1.71(1H, m), 1.28(2H, m), 0.94(6H, d). |
| 25 | 7.31-6.24(1H, d), 7.47(1H, m), 7.16(2H, m), 6.99 (1H, m), 5.78(1H, dd), 5.65, 5.52(1H, s), 5.50(1H, m), 4.85(2H, s), 3.87(2H, d), 2.35(1H, m), 2.30-1.97(3H, s), 1.83(1H, m), 1.60(1H, m), 1.75(3H, s), 1.35(1H, m), 1.25(1H, m). |
| 26 | 7.13-7.32(3H, m), 7.07(2H, dd), 6.17(1H, d), 5.69 (1H, dd), 5.59, 5.50(1H, s), 5.50(1H, m), 3.12(2H, dd), 2.27, 1.94(3H, s), 2.02(1H, m), 1.78(2H, m), 1.47(1H, m), 1.20(1H, m), 0.91(6H, d). |
| 27 | 7.12-7.36(4H, m), 7.06(2H, dd), 6.23(1H, d), 5.72 (2H, d & dd), 5.25(1H, d), 3.98(1H, m), 2.06(1H, m), 1.75(2H, m), 1.35(1H, m), 1.22(1H, m), 1.11(3H, d), 0.91(6H, dd). |
| 28 | 7.15(3H, m), 7.02(1H, d), 6.95(1H, dd), 6.23(1H, dd), 5.72(1H, d), 5.67(1H, dd), 5.21(1H, d), 3.98(1H, m), 2.01(1H, m), 1.73(2H, m), 1.35(1H, m), 1.22(1H, m), 1.11(3H, d), 0.92(6H, dd). |
| 29 | 7.20(2H, m), 7.07(1H, d), 6.97(1H, dd), 6.17(1H, d), 5.65(1H, dd), 5.58-5.46(1H, s), 5.46(1H, m). 3.16 (2H, dd), 2.28, 1.93(3H, s), 2.00(1H, m), 1.75(2H, m), 1.32(1H, m), 1.24(1H, m), 0.92(6H, d). |
| 30 | 7.32(1H, d), 7.26(1H, d), 7.15(1H, dd), 6.91(1H, dd), 6.25(1H, dd), 5.78(1H, d), 5.69(1H, dd), 5.47(1H, m), 3.21(1H, dd), 2.00(1H, m), 1.80(1H, m), 1.70(1H, m), 1.38(1H, m), 1.25(1H, m), 0.92(6H, d). |
| 31 | 7.35(1H, d), 7.16(1H, d), 6.93(1H, d), 6.17(1H, d), 5.66(1H, dd), 5.61(1H, s), 5.49(1H, m), 3.14(1H, dd), 2.28 1.94(3H, s), 1.98(1H, m), 1.82(1H. m), 1.74(1H, m), 1.73(1H, m), 1.68(1H, m), 0.93(6H, d). |
| 32 | 7.32(1H, d), 7.18(1H, dd), 7.15(1H, d), 6.92(1H, d), 6.26(1H, dd), 5.85(1H, d), 5.69(1H, dd), 5.27(1H, d), 3.98(1H, m), 2.00(1H, m), 1.73(2H, m), 1.37(1H, m), 1.28(1H, m), 1.13(3H, d), 0.91(6H, dd). |
| 33 | 7.25(2H, d), 7.23(1H, dd), 7.02(2H, d), 6.24(1H, dd), 5.75(1H, d), 5.71(1H, dd), 5.24(1H, d), 4.00(1H, m), 2.02(1H, m), 1.71(2H, m), 1.34(1H, m), 1.26(1H, m), 1.11(3H, d), 0.93(6H, dd). |
| 34 | 7.25(2H, d), 7.01(2H, d), 6.15(1H, d), 5.66(1H, dd), 5.58, 5.50(1H, s), 5.50(1H, m), 3.13(2H, dd), 2.29, 1.97(3H, s), 2.02(1H, m), 1.75(2H, m), 0.92(6H, d). |
| 35 | 7.30(1H, d), 7.30(1H, dd), 7.12(1H, d), 6.89(1H, dd), 6.16(1H, d), 5.62(1H, dd), 5.57-5.47(1H, s), 5.47 (1H, m), 4.83(2H, s), 3.83(2H, d), 2.27-1.93(3H, s), 1.97(1H, m), 1.72(3H, s), 1.21(2H, m), 1.72(1H, m). |
| 36 | 7.31(1H, d), 7.14(1H, d), 6.89(1H, dd), 6.16(1H, d), 5.63(1H, dd), 5.59(1H, m), 3.17(2H, dd), 2.24(3H, s), 1.95(1H, m), 1.70(1H, m), 1.25(2H, m), 0.98(1H, m), 0.52(2H, m), 0.21(2H, m). |
| 37 | 7.30(1H, d), 7.15(1H, d), 6.92(1H, dd), 6.15(1H, d), 5.61(1H, dd), 5.60(1H, s), 5.43(1H, bt), 3.09(2H, d), 2.26(3H, s), 1.98(1H, m), 1.71(1H, m), 1.25(2H, m), 0.91(9H, s). |
| 38 | 7.29(1H, d), 7.12(1H, d), 7.12(1H, dd), 6.88(1H, dd), 6.20(1H, dd), 5.70(1H, d), 5.66(1H, dd), 5.14(1H, s), 2.37(1H, h), 1.98(1H, m), 1.71(1H, m), 1.29(6H, s), 1.25(2H, m), 0.86(6H, d). |
| 39 | 7.31(1H, d), 7.19(1H, dd), 7.11(1H, d), 6.91(1H, dd), 6.23(1H, dd), 5.73(1H, d), 5.67(1H, dd), 5.21(1H, d), 4.01(1H, m), 2.01(1H, m), 1.71(1H, m), 1.48(2H, m), 1.30(2H, m), 1.13(3H, d), 0.91(3H, t). |
| 40 | 7.31(2H, d), 7.20(2H, dd), 7.11(1H, d), 6.88(1H, dd), 6.23(1H, dd), 5.78(2H, d), 5.73(1H, m), 5.69(1H, dd), 3.35(2H, d), 3.19(3H, s), 1.99(1H, m), 1.69(1H, m), 1.23(2H, m), 1.13(6H, s). |
| 41 | 7.29(1H, d), 7.21(1H, dd), 7.13(1H, d), 6.88(1H, dd), 6.22(1H, dd), 5.73(1H, d), 5.68(1H, dd), 5.60(1H, m), 3.94(4H, m), 3.48(2H, d), 1.98(1H, m), 1.73(1H, m), 1.32(3H, s), 1.28(2H, m). |
| 42 | 7.29(1H, d), 7.21(1H, dd), 7.13(1H, d), 6.88(1H, dd), 6.10(1H, dd), 6.05(1H, dd), 5.55(1H, m), 3.00(2H, d), 1.98(1H, m), 1.73(1H, m), 1.28(2H, m), 1.10(9H, s). |
| 43 | 7.29(1H, d), 7.21(1H, dd), 7.13(1H, d), 6.88(1H, dd), 6.25(1H, dd), 5.76(1H, d), 5.70(1H, d), 5.54(1H, m), 3.18(2H, dd), 1.98(1H, m), 1.68(1H, m), 1.28(2H, m), 0.94(1H, m), 0.48(2H, m), 0.20(2H, m). |
| 44 | 7.19(1H, dd), 6.26(1H, dd), 5.88(1H, d), 5.76(1H, d), 5.63(1H, dd), 5.25(1H, d), 3.99(1H, m), 1.73(3H, m), 1.13(6H, d), 1.13(1H, m), 0.9(6H, dd), 0.90(1H, m). |
| 45 | 7.27(6H, m), 6.39(1H, dd), 5.89(1H, d), 5.86(1H, d), 5.68(1H, dd), 3.96(1H, m), 2.76(1H, m), 2.58(1H, ddd), 1.72(1H, m), 1.12(3H, d), 0.92(6H, dd). |
| 46 | 7.46(2H, d), 7.18(1H, dd), 7.10(2H, d), 6.37(1H, dd), 5.89(1H, d), 5.82(1H, dd), 5.67(1H, d), 3.93(1H, m), 2.70(1H, dd), 2.52(1H, m), 1.72(1Hm, ), 1.10(3H, d), 0.91(6H, dd). |
| 47 | 7.46(2H, d), 7.12(2H, d), 6.30(1H, d), 5.80(2H, dd), 5.71(1H, s), 5.71(1H, bt), 3.14(1H, t), 2.70(1H, dd), 2.54(1H, ddd), 2.30(3H, s), 1.80(1H, m), 0.93(6H, d). |
| 48 | 7.30(5H, m), 6.17(1H, m), 5.97(1H, dd), 5.75(1H, dd), 5.31(1H, m), 3.98(1H, m), 2.27(1H, m), 1.78(2H, m), 1.20(2H, m), 1.13(1H, m), 1.00(2H, m), 0.93(6H, dd). |
| 49 | 7.40(4H, m), 6.09(1H, ddd), 5.87(1H, d), 5.10(1H, d), 3.83(1H, m), 2.55(1H, m), 2.15(1H, m), 1.66(1H, m), 1.47(1H, m), 1.27(1H, m), 1.05(3H, d), 0.85(6H, dd). |
| 50 | 7.40(4H, m), 6.94(1H, dd), 6.26(1H, dd), 5.73(1H, d), 5.62(1H, m), 5.23(1H, dd), 3.90(1H, m), 2.49(1H, dd), 1.97(1H, ddd), 1.66(1H, ), 1.41(1H, ddd), 1.17(1H, dd), 1.04(3H, d), 0.86(6H, dd). |
| 51 | 7.40(4H, m), 6.95(1H, dd), 6.26(1H, dd), 6.03(1H, bt), 5.78(1H, d), 5.25(1H, dd), 3.10(2H, m), 2.49(1H, dd), 1.98(1H, m), 1.77(1H, m), 1.42(1H, m), 1.19(1H, m), 0.89(6H, d). |
| 52 | 7.21(4H, m), 7.21-6.93(1H, dd), 6.3-6.18(1H, dd), 5.92-5.10(1H, dd), 5.71(1H, dd), 5.26(1H, m), 3.95 (1H, m), 1.73(2H, m), 1.45(1H, m), 1.13(1H, m), 1.08 (3H, d), 0.90(1H, m), 0.89(6H, dd). |
| 53 | 7.40(4H, m), 7.25(1H, dd), 6.88(1H, dd), 5.94(1H, dd), 5.78(1H, d), 5.30(1H, d), 4.00(1H, m), 2.16(1H, d), 1.88(1H, dd), 1.72(1H, m), 1.28(3H, s), 1.11(3H, d), 0.90(6H, dd), 0.89(3H, s). |
| 54 | 7.37(1H, d), 7.25(1H, d), 7.23(1H, dd), 7.03(1H, dd), 6.85(1H, dd), 5.94(1H, dd), 5.77(1H, d), 5.78(1H, d), 4.0(1H, m), 2.06(1H, d), 1.89(1H, dd), 1.75(1H, m), 1.25(3H, s), 1.12(3H, d), 0.92(6H, dd), 0.90(3H, s). |
| 55 | 7.28(2H, d), 7.28(1H, dd), 7.10(2H, d), 6.14(1H, dd), 6.82(1H, m), 6.79(1H, d), 5.37(1H, bd), 4.00(1H, m), 2.24(1H, dd), 1.73(1H, m), 1.24(1H, m), 1.11(3H, d), 0.93(6H, dd), 0.91(3H, s). |
| 56 | 7.34(1H, d), 7.15(1H, d), 6.94(1H, dd), 6.26(1H, dd), 5.26(1H, d), 5.72(1H, dd), 5.47(1H, bt), 2.18(2H, t), 2.03(1H, m), 1.81(1H, m), 1.74(1H, m), 1.34(1H, m), 1.27(1H, m), 0.93(6H, d). |
| 57 | 7.34(1H, d), 7.15(1H, d), 6.94(1H, dd), 6.26(1H, dd), 5.26(2H, d), 5.72(1H, dd), 5.47(1H, bt), 2.18(2H, t), 2.03(1H, m), 1.81(1H, m), 1.74(1H, m), 1.34(1H, m), 1.27(1H, m), 0.93(6H, d). |
| 58 | 6.91(2H, s), 6.21(1H, d), 5.60(1H, s), 5.58(1H, dd), 5.48(1H, bt), 3.11(2H, t), 2.23(3H, s), 1.94(1H, m), 1.83(1H, m), 1.80(1H, m), 1.40(2H, m), 0.90(6H, d). |
| 59 | 7.50(1H, d), 7.33(1H, d), 7.19(1H, dd), 6.90(1H, dd), 6.26(1H, dd), 5.76(1H, dd), 5.70(1H, dd), 5.22(1H, bd), 4.00(1H, m), 2.00(1H, m), 1.87(2H, m), 1.30(2H, m), 1.11(3H, d), 0.93(6H, d). |
| 60 | 7.50(1H, d), 7.33(1H, d), 6.89(1H, dd), 6.18(1H, d), |

TABLE 2-continued

H¹ NMR Data:

| Compound No. | |
|---|---|
| | 5.64(1H, dd), 5.60(1H, s), 5.43(1H, m), 3.17(2H, t), 2.28(1H, s), 1.96(1H, m), 1.81(2H, m), 1.29(2H, m), 0.94(6H, d). |
| 61 | 7.22(2H, s), 6.29(1H, d), 5.78(1H, d), 5.69(2H, dd), 5.24(1H, bd), 4.00(1H, m), 1.95(1H, m), 1.73(1H, m), 1.29(2H, m), 1.12(3H, d), 0.93(6H, dd). |
| 62 | 7.06(2H, s), 6.15(1H, d), 5.62(1H, d), 5.60(1H, s), 5.46(1H, m), 3.11(2H, t), 2.21(3H, s), 1.93(1H, m), 1.73(1H, m), 1.28(2H, m), 0.92(6H, d). |
| 63 | 7.40(2H, m), 7.20(1H, dd), 7.18(1H, d), 6.30(1H, dd), 5.78(1H, d), 5.71(1H, dd), 5.27(1H, bd), 4.00(1H, m), 2.10(1H, m), 1.75(2H, m), 1.32(2H, m), 1.11(3H, d), 0.93(6H, dd). |
| 64 | 7.38(2H, m), 7.13(1H, dd), 6.13(1H, d), 5.61(1H, dd), 5.58(1H, s), 5.50(1H, m), 3.09(2H, t), 2.22(3H, s), 2.02((1H, m), 1.75(2H, m), 1.30(2H, m), 0.90(6H, d). |
| 65 | 7.47(2H, d), 7.43(1H, s), 7.20(1H, dd), 7.06(2H, d), 6.26(1H, dd), 5.74(1H, d), 5.72(1H, dd), 5.27(1H, d), 3.99(1H, m), 2.06(1H, m), 1.80(2H, m), 1.42(1H, m), 1.29(2H, m), 1.11(3H, d), 0.91(6H, d). |
| 66 | 7.39(2H, d), 7.20(1H, dd), 7.03(2H, d), 6.26(1H, dd), 5.76(1H, d), 5.71(1H, dd), 5.27(1H, d), 3.99(1H, m), 3.08(1H, s), 2.07(1Hm,), 1.78(2H, m), 1.40(1H, m), 1.29(1H, m), 1.11(3H, d), 0.92(6H, dd). |
| 67 | 7.15(1H, dd), 7.08(1H, s), 6.25(1H, dd), 5.72(1H, d), 5.63(1H, dd), 5.22(1H, d), 3.99(1H, m), 1.98(1H, m), 1.70(2H, m), 1.30(2H, m), 1.12(3H, d), 0.90(6H, dd). |
| 68 | 7.23-6.6(1H, d), 7.06(2H, s), 6.14(1H, dd), 5.58-5.20(1H, dd), 5.58(2H, m), 3.10(2H, 2t), 2.23-2.01 (3H, s), 1.95(1H, m), 1.75(2H, m), 1.28(2H, m), 0.91 (6H, 2d). |
| 69 | 7.30(1H, d), 7.14(1H, d), 6.94(1H, dd), 6.91(1H, dd), 6.01(1H, d), 5.36(1H, d), 4.76(1H, dd), 3.97(1H, m), 2.02(2H, m), 1.71(1H, m), 1.37(1H, m), 1.21(1H, m), 1.10(3H, d), 0.91(6H, dd). |
| 70 | 7.31(1H, d), 7.16(1H, d), 6.92(1H, d), 6.00(1H, d), 5.58(1H, m), 4.83(1H, dd), 3.13(2H, t), 2.23(3H, s), 2.04(2H, m), 1.79(1H, m), 1.33(1H, m), 1.08(1H, m), 0.91(6H, d). |
| 71 | 7.48(1H, d), 7.18(1H, dd), 7.10(1H, d), 6.82(1H, dd), 6.23(1H, dd), 5.72(1H, d), 5.67(1H, dd), 5.22(1H, d), 3.98(1H, m), 1.98(1H, m), 1.72(2H, m), 1.28(2H, m), 1.10(3H, d), 0.90(6H, dd). |
| 72 | 7.43(1H, d), 7.13(1H, d), 6.82(1H, dd), 6.15(1H, d), 5.61(1H, dd), 5.59(1H, s), 5.48(1H, m), 3.11(2H, t), 2.23(3H, s), 1.97(1H, m), 1.88(2H, m), 1.25(2H, m), 0.90(6H, d). |
| 73 | 7.31(1H, d), 7.23(1H, d), 7.15(1H, dd), 6.92(1H, dd), 6.23(1H, dd), 5.71(1H, d), 5.63(1H, dd), 5.27(1H, d), 3.94(1H, m), 1.98(1H, m), 1.70(2H, m), 1.25(2H, m), 1.10(3H, d), 0.89(6H, dd). |
| 74 | 7.31(2H, m), 6.92(1H, dd), 6.12(1H, d), 5.61(1H, dd), 5.60(1H, s), 5.49(1H, m), 3.12(2H, t), 2.25(3H, s), 1.96(1H, m), 1.75(2H, m), 1.30(1H, m), 1.22(1H, m), 0.91(6H, d). |
| 75 | 7.10(9H, m), 6.11(1H, d), 6.63(1H, dd), 5.57(1H, s), 5.43(1H, m), 3.91(2H, s), 3.10(2H, t), 2.26(3H, s), 1.99(1H, m), 1.78(2H, m), 1.30(1H, m), 1.17(1H, m), 0.90(6H, d). |
| 76 | 7.10(10H, m), 6.20(1H, dd), 5.69(1H, d), 5.65(1H, d), 5.19(1H, m), 3.93(2H, s), 2.01(1H, m), 1.71(2H, m), 1.32(1H, m), 1.19(1H, m), 1.13(3H, d), 0.90(6H, dd). |
| 77 | 7.31(1H, d), 7.12(1H, d), 6.89(1H, dd), 6.63(1H, d), 6.32(1H, d), 5.62(1H, dd), 3.14(2H, t), 2.24(3H, s), 1.99(1H, m), 1.82(2H, m), 1.28(2H, m), 0.92(6H, d). |
| 78 | 7.31(1H, d), 7.12(1H, d), 6.89(1H, dd), 6.67(1H, dd), 6.40(1H, m), 5.66(1H, m), 4.88(2H, s), 3.88(2H, d), 2.25(3H, s), 2.00(1H, m), 1.80(1H, m), 1.57(3H, s), 1.28(2H, m). |
| 79 | 7.21(2H, s), 7.21(1H, dd), 6.44(1H, dd), 5.85(1H, d), 5.81(1H, dd), 5.27(2H, d), 3.96(1H, m), 2.24(1H, ddd), 1.73(2H, m), 1.54(1H, m), 1.09(3H, d), 0.89(6H, dd). |
| 80 | 7.24(2H, d), 6.33(1H, d), 5.79(1H, dd), 5.70(1H, s), 5.49(1H, m), 3.11(2H, t), 2.28(1H, s), 2.22(1H, m), 1.79(1H, m), 1.70(1H, m), 1.53(1H, m), 0.91(6H, d). |
| 81 | 7.35(1H, d), 7.30(1H, d), 7.23(1H, dd), 7.07(1H, dd), 6.43(1H, dd), 5.83(1H, d), 5.81(1H, dd), 5.31(1H, d), 3.94(1H, m), 2.28(1H, m), 1.72(2H, m), 1.53(1H, ddd), 1.09(6H, dd). |
| 82 | 7.80 & 6.35(1H, d), 7.53(2H, m), 7.02(1H, dd), 6.09 (1H, dd), 5.85(1H, dd), 5.72 & 5.60(1H, s), 5.60 (1H, m), 4.81(2H, s), 3.85(2H, d), 2.38 & 2.00(3H, s), 2.30(1H, m), 1.68(3H, s), 1.65(1H, m), 1.59(1H, m). |
| 83 | 7.80 & 6.30(1H, d), 7.50(2H, m), 7.00(1H, dd), 6.00 (1H, dd), 5.80(2H, m), 5.70 & 5.60(1H, s), 3.05(2H, m), 2.24 & 1.90(3H, s), 2.23(1H, m), 1.60(3H, m), 0.90 (6H, d). |
| 84 | 7.50(2H, m), 7.20(1H, dd), 7.00(1H, dd), 6.40(1H, dd), 5.85(1H, d), 5.83(1H, dd), 5.28(1H, d), 3.95(1H, m), 2.25(1H, m), 1.25(2H, m), 1.55(1H, m), 1.10(3H, d), 0.90(6H, dd). |
| 85 | 7.75 & 6.35(1H, d), 7.38(2H, m), 7.05(1H, dd), 5.80 (1H, dd), 5.70 & 5.61(1H, s), 5.40(1H, m), 3.15(2H, m), 2.30 & 1.95(3H, s), 2.30(1H, m), 1.41-1.83(3H, m), 0.91(6H, d). |
| 86 | 7.75 & 6.35(1H, d), 7.34(3H, m), 7.04(1H, dd), 6.08 & 5.81(1H, dd), 5.71 & 5.63(1H, s), 5.44(1H, m), 3.13 (2H, d), 2.28 & 1.96(3H, s), 2.28(1H, m), 1.44-1.80(2H, m), 0.91(9H, s). |
| 87 | 7.25(2H, s), 6.37(1H, dd), 5.80(1H, dd), 5.74(1H, s), 5.54(1H, m), 4.85(2H, s), 3.88(2H, d), 2.32 & 1.98(3H, s), 2.24(1H, m), 1.75(3H, m), 1.75(2H, m), 1.55(1H, m). |
| 88 | 7.82(1H, d), 7.27(2H, m), 6.09(1H, dd), 5.63(1H, s), 5.52(1H, m), 3.12(2H, t), 2.30(1H, m), 1.98(1H, m), 1.80(1H, m), 1.65(2H, m), 0.93(6H, m). |
| 89 | 7.38(1H, d), 7.28(1H, dd), 7.22(1H, d), 7.15(1H, dd), 6.51(1H, dd), 5.84(2H, dd), 5.23(1H, d), 3.95(1H, m), 2.47(1H, dd), 1.73(3H, m), 1.09(3H, d), 0.89(6H dd). |
| 90 | 7.38(1H, d), 7.32(1H, d), 7.05(1H, dd), 6.40(1H, d), 5.83(1H, d), 5.73(1H, s), 5.43(1H, m), 3.14(2H, t), 2.44(1H, dd), 2.27(3H, s), 1.72(3H, m), 0.91(6H, d). |
| 91 | 7.89(1H, d), 7.35(2H, m), 7.07(1H, dd), 6.05(1H, d), 5.61(1H, s), 5.49(1H, m), 3.10(2H, t), 2.46(1H, m), 1.98(3H, s), 1.81(2H, m), 1.75(2H, m), 0.92(6H, m). |
| 92 | 7.81 & 6.35(1H, d), 7.37(2H, m), 7.07(1H, dd), 6.11 & 5.81(1H, dd), 5.72 & 5.64(1H, s), 5.55(1H, m), 4.85 (2H, s), 3.87(2H, m). |
| 93 | 7.50(1H, m), 7.32(1H, d), 6.88(1H, dd), 6.17(1H, d), 5.64(1H, dd), 5.61(1H, s), 5.46(1H, m), 4.82(2H, s), 3.88(2H, d), 2.25 & 2.04(3H, s), 1.93(1H, m), 1.73 (3H, s), 1.70(1H, m), 1.25(2H, m). |
| 94 | 7.32(1H, d), 7.18(1H, d), 6.92(1H, d), 6.03(1H, s), 5.61(1H, m), 4.98(1H, dd), 4.84(1H, s), 3.86(1H, d), 2.22(3H, s), 2.00(2H, m), 1.73(3H, s), 1.34(1H, m), 1.20(1H, m). |
| 95 | 7.39(1H, d), 7.21(1H, dd), 7.18(1H, d), 6.97(1H, dd), 6.30(1H, dd), 5.84(1H, d), 5.20(1H, dd), 5.42(1H, m), 3.21(2H, d), 2.03(1H, m), 1.87(1H, m), 1.19(2H, m), 0.98(9H, s). |
| 96 | 7.30(1H, d), 7.13(1H, dd), 7.09(1H, d), 6.89(1H, dd), 6.20(1H, dd), 5.69(1H, d), 5.65(1H, dd), 5.28(1H, m), 3.80(1H, m), 1.90(2H, m), 1.68(2H, m), 1.25(10H, m). |
| 97 | 7.30(1H, d), 7.13(1H, d), 6.89(1H, dd), 6.14(1H, d), 5.62(1H, dd), 5.57(1H, s), 5.20(1H, m), 3.98(1H, m), 2.24(3H, s), 1.97(1H, m), 1.71(1H, m), 1.47(2H, dq), 1.25(2H, m), 1.11(3H, d), 0.90(3H, t). |
| 98 | 7.32(1H, d), 7.16(1H, d), 6.91(1H, dd), 6.17(1H, d), 5.66(1H, dd), 5.65(1H, m), 5.58(1H, s), 3.98(4H, m), 3.48(2H, m), 2.28(3H, s), 1.98(1H, m), 1.73(1H, m), 1.32(3H, s), 1.25(2H, m). |
| 99 | 8.13(1H, d), 7.66(2H, m), 7.50(1H, d), 7.27(2H, m), 6.16(1H, d), 5.72(1H, dd), 5.55(1H, s), 5.43(1H, m), 3.12(2H, t), 2.16 & 1.95(3H, s), 2.20(1H, m), 1.84 (2H, m), 1.49(1H, m), 1.30(1H, m), 0.91(6H, d). |
| 100 | 8.13(1H, d), 7.66(2H, m), 7.50(1H, d), 7.27(2H, m), 6.16(1H, d), 5.72(1H, dd), 5.58(1H, s), 5.45(1H, m), 4.82(2H, s), 3.82(2H, d), 2.29 & 1.93(3H, s), 2.28 (1H, m), 1.85(2H, m), 1.72(3H, m), 1.50(1H, m), 1.25 (1H, m). |
| 101 | 7.7 & 6.35(1H, d), 7.5(1H, d), 7.38(1H, d), 6.99 (1H, dd), 5.80 & 6.10(1H, dd), 5.73 & 5.64(1H, s), 5.52(1H, m), 3.15(1H, m), 2.31 & 2.01(3H, s), 2.30 (1H, m), 1.4-1.9(3H, m), 0.92(3H, d). |
| 102 | 7.82 & 6.40(1H, d), 7.57(1H, d), 7.39(1H, d), 7.04 |

TABLE 2-continued

H¹ NMR Data:

| Compound No. | |
|---|---|
| | (1H, dd), 6.17 & 5.87(1H, dd), 5.74 & 5.67(1H, s), 5.57(1H, m), 4.88(2H, s), 3.89(2H, d), 2.35 & 2.01 (3H, s), 2.30(1H, m), 1.48–1.84(2H, m), 1.60 (3H, s). |
| 103 | 7.81(1H, d), 7.50(1H, m), 7.31(1H, m), 6.99(1H, dd), 6.13(1H, dd), 5.67(1H, s), 5.60(1H, m), 5.38(1H, d), 4.88(2H, s), 3.99(2H, d), 2.28(1H, m), 2.00(3H, s), 1.77(3H, s), 1.60–1.80(2H, m). |
| 104 | 7.59(1H, d), 7.39(1H, d), 7.04(1H, dd), 6.89(1H, d), 6.41(1H, m), 5.85(1H, dd), 3.19(2H, t), 2.36(3H, d), 2.30(1H, m), 1.70–1.90(2H, m), 1.60(1H, m), 0.98 (6H, d). |
| 105 | 7.54(1H, d), 7.38(1H, d), 7.00(1H, dd), 6.88(1H, d), 6.46(1H, m), 6.87(1H, dd), 4.89(1H, s), 3.91(2H, d), 2.39(3H, d), 2.35(1H, m), 1.50–1.90(2H, m), 1.79 (3H, s). |
| 106 | 7.48(1H, dd), 7.34(1H, d), 7.08(1H, m), 6.93(1H, dd), 6.29(1H, dd), 6.19(1H, d), 5.79(1H, dd), 3.62(2H, t), 2.03(2H, m), 1.74(1H, m), 1.29(2H, m), 0.98(6H, d). |
| 107 | 7.48(1H, dd), 7.35(1H, d), 6.93(1H, dd), 6.90(1H, m), 6.30(1H, d), 6.15(1H, d), 5.80(1H, dd), 4.70(1H, m), 2.00(2H, m), 1.75(1H, m), 1.30(2H, m), 1.20(3H, d), 0.95(6H, 2×d). |
| 108 | 7.55(1H, dd), 7.45(1H, d), 7.38(1H, d), 7.11(1H, dd), 6.97(1H, m), 6.50(1H, dd), 7.28(1H, d), 5.95(1H, m), 4.78(1H, m), 2.32(1H, m), 1.98(1H, m), 1.86(1H, m), 1.55(1H, m), 1.20(1H, m), 0.98(6H, 2×d). |
| 109 | 79 & 6.88(1H, d), 7.39(2H, m), 7.12(1H, dd), 6.16(1H, m), 5.89(1H, m), 4.03(1H, m), 2.38(1H, m), 2.33 & 1.97 (3H, d), 1.80(1H, ddd), 1.60(4H, m), 1.20(3H, d), 0.94(3H, t). |
| 110 | 7.9 & 6.89(1H, d), 7.39(2H, m), 7.11(1H, dd), 6.47(1H, m), 6.12 & 5.90(1H, dd), 4.90(2H, s), 4.93(2H, d), 2.32(1H, m), 2.32 & 1.96(3H, m), 1.78(3H, s), 1.80(1H, ddd), 1.60(2H, m). |
| 111 | 7.9 & 6.89(1H, d), 7.33(2H, m), 7.09(1H, dd), 6.40(1H, m), 6.10 & 5.88(1H, dd), 3.21(2H, t), 2.33 & 2.00(3H, d), 2.32(1H, m), 1.80(2H, m), 1.56(1H, m), 0.94(6H, d). |
| 112 | 7.80 & 6.36(1H, d), 7.38(2H, m), 7.08(1H, dd), 6.09 & 5.82(1H, dd), 5.69 & 5.62(1H, s), 5.77(1H, d), 3.99(1H, m), 2.32 & 1.99(3H, m), 1.73(1H, ddd), 1.50(4H, m), 1.17 (3H, d), 0.93(3H, t). |
| 113 | 7.80(1H, d), 7.35(2H, m), 7.09(1H, dd), 6.11 (1H, dd), 5.63(1H, s), 5.29(1H, d), 4.00(1H, m), 2.32 (1H, m), 2.00(1H, s), 1.40–1.80(5H, m), 1.16(3H, d), 0.96(3H, t). |
| 114 | 7.80 & 6.38(1H, d), 7.54(2H, m), 7.08(1H, dd), 6.11 & 5.83(1H, dd), 5.69 & 5.62(1H, s), 5.29(2H, d), 4.02(1H, m), 2.29 & 2.00(3H, s), 2.30(1H, m), 1.80(1H, ddd), 1.42–1.72 (4H, m), 1.16(3H, d), 0.93(3H, t). |
| 115 | 7.56(2H, m), 7.08(1H, dd), 6.88(1H, d), 6.40(1H, m), 6.12 & 5.88(1H, dd), 3.18(2H, t), 2.33 & 2.00(3H, d), 2.31(1H, m), 1.85(2H, m), 1.58(1H, m), 0.96(6H, d). |
| 116 | 7.90 & 6.92(1H, d), 7.55(2H, m), 7.04(1H, dd), 6.46 (1H, m), 6.09 & 5.89(1H, dd), 4.89(2H, s), 3.93(2H, d), 2.34 & 2.00(3H, m), 2.32(1H, m), 1.80(2H, m), 1.77(3H, s), 1.60(1H, m). |
| 117 | 7.90 & 6.87(1H, d), 7.53(2H, m), 7.06(1H, dd), 6.13 (1H, m), 6.08 & 5.87(1H, dd), 4.01(1H, m), 2.34 & 1.99 (3H, d), 2.32(1H, m), 1.80(1H, ddd), 1.50–1.80(4H, m), 1.18(3H, d), 0.93(3H, t). |
| 118 | 7.39(2H, m), 7.32(1H, dd), 7.10(1H, dd), 6.46(1H, dd), 5.90(1H, d), 5.87(1H, d), 5.08(1H, m), 3.21(2H, t), 2.31(1H, m), 1.80(2H, m), 1.58(1H, m), 0.99(6H, d). |

| Compound No. | TLC Rf | Eluant ratio* | m.pt. | Mass Spectrum M+1 | Base Peak | Diene Sterochem E/E:E/Z | Cyclpropyl Sterochem |
|---|---|---|---|---|---|---|---|
| 1 | 0.25 | 3:7 | 141.9–143.2 | | | | |
| 2 | 0.25 | 3:7 | 133.1–134.6 | | | | |
| 3 | 0.44 | ether | 153.0–155.5 | | | | |
| 4 | 0.39 | ether | 138.0–142.0 | | | | |
| 5 | 0.45 | ether | | | | | |
| 6 | 0.46 | ether | 99.5–104.0 | | | 9:1 | |
| 7 | 0.44 | ether | | | | | |
| 8 | 0.47 | ether | | | | 15:1 | |
| 9 | 0.57 | ether | 107.0–110.0 | | | 9:1 | |
| 10 | 0.4 | ether | 138.6–140° | 352 | 352 | 100% | trans |
| 11 | 0.46 | ether | 102–105° | 352 | 352 | 20:1 | trans |
| 12 | 0.38 | ether | 117–125° | 314 | 314 | 100% | trans |
| 13 | 0.35 | ether | 98.102° | 368 | 368 | 100% | trans |
| 14 | 0.40 | ether | 142.5–144.5° | 380 | 382 | 100% | trans |
| 15 | 0.51 | ether | — | 380 | 382 | 19:1 | trans |
| 16 | 0.36 | ether | 148–149° | 380 | 382 | 100% | trans |
| 17 | 0.49 | ether | 108–110° | 380 | 382 | 10:1 | trans |
| 18 | 0.20 | 1:4 | 122.0–123.0 | 338 | 338 | | |
| 19 | 0.10 | 1:5 | 120.0–121.0 | 352 | 352 | | |
| 20 | 0.15 | 1:5 | | 352 | 352 | 7:1 | |
| 21 | 0.15 | 1:5 | | 350 | 350 | 4:1 | |
| 22 | 0.35 | 2:3 | 126.0–127.0 | 304 | 304 | | |
| 23 | 0.40 | 2:3 | 128.0–129.0 | 318 | 318 | | |
| 24 | 0.40 | 2:3 | | 318 | 318 | 3:1 | |
| 25 | 0.40 | 2:3 | | 316 | 316 | 2:1 | |
| 26 | 0.40 | 2:3 | | | | 10:1 | |
| 27 | 0.40 | 2:3 | 69.7–70.7 | 284 | 284 | | |
| 28 | 0.42 | ether | 102.5–103 | | | | |
| 29 | 0.52 | ether | 92.0–97.0 | | | 15:1 | |
| 30 | 0.33 | ether | 131.0–133.0 | | | | |
| 31 | 0.52 | ether | 98.0–103.0 | | | 8:1 | |
| 32 | 0.38 | ether | 108.0–113.0 | | | | |
| 33 | 0.40 | ether | 125.0–131.0 | | | | |
| 34 | 0.52 | ether | | | | 9:1 | |
| 35 | 0.49 | ether | | 350 | 350 | 5:1 | trans |
| 36 | 0.42 | ether | | 350 | 350 | 8:1 | trans |
| 37 | 0.50 | ether | 113–115° | | | 19:1 | trans |
| 38 | 0.57 | ether | 75.6° | | | 100% | trans |
| 39 | 0.35 | ether | 76.8° | | | 100% | trans |

-continued

| Compound No. | TLC. Rf | Eluant ratio* | m.pt. | Mass Spectrum M + 1 | Base Peak | Diene Sterochem E/E:E/Z | Cyclpropyl Stereochem |
|---|---|---|---|---|---|---|---|
| 40 | 0.16 | ether | | | | 100% | trans |
| 41 | 0.16 | ether | | | | 100% | trans |
| 42 | 0.41 | ether | | | | 100% | trans |
| 43 | 0.25 | ether | 124–126° | | | 100%EE | trans |
| 44 | 0.40 | 4:6 | | 398 | 398 | 100% | trans |
| 45 | 0.35 | 4:6 | | 398 | 398 | 11:1 | trans |
| 46 | 0.30 | 4:6 | | 366 | 366 | 100% | cis/trans 1:1 |
| 47 | 0.30 | 4:6 | | 326 | 326 | | cis |
| 48 | 0.30 | 4:6 | | 352 | 352 | 100% | cis/trans 6:1 |
| 49 | 0.25 | 4:6 | | 338 | 338 | 100% | cis/trans 4:1 |
| 50 | 0.4 | 4:6 | | 332 | 332 | 100% | cis/trans 2:3 |
| 51 | 0.38 | 4:6 | 32.5–35.1° | 380 | 380 | 100% | trans |
| 52 | 0.50 | 4:6 | 49.2–51.5° | 380 | 380 | 100% | trans |
| 53 | 0.50 | 4:6 | 44.9–46.5° | 332 | 332 | 100% | trans |
| 54 | 0.45 | 1:1 | 125.8–128.5° | 338 | 338 | 100% | trans |
| 55 | 0.40 | 4:6 | 122–126° | | | 100% | trans |
| 56 | 0.29 | 4:6 | 128.2–130.1° | 353 | 353 | 19:1 | trans |
| 57 | 0.35 | ether | 142° | 440 | 214 | 100% | trans |
| 58 | 0.47 | ether | 96–99° | 440 | 114 | 19:1 | trans |
| 59 | 0.53 | ether | 157–158° | 430 | 430 | 100% | trans |
| 60 | 0.49 | ether | 130–133° | 430 | 113 | 18:1 | trans |
| 61 | 0.29 | ether | 141–142° | 386 | 386 | 100% | trans |
| 62 | 0.47 | ether | 86–91° | 386 | 214 | 9:1 | trans |
| 63 | 0.35 | 4:6 | 43.5–47.8° | 468 | 468 | 100% | trans |
| 64 | 0.4 | 4:6 | 152.5–154.3° | 308 | 308 | 100% | trans |
| 65 | 0.41 | ether | 94° | 386 | 388 | 100% | trans |
| 66 | 0.50 | ether | 116–119° | | | 5:3 | trans |
| 67 | 0.29 | ether | 148° | 370 | 370 | 100% | trans |
| 68 | 0.44 | ether | 82–83.5° | 370 | 370 | 19:1 | trans |
| 69 | 0.31 | ether | 123–125° | 396 | 113 | 100% | trans |
| 70 | 0.46 | ether | 114–116° | 396 | 141 | 12:1 | trans |
| 71 | 0.35 | ether | 134–136° | 396 | 183 | 100% | trans |
| 72 | 0.44 | ether | 113–114° | 396 | 398 | 19:1 | trans |
| 73 | 0.20 | 1:3 | | | | 23:1 | trans |
| 74 | 0.20 | 1:4 | 104–106° | | | 100% | trans |
| 75 | 0.59 | ether | | 370 | 370 | 100% | trans |
| 76 | 0.50 | ether | | 350 | 350 | 14:1 | trans |
| 77 | 0.24 | ether | 179–180° | 404 | 406 | 100% | trans |
| 78 | 0.36 | ether | 120–122° | 404 | 406 | 20:1 | trans |
| 79 | 0.25 | ether | 160–162° | 370 | 370 | 100% | trans |
| 80 | 0.40 | 1:1 | | 456 | 458 | 5:4 | trans |
| 81 | 0.40 | 1:1 | | 458 | 460 | 1:1 | trans |
| 82 | 0.29 | 1:1 | 143.4–145.2° | 458 | 460 | 100% | trans |
| 83 | 0.34 | ether | | 370 | 370 | 4:1 | trans |
| 84 | 0.42 | ether | | 384 | 384 | 2:1 | trans |
| 85 | 0.25 | ether | 156° | 386 | 388 | 100% | trans |
| 86 | 0.38 | ether | 144° | 386 | 388 | >19:1 | trans |
| 87 | 0.44 | ether | 71° | 386 | 388 | <1:19 | trans |
| 88 | 0.38 | ether | | 368 | 368 | 4:1 | trans |
| 89 | 0.36 | ether | 128° | 404 | 402 | 6:1 | trans |
| 90 | 0.55 | 1:1 | 45.6–47.5° | | | <1:19 | trans |
| 91 | 0.50 | 1:1 | | 438 | 440 | 9:2 | trans |
| 92 | 0.47 | ether | | 368 | 368 | 100% | trans |
| 93 | 0.38 | ether | | | | 100% | trans |
| 94 | 0.24 | ether | 162–164° | | | 100% | trans |
| 95 | 0.40 | ether | 106–107° | 352 | 352 | >19:1 | trans |
| 96 | 0.39 | ether | 114–116° | | | | trans |
| 97 | 0.50 | 1:1 | | 410 | 412 | 5:1 | trans |
| 98 | 0.50 | 1:1 | 93–94° | 412 | 414 | 9:1 | trans |
| 99 | 0.38 | ether | | 414 | 416 | 1:1 | trans |
| 100 | 0.38 | ether | | 412 | 414 | 2:1 | trans |
| 101 | 0.42 | ether | | 412 | 414 | <1:19 | trans |
| 102 | 0.55 | ether | | 432 | 434 | >19:1 | trans |
| 103 | 0.48 | ether | | 430 | 432 | >19:1 | trans |
| 104 | 0.24 | 1:1 | | 354 | 354 | 100% | trans |
| 105 | 0.30 | 1:1 | | 368 | 368 | 100% | trans |
| 106 | 0.36 | 1:1 | | 386 | 386 | 100% | trans |
| 109 | 0.58 | ether | | 388 | 388 | 1:7 | trans |
| 110 | 0.57 | ether | | 386 | 386 | 1:6 | trans |
| 111 | 0.59 | ether | | 388 | 388 | 1:3 | trans |
| 112 | 0.32 | ether | | 370 | 370 | 3:2 | trans |
| 113 | 0.37 | ether | | 370 | 370 | <1:19 | trans |
| 114 | 0.50 | 1:1 | 112.2° C. | 458 | 460 | 5:1 | trans |
| 115 | 0.50 | 1:1 | 104.4–107° C. | 476 | 478 | 1:6 | trans |
| 116 | 0.50 | 1:1 | | 474 | 476 | 1:5 | trans |
| 117 | 0.50 | 1:1 | | 476 | 478 | 1:5 | trans |

-continued
| Compound No. | TLC. Rf | Eluant ratio* | m.pt. | Mass Spectrum M + 1 | Base Peak | Diene Sterochem E/E:E/Z | Cyclpropyl Stereochem |
|---|---|---|---|---|---|---|---|
| 118 | 0.45 | 1:1 | 158.2–160.3° C. | 356 | 356 | 100% | trans |
*Ethylacetate:hexane
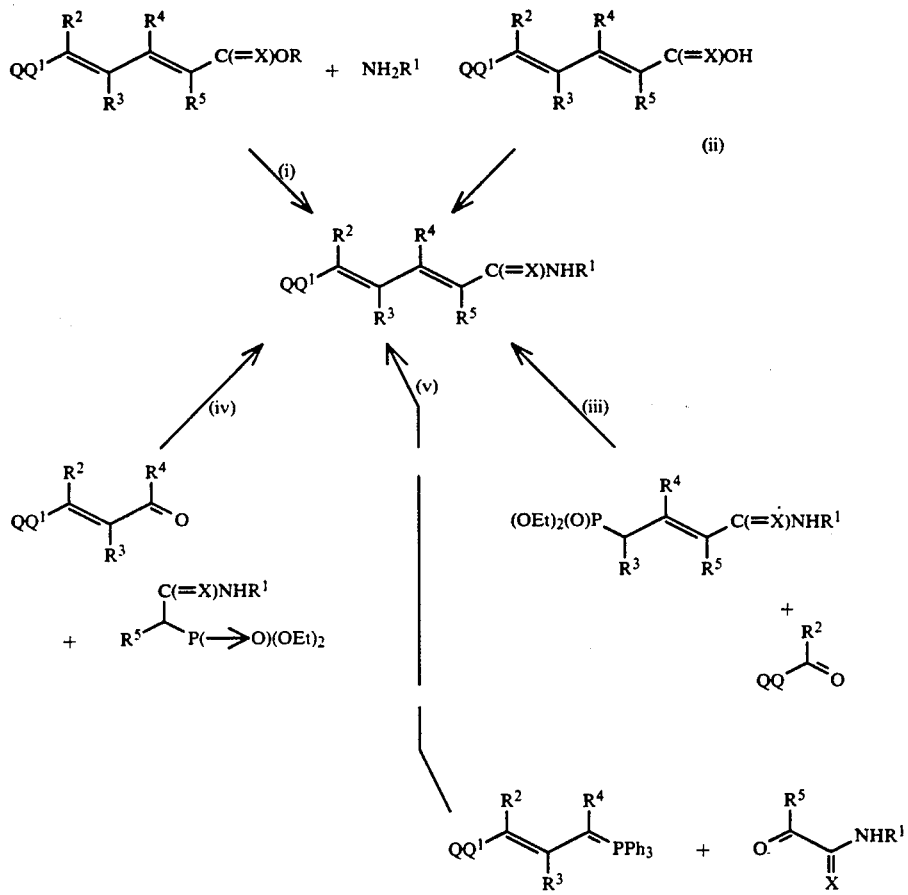
(i) Process (a) $Z^1$ = OR, X = O
(ii) Process (a) $Z^1$ = OH, X = O
(iii) Process (b) X = O,S
(iv) Process (b) X = O,S
(v) Process (b) X = O,S
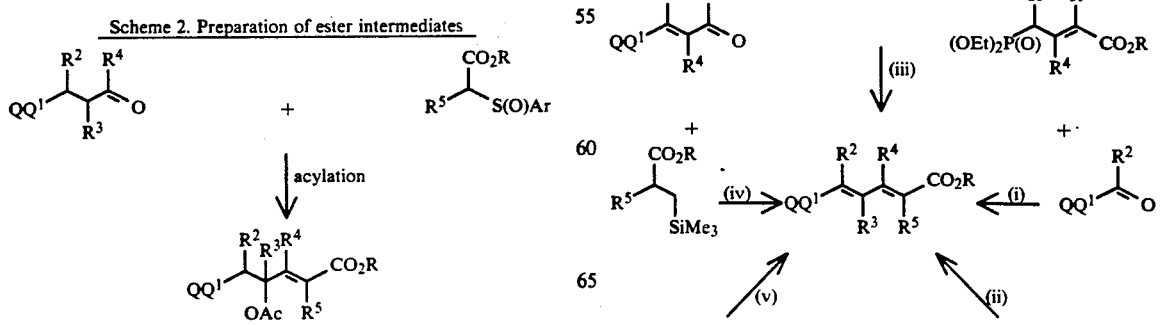

-continued
Scheme 2. Preparation of ester intermediates

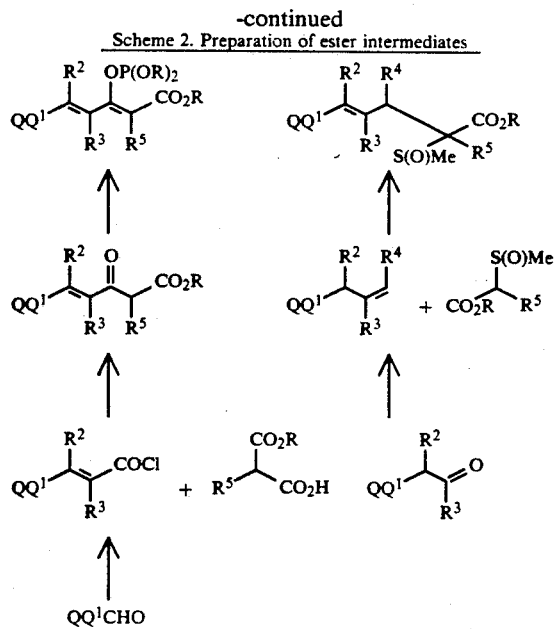

(i) to (v) denote processes (i) to (v) described hereinbefore for preparation of ester intermediates.

EXAMPLE A
Spray Tests

The activity of compounds of the invention were tested by dissolving the compounds in acetone (5%) and then diluting in water: "Synperonic" (94.5%:0.5%) to give a water emulsion. The solution was then used to treat the following insects, for which activity was observed at the following spray rates:

Musca domestica 20 female Musca were contained in a cardboard cylinder with gauze over both ends. Solution containing the compound was sprayed onto the insects so enclosed and mortality assessed after 48 hours at 25° C.

The following compounds were active at 1000 ppm or less: 1, 2, 3, 5, 6. 7, 8, 10, 11, 14, 15, 19, 20, 21, 36, 37, 38, 39, 40, 41, 96, 48, 55, 57, 65, 66, 78.

The following compounds were active at 200 ppm or less: 4, 9, 13, 16, 17, 100, 30, 31, 32, 33, 34, 35, 42, 95, 97, 56, 59, 60, 61, 62, 63, 64, 67, 68, 69, 70, 71, 72, 73, 74, 77, 93, 94, 79, 80, 81, 82, 83, 84, 85, 86, 89, 90, 92, 87.

Pluetella xylostella

Chinese cabbage leaf discs infested with 8 2nd instar Plutella larvae were sprayed with the solution containing the compound. Mortality was assessed after 2 days at 25° C.

The following compounds were active at 1000 ppm or less: 12, 22, 25, 26, 45, 46, 47, 48, 51, 52, 53, 54, 58, 65, 76.

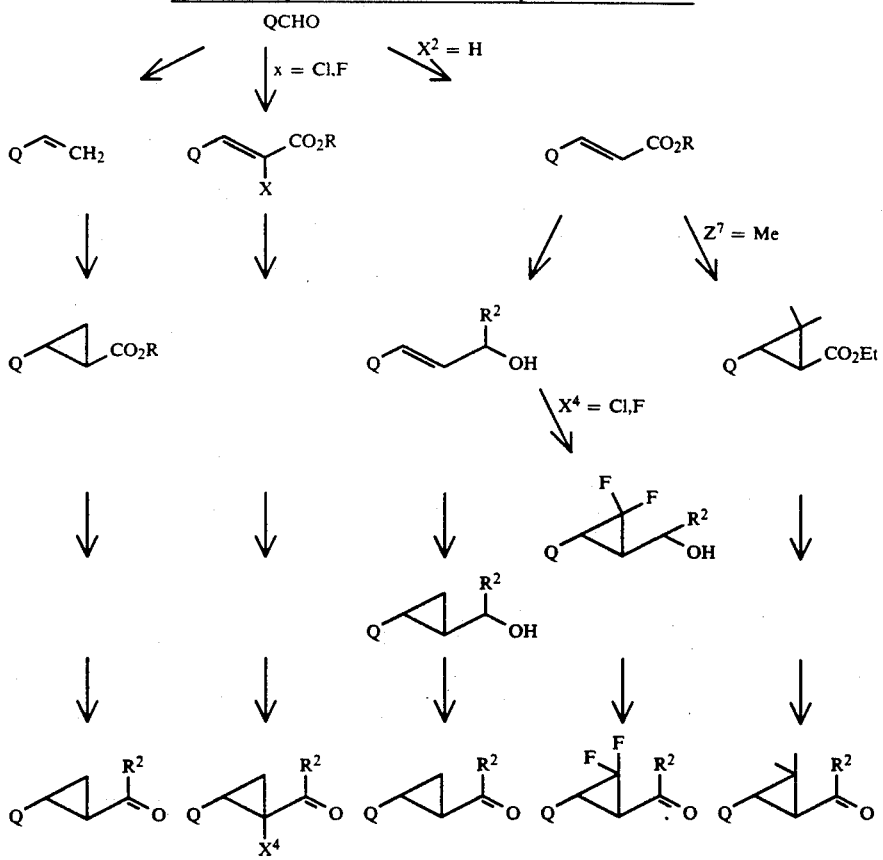

Scheme 3 Preparation of alcohol and aldehyde intermediates.

BIOLOGICAL DATA

The following examples illustrate, in a non-limiting manner, the pesticidal acitivity of compounds of formula (I):

The following compounds were active at 200 ppm or less: 1, 2, 3, 4, 5, 6, 7, 9, 11, 13, 14, 15, 18, 19, 20, 21, 23, 24, 27, 28, 29, 30, 31, 32, 34, 36, 41, 42, 95, 44, 50, 57, 61, 66.

The following compounds were active at 40 ppm or less: 8, 10, 16, 17, 33, 35, 37, 38, 39, 40, 97, 55, 56, 59, 60, 62, 63, 64, 67, 68, 69, 70 71, 72, 73, 74, 77, 78, 93, 79, 80, 81, 90, 92, 87.

Tetranychus urticae

Leaf discs of infested french bean were sprayed with the solution containing the compound. Mortality was assessed after 2 days at 25° C.

The following compounds were active at 1000 ppm or less: 8, 12, 13, 16, 17, 18, 21, 26, 28, 31, 33, 34, 37, 54, 45, 47, 59, 60, 61, 63, 67, 69, 70, 77, 78, 93, 80, 82, 83, 84, 85, 92, 87.

Spodoptera littoralis

Uninfested leaves were sprayed with the test solution containing the compound and left to dry. These were then infested with 10 newly hatched larvae. Mortality was assessed after 3 days.

The following compounds were active at 1000 ppm or less: 1, 5, 6, 7, 13, 14, 15, 100, 18, 20, 21, 29, 34, 36, 37, 38, 40, 41, 42, 95, 44, 46, 49, 50, 51, 53, 55, 63, 65, 66, 67, 91.

The following compounds were active at 200 ppm or less: 3, 4, 8, 9, 10, 11, 16, 17, 19, 30, 31, 32, 33, 35, 39, 96, 97, 56, 57, 59, 60, 61, 62, 64, 68, 69, 70, 71, 72, 73, 74, 77, 78, 93, 94, 79, 80, 81, 82, 83, 84, 85, 86, 89, 90, 92, 87.

Myzus persicae 10 adult Myzus were placed on a leaf disc of chinese cabbage. 24 hours later the disc was sprayed with the solution containing the compound. Mortality was assessed after 2 days at 25° C.

The following compounds were active at 1000 ppm or less: 8, 9, 13, 18, 19, 20, 22, 24, 30, 31, 34, 35, 95, 44, 50, 59, 60, 61, 66, 72, 75, 77, 78, 93, 94, 82, 83, 84, 85, 86, 92, 87.

Diabrotica undecimpunctata

2nd instar larvae and their food were sprayed on filter paper with the solution containing the compound. Activity was assessed at 2 days.

The following compounds were active at 1000 ppm or less: 3, 6, 9, 11, 12, 13, 14, 17, 28, 29, 30, 31, 32, 33, 35, 37, 39, 95, 96, 97, 44, 54, 55, 56, 59, 61, 62, 63, 67, 69, 71, 72, 74, 77, 78, 94, 80, 81, 82, 83, 86, 92.

The following compounds were active at 200 ppm or less: 10, 16, 68, 73, 79, 84, 85, 89.

EXAMPLE B

Topical Application Tests

Blattella germanica 0.5μl of a solution of the compound in butanone (with or without piperonyl butoxide) was topically applied to male B. germanica. Mortality was assessed after 6 days.

The following compounds were active at 10μg or less (+piperonyl butoxide) 10, 11, 13, 15, 16, 17, 30, 35, 36, 37, 39, 40, 41, 42, 55, 56, 57, 59, 60, 61, 63, 64, 67, 68, 69, 70, 71, 72, 73, 74, 77, 78, 94, 79, 80, 81, 82, 83, 84, 85, 86, 92, 87.

The following compounds were active at 10 μg or less alone: 1, 8, 9, 20, 21, 30, 31, 32, 33, 34, 95.

We claim:

1. A compound of the formula (I):

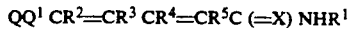

or a salt thereof, wherein Q is a substituted monocyclic aromatic ring, or fused bicyclic ring system of which at least one ring is aromatic containing 9 or 10 atoms of which one may be nitrogen and the rest carbon or the bicyclic ring system is substituted by one to four groups selected from $C_{1-6}$ hydrocarbyl, $C_{1-6}$ alkoxy or methylenedioxy, or $C_{1-6}$ hydrocarbyl, $C_{1-6}$ alkoxy or methylenedioxy substituted by one to three halos, or from halo, cyano or nitro, or the substituent on the Q ring is a group $S(O)_nR^7$ wherein n is 0, 1 or 2 and $R^7$ is $C_{1-6}$ alkyl or $C_{1-6}$ alkyl substituted by one or more halos or $R^7$ is amino or amino substituted by one or two $C_{1-6}$ alkyl groups or the substituent is a group $NR^8R^9$ where $R^8$ and $R^9$ are independently selected from hydrogen, $C_{1-6}$ alkyl or a group $COR^{10}$ where $R^{10}$ is $C_{1-6}$ alkyl, or Q is a dihalovinyl group or a group $R^6$—C≡C— where $R^6$ is $C_{1-4}$ alkyl, tri $C_{1-4}$ alkylsilyl, halogen or hydrogen;

$Q^1$ is a 1,2-cyclopropyl ring or a 1,2-cyclopropyl ring substituted by one or more groups selected from $C_{1-3}$ alkyl, halo, $C_{1-3}$ haloalkyl, alkynyl, or cyano;

$R^2$, $R^3$, $R^4$ and $R^5$ are the same or different with at least one being hydrogen and the others being independently selected from hydrogen, halo, $C_{1-4}$ alkyl or $C_{1-4}$ haloalkyl;

X is oxygen or sulfur; and $R^1$ is selected from hydrogen, $C_{1-8}$ hydrocarbyl and $C_{1-8}$ hydrocarbyl substituted by dioxalanyl, halo, cyano, trifluoromethyl, trifluoromethylthio or $C_{1-6}$ alkoxy, provided that the compound of formula (I) is not (±)-2E,4E)-N-Isobutyl-5-[trans-2-(2,6-dichloro-4-pyridyl) cyclo-propyl]-3-methylpenta-2,4-dienamide (±)-2E,4E)-N-(1,2-Dimethylpropyl)-5-[trans-2-(3,4-dichloropheny)cyclopropyl]penta-2,4-dienamide (±)-2e,4E)-N-(1,2-Dimethylpropyl)-5-[trans-2-(4-methoxyphenyl)cyclopropyl]penta-2,4-dienamide.

2. A compound of the formula (I) according to claim 1 in which Q is a naphthyl group or a substituted phenyl, pyridyl, thienyl or naphthyl group.

3. A compound of the formula (I) according to claim 1 in which $R^2$, $R^3$, $R^4$ and $R^5$ are chosen from hydrogen, methyl or fluoro.

4. A compound of the formula (I) according to any one of claim 1 in which the 1- and 3- positions of the cyclopropyl ring $Q^1$ are unsubstituted and the 2- position is unsubstituted or substituted by fluoro or chloro.

5. A compound of the formula (I) according to claim 1 in which $R^1$ is isobutyl, 1,2-dimethylpropyl 1,1,2-trimethylpropyl, 2,2-dimethylpropyl, 2-methylprop-2-enyl or (2-methyl-1,3-dioxan-2-yl) methyl.

6. A compound of the formula (II):

or a salt thereof wherein $Q^a$ is a phenyl or pyridyl group or fused bicyclic ring system of which at least one ring is aromatic containing 9 or 10 atoms of which one may be nitrogen and the rest are carbon or a substituted phenyl, pyridyl or fused bicyclic ring or Q is a dihalovinyl group or a group $R^{6a}$—C≡C— where $R^{6a}$ is $C_{1-4}$ alkyl, trialkylsilyl or hydrogen $Q^{1a}$ is a 1,2-cyclopropyl ring optionally substituted by one or more groups selected from $C_{1-3}$ alkyl, halo, or $C_{1-3}$ haloalkyl; $R^{2a},R^{3a},R^{4a}$ and $R^{5a}$ are the same or different with at least one being hydrogen and the others being independently selected from hydrogen, halo, $C_{1-4}$ alkyl or $C_{1-4}$ haloalkyl; $X^a$ is oxygen or sulphur; and $R^{1a}$ is selected from hydrogen, $C_{1-6}$ hydrocarbyl and $C_{1-6}$ hydrocarbyl substituted by dioxalanyl halo, cyano. trifluoromethyl trifluoromethylthio or $C_{1-6}$ alkoxy.

7. A compound selected from:

(±)-(2E,4E) N-(1,2-Dimethylpropyl)-5-[trans-2-(4-bromophenyl)cyclopropyl]penta-2,4-dienamide (±)-(2E/Z,4E) N-Isobutyl-3-methyl-5-(trans-2-(3,5-bistrifluoro methylphenyl) cyclopropyl)-2,4-dienamide (±)-(2E,4E) N-(1,2-Dimethylpropyl)-5-(trans-2-(3,5-bistrifluoro methylphenyl)cyclopropyl)-2,4-dienamide (±)-(2E,4E) N-(1,2-Dimethylpropyl)-5-(trans2-(3,4-dichlorophenyl) cyclopropyl) 2,4-dienamide (±)-(2E,4E) N-Isobutyl-3-methyl-5-(trans-2-(3,4-dichlorophenyl cyclopropyl)-2,4-dienamide.

(±)-(2E,4E) N-(1,2-Dimethylpropyl)-5-(trans-2-(4-chlorophenyl) cyclopropyl)-2,4-dienamide.

(±)-(2E,e4E) N-(1,2-Dimethylpropyl)-5-[trans-2-(3,4-dibromophenyl)cyclopropyl]penta-2,4-dienamide (±)-(2E,4E) N-Isobutyl-3-methyl-5-[trans-2-(3,4-dibromophenyl)cyclopropyl]penta-2,4-dienamide (±)-(2E,4E) N-Isobutyl-3-methyl-5-methyl-5-[trans-2-(4-chlorophenyl) cyclopropyl]penta-2,4-dienamide (±)-(2E,4E) -(2-Methylprop-2-enyl)-3-methyl-5-[trans-2-(3,4-dibromophenyl)cyclopropyl ]penta-2,4-dienamide (±)-(2E,4E) N-Isobutyl-3-methyl-5-[trans-2-(3-trifluoromethyl-4-chlorophenyl)cyclopropyl ]penta-2,4-dienamide (±)-2E,4E) N-Isobutyl-3-methyl-5-[trans-2-(3,5-dichloro-4-bromophenyl) cyclopropyl]penta-2,4-dienamide.

(±)-2E,4E) N-Isobutyl-3-methyl-5-[trans-2-(3,4,5-trichlorophenyl)cyclopropyl]penta-2,4-dienamide (±)-(2E,4Z) N-Isobutyl-3-methyl-4-fluoro-5-[trans-2-(3,4-dichlorophenyl)cyclopropyl]penta-2,4-dienamide (±)-(2E,4E) N-(1,2-Dimethylpropyl)-5-[trans-2-(3-chloro-4-bromophenyl) cyclopropyl]penta-2,4-dienamide.

(±)-(2E,4E) N-Isobutyl-3-methyl-5-[trans-2-(3-chloro-4-bromophenyl)cyclopropyl]penta-2, 4-dienamide (±)-(2E,4E) N-(1,2-Dimethylpropyl)-5-[trans-2-(3-bromo-4-chlorophenyl)cyclopropyl]penta-2,4-dienamide (±)-(2E,4E) N-(1,2-Dimethylpropyl-5-[r-1-fluoro-c-2-(3,4,5-trichlorophenyl)cyclopropyl]penta-2,4-dienamide (±)-(2E,4E) N-Isobutyl-3-methyl-5-[r-1-fluoro-c-2-(3,4,5-trichlorophenyl)cyclopropyl]penta-2,4-dienamide (±)-(2Z,4E) N-Isobutyl-2-fluoro-3-methyl-5-[trans-2-(3,4-dichlorophenyl)cyclopropyl]penta-2,4-dienamide (±)-(2Z,4E) N-(2-Methylprop-2-enyl)-2-fluoro-3-methyl-5-(trans-2-(3,4-dichlorophenyl) cyclopropyl]penta-2,4-dienamide (±)-(2E,4E) N-(sec-Butyl)-5-[trans-2-(3,4-dichlorophenyl)cyclopropyl]penta-2,4-dienamide (±)-(2E,4E) N-(1,2-Dimethylpropyl)-5-[r-1-fluoro-c-2-(3,4-dichlorophenyl)cyclopropyl]penta2,4-dienamide (±)-(2E/Z,4E) N-(2-Methylprop-2-enyl)-3-methyl-5-[r-1-fluoro-c-2-(3,4-dibromophenyl)cyclopropyl]penta-2,4-dienamide (±)-(2E/Z,4E) N-Isobutyl-3-methyl-5-[r-1-fluoro-c-2-(3,4-dibromophenyl)cyclopropyl]penta-2,4-dienamide (±)-(2E,4E) N-(1,2-Dimethylpropyl)-5-[r-1-fluoro-c-2-(3,4-dibromophenyl)cyclopropyl]penta-2,4-dienamide (±)-(2E/Z,4E) N-Isobutyl-3-methyl-5-[r-1-fluoro-c-2-(3,4-dichlorophenyl)cyclopropyl]penta-2,4-dienamide (±)-(2E,4E) N-(1,2-Dimethylpropyl)-5-[r-1-chloro-c-2-(3,4-dichlorophenyl)cyclopropyl]penta2,4-dienamide (±)-(2E,4Z) N-(2-Methylprop-2-enyl)-3-methyl-4-fluoro-5-[trans-2-(3,4-dichlorophenyl) cyclopropyl]penta-2,4-dienamide (±)-(2E,4E) N-Isobutyl-3-methyl-5-[r-1-chloro-2-c-(3,4-dichlorophenyl)cyclopropyl]penta--2,4-dienamide (±)-(2E/Z,4E) N-(2-Methylprop-2-enyl)-3-methyl-5-[r-1-fluoro-2-c-(3,4-dichlorophenyl) cyclopropyl]penta-2,4-dienamide (±)-(2E/Z,4E) N-(2-Methylprop-2-enyl)-3-methyl-5-[r-1-fluoro-2-c-(3,4-5-triclorophenyl) cyclopropyl]penta-2,4-dienamide (±)-(2E;4E) N-(2-Methylprop-2-enyl)-3-methyl-5-[trans-2-(3,4-dibromophenyl)cyclopropyl]penta-2,4-dienamide.

8. An insecticidal or acaricidal composition comprising a compound of formula (I) as defined in claim 1 in admixture with a carrier or diluent.

9. A synergised pesticidal composition comprising a compound of formula (I), as defined in claim 1, a synergist for the formula I compound and a carrier or diluent.

10. A mixture of a compound of formula (I) as defined in claim 1 and another pesticidal compound.

11. A method for the control of pests comprising application to the pest or to an environment susceptible to pest infestation of a pesticidally effective amount of a compound according to claim 1.

12. A method according to claim 1 wherein the environment is an animal.

13. A method according to claim 11 wherein the environment is a plant or tree.

14. A method according to claim 11 wherein the environment is stored products.

15. A compound of the formula:

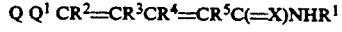

in which:

Q is phenyl substituted with a $C_{1-6}$ hydrocarbyl, $C_{1-6}$ alkoxy, $C_{1-6}$ hydrocarbyl substituted with 1 to 3 halos, or $C_{1-6}$ alkoxy substituted with 1 to 3 halos;

$Q^1$ is 1-2 cyclopropyl or 1-2 cyclopropyl subsituted with $C_{1-3}$ alkyl;

$R^1$ is hydrogen, $C_{1-8}$ hydrocarbyl, or $C_{1-8}$ hydrocarbyl substituted by halogen, trifluoromethyl or $C_{1-6}$ alkoxy;

$R^2$,c $R^3$, $R^4$ and $R^5$ are the same or different with at least one being hydrogen and the others being independently selected from hydrogen, halo, $C_{1-4}$ alkyl or $C_{1-4}$ haloalkyl; and X is O or S.

* * * * *